United States Patent
Zhong et al.

(10) Patent No.: US 9,080,942 B2
(45) Date of Patent: Jul. 14, 2015

(54) FLEXIBLE MULTI-MODULED NANOPARTICLE-STRUCTURED SENSOR ARRAY ON POLYMER SUBSTRATE AND METHODS FOR MANUFACTURE

(75) Inventors: Chuan-Jian Zhong, Endwell, NY (US); Jin Luo, Vestal, NY (US); Lingyan Wang, Binghamton, NY (US); Jun Yin, Binghamton, NY (US); Susan Lu, Vestal, NY (US)

(73) Assignee: The Research Foundation for State University of New York, Binghamont, NY (US)

( * ) Notice: Subject to any disclaimer, the term of this patent is extended or adjusted under 35 U.S.C. 154(b) by 284 days.

(21) Appl. No.: 13/325,978

(22) Filed: Dec. 14, 2011

(65) Prior Publication Data

US 2012/0156099 A1 Jun. 21, 2012

Related U.S. Application Data

(60) Provisional application No. 61/422,961, filed on Dec. 14, 2010.

(51) Int. Cl.
| | |
|---|---|
| *G01N 15/06* | (2006.01) |
| *G01N 33/00* | (2006.01) |
| *G01N 33/48* | (2006.01) |
| *G01N 27/12* | (2006.01) |

(Continued)

(52) U.S. Cl.
CPC .............. *G01N 27/127* (2013.01); *B82Y 15/00* (2013.01); *B82Y 30/00* (2013.01)

(58) Field of Classification Search
CPC .......... G01N 27/3271; G01N 33/5438; G01N 27/126; G01N 33/0031; G01N 21/783

USPC ....................... 422/68.1, 82.01, 82.02, 83, 98
See application file for complete search history.

(56) References Cited

U.S. PATENT DOCUMENTS

| | | | |
|---|---|---|---|
| 5,070,874 A | 12/1991 | Barnes et al. | |
| 5,238,729 A * | 8/1993 | Debe ............................ | 428/142 |
| 6,319,426 B1 * | 11/2001 | Bawendi et al. ....... | 252/301.4 R |

(Continued)

OTHER PUBLICATIONS

Hank Wohltjen and Arthur W. Snow, Colloidal Metal—Insulator—Metal Ensemble Chemiresistor Sensor, American Chemical Society, Published on web May 30, 1998, 4 pages.

(Continued)

*Primary Examiner* — Brian J Sines
(74) *Attorney, Agent, or Firm* — Paul Frank + Collins PC

(57) ABSTRACT

A flexible chemiresistor (CR) sensor for sensing a molecule of interest in a fluid (liquid or gas) is provided. The flexible CR sensor comprises a flexible chemiresistor (CR) module. The flexible CR module comprises a flexible substrate such polyethylene terephthalate (PET), polyethylene naphthalate (PEN) or polyimide (PI), and a thin film nanoparticle assembly assembled on the flexible substrate. The thin film nanoparticle assembly comprises metal or metal alloy core, ligand-capped nanoparticles and molecular linkers connecting the nanoparticles. The flexible CR sensor and an intelligent pattern recognition engine can be incorporated in a handheld device that can detect a molecule of interest in a fluid (e.g., a liquid or gas) accurately, rapidly, and without false positives. Any sensing array nanomaterial, pattern recognition, and compact/or electronic hardware can be integrated to achieve a desired detection limit and response speed.

12 Claims, 30 Drawing Sheets

(51) Int. Cl.
B82Y 15/00 (2011.01)
B82Y 30/00 (2011.01)

(56) References Cited

U.S. PATENT DOCUMENTS

| | | | |
|---|---|---|---|
| 6,458,256 B1 | 10/2002 | Zhong | |
| 2002/0132361 A1* | 9/2002 | Vossmeyer et al. | 436/151 |
| 2003/0109056 A1* | 6/2003 | Vossmeyer et al. | 436/169 |
| 2007/0114138 A1* | 5/2007 | Krasteva et al. | 205/787 |
| 2007/0122631 A1* | 5/2007 | Higuchi et al. | 428/429 |
| 2008/0278181 A1* | 11/2008 | Zhong et al. | 324/693 |
| 2009/0049890 A1* | 2/2009 | Zhong et al. | 73/23.3 |
| 2009/0148690 A1* | 6/2009 | Krasteva et al. | 428/323 |

OTHER PUBLICATIONS

Royce W. Murray, Nanoelectrochemistry: Metal Nanoparticles, Nanoelectrodes, and Nanopores, American Chemical Society, Published on web Jun. 18, 2008, 33 pages.
B.L.V. Prasad, C.M Sorensen, Chem Soc Review, 2008 Gold: Chemistry, Materials and Catalysis Issue, 14 pages.
Amir Zabet-Khosousi and Al-Amin Dhirani, Charge Transport in Nanoparticle Assemblies, American Chemical Society, Published on web Sep. 24, 2008, 53 pages.
Sujit Kumar Ghosh and Tarasankar Pal, Interparticle Coupling Effect on the Surface Plasmon Resonance of Gold Nanoparticles: From Theory to Applications, American Chemical Society, Published on web Nov. 14, 2007, 66 pages.
Erik J. Severin and Nathan S. Lewis, Relationships among Resonant Frequency Changes on a Coated Quartz Crystal Microbalance, Thickness Changes, and Resistance-Responses of Polymer—Carbon Black Composite Chemiresistors, American Chemical Society, Published on web Apr. 1, 2000, 8 pages.
Stephen D. Evans et al., Vapour Sensing Using Hybrid Organic-Inorganic Nanostructured Materials, The Royal Society of Chemistry, 2000, 6 pages.
Ruth Shinar, Guojun Liu, and Marc D. Porter, Graphite Microparticles as Coatings for Quartz Crystal Microbalance-Based Gas Sensors, Analytical Chemistry, vol. 72, No. 24, Dec. 15, 2000, 7 pages.
Stephanie I. Lim and Chuan-Jian Zhong, Molecularly Mediated Processing and Assembly of Nanoparticles: Exploring the Interparticle Interactions and Structures, Department of Chemistry, State University of Binghamton, Published on the web Apr. 20, 2009, 11 pages.
L. Y. Wang, J. Luo et al. Langmuir, The ACS Journal of Surfaces and Colloids, Jan. 15, 2010, ACD Publications, 17 pages.
Frank L. Leibowitz, Wenxia Zheng et al., Structures and Properties of Nanoparticles Thin Films Formed Via a One Step Exchange-Cross-Linking-Precipitation Route, Department of Chemistry, State University of New York at Binghamton, American Chemical Society, Published on web Oct. 8, 1999, 8 pages.
Wenxia Zheng, Mathew M. Maye et al., Imparting Biomimetic Ion-Gating Recognition Properties to Electrodes With a Hydrogen-Bonding Structured Core-Shell Nanoparticle Network, American Chemical Society Published on web Mar. 24, 2000, 10 pages.
Li Han, Mathew M. Maye et al., Quartz-crystal microbalance and spectrophotometric assessments of inter-core and inter-shell reactivities in nanoparticle thin film formation and growth, The Royal Society of Chemistry, 2001, 7 pages.
Li Han, David R. Daniel et al., Core-Shell Nanostructured Nanoparticle Films as Chemically Sensitive Interfaces, Analytical Chemistry, vol. 73, No. 18, Sep. 15, 2001, 9 pages.
Li Han, Xiajing Shi et al., Nanoparticle-structured sensing array materials and pattern recognition for VOC detection, Department of Chemistry, State University of New York at Binghamton, 11 pages.
Xiajing Shi, Lingyan Wang et al., A Multi-module artificial neural network approach to pattern recognition with optimized nanostructured sensor array, Sensors and Actuators B Chemical, 2006, 9 pages.

Eric J. Houser, Todd E. Mlsna, Rational materials design of sorbent coatings for explosives: applications with chemical sensors, Naval Research Laboratory, Material Science Division, Talanta 54 2001, 17 pages.
Francisco J. Ibanez and Francis P. Zamborini, Chemiresistive Sensing of Volatile Organic Compounds with Films of Surfactant-Stabilized Gold and Gold—Silver Alloy Nanoparticles, vol. 2, No. 8, 2008, 10 pages.
Francis P. Zamborini and Michael C. Leopold et al., Electron Hopping Conductivity and Vapor Sensing Properties of Flexible Network Polymer Films of Metal Nanoparticles, Contribution from the Kenan Laboratories of Chemistry, University of North Carolina, Feb. 18, 2002, 7 pages.
Francis P. Zamborini, Laura E. Smart et al., Distance-dependent electron hopping conductivity and nanoscale lithography of chemically-linked gold monolayer protected cluster films, Analytica Chimica Acta 496 (2003), 14 pages.
Qing-Yun Cai and Edward T. Zellers, Dual-Chemiresistor GC Detector Employing Monolayer-Protected Metal Nanocluster Interfaces, Analytical Chemistry, vol. 74, No. 14, Jul. 15, 2002, 7 pages.
Jay W. Grate et al., Sorptive Behavior of Monolayer-Protected Gold Nanoparticle Films: Implications for Chemical Vapor Sensing, Pacific Northwest National Laboratory, P.O. Box 999, Richland, Washington, published on web Mar. 20, 2003, 12 pages.
Yvonne Joseph et al., Gold Nanoparticles/Organic Networks as Chemiresistor Coatings: The Effect of Film Morphology on Vapor Sensitivity, American Chemical Society, published on web Jul. 22, 2008, 8 pages.
Yvonne Joseph et al., Self-Assembled Gold Nanoparticle/Alkanedithiol Films: Preparation, Electron Microscopy, XPS-Analysis, Charge Transport, and Vapor-Sensing Properties, American Chemical Society published Jun. 28, 2003, 8 pages.
L. Y. Wang et al., Sensing Arrays Constructed from Nanoparticle Thin Films and Interdigitated Microelectrodes, Sensors 2006, published Jun. 22, 2006, 13 pages.
Lingyan Wang et al., Array of Molecularly Mediated Thin Film Assemblies of Nanoparticles: Correlation of Vapor Sensing with Interparticle Spatial Properties, J. Am Chem. Soc., 2007, 10 pages.
Mark J. Schadt et al., Molecularly Tuned Size Selectivity in Thermal Processing of Gold Nanoparticles, Chemistry of Materials, vol. 18, No. 22, Oct. 31, 2006, 3 pages.
Nadejda Krasteva et al., Gold Nanoparticle/PPI-dendrimer based chemiresistors Vapor-sensing properties as a function of the dendrimer size, Materials Science Laboratories, Jan. 18, 2003, 7 pages.
Michael C. Leopold et al., Growth, conductivity, and vapor response properties of metal ion-carboxylate linked nanoparticle films, The Royal Society of Chemistry, Aug. 7, 2003, 14 pages.
Francisco J. Ibanez et al., Chemiresistive Vapor Sensing with Microscale Films of Gold Monolayer Protected Clusters, Department of Chemistry and Department of Electrical and Computer Engineering, Analytical Chemistry, vol. 78, No. 3, Feb. 1, 2006, 9 pages.
Heejoon Ahn et al., Comparison of Solubility and Vapor Sensing Properties of Methyl-and Thiophene-Terminated Alkanethiol-Protected Gold Nanoparticle Films, Journal of Macromolecular Science, Part A: Pure and Applied Chemistry, Aug. 21, 2006, 13 pages.
Barry Lavine et al., Chemometrics, Department of Chemistry, Oklahoma State University, Analytical Chemistry, vol. 78, No. 12, Jun. 15, 2006, 9 pages.
Chang-Yong Yang, A Vapor selectivity study of microsensor arrays employing various functionalized ligand protected gold nanoclusters, Department of Chemistry, Fu-Jen Catholic University, Hsinchuang, Taiwan, ROC, Mar. 10, 2006, 10 pages.
Pengfei Pang et al., Humidity effect on the dithiol-linked gold nanoparticles interfaced chemiresistor sensor for VOCs analysis, State Key Laboratory of Chemo/Biosensing and Chemometrics, Department of Chemistry, Aug. 19, 2005, 5 pages.
Marion E. Franke, Metal and Metal Oxide Nanoparticles in Chemiresistors: Does the Nanoscale Matter?, www.small-journal.com, 15 pages.

(56) References Cited

OTHER PUBLICATIONS

Michael J. Hostetler et al., Dynamics of Place-Exchange Reactions on Monolayer-Protected Gold Cluster Molecules, Kenan Laboratories of Chemistry, University of North Carolina, Apr. 30, 1999, 8 pages.
B. Abeles et al., Structural and Electrical Properties of Granular Metal Films, RCA Laboratories, Princeton, New Jersey 08540, US, 56 pages.
Guannan Roger Wang et al., Correlation Between Nanostructural Parameters and Conductivity Properties for Molecularly-Mediated Thin Film Assemblies of Gold Nanoparticles, Department of Chemistry, State University of New York at Binghamton, Nov. 21, 2006, 6 pages.
R.H. Friend et al., Electroluminescense in conjugated polymers, Macmillan Magazines Ltd., vol. 397, Jan. 14, 1999, 8 pages.
Mark E. Roberts et al., Flexible, plastic transistor-based chemical sensors, Department of Chemical Engineering, Stanford University, 2009, 7 pages.
Luisa Torsi, As Plastic Analytical Sensors, University of Texas at Austin, Analytical Chemistry, Oct. 1, 2005, 8 pages.
A. Petropoulos et al., Demonstration of a new technology which allows direct sensor integration on flexible substrates, The European Physical Journal Applied Physics, Jan. 5, 2009, 4 pages.
D. Briand et al., Integration of MOX gas sensors on polyimide hotplates, Sensors and Actuators B 130, available online at www.sciencedirect.com, Sep. 15, 2007, 6 pages.
Frank Liao et al., Organic TFTs as gas sensors for electronic nose applications, Departments of Electrical Engineeering and Computer Sciences, available online at www.sciencedirect.com, Jan. 8, 2005, 7 pages.
Yong Shin Kim, Microheater-integrated single gas sensor array chip fabricated on flexible polyimide substrate, Biosensor Team, Electronics and Telecommunications Research Institute, available online at www.sciencedirect.com, 8 pages.
M.F. Mabrook et al., Inkjet-printed polypyrrole thin films for vapour sensing, School of Engineering and Centre for Molecular and Nanoscale Electronics, available online at www.sciencedirect.com, Nov. 22, 2005, 5 pages.
Neerja Saran et al., Fabrication and Characterization of Thin Films of Single-Walled Carbon Nanotube Bundles on Flexible Plastic Substrates, Department of Chemistry, JACA Communications, Mar. 3, 2004, 2 pages.
Kunjal Parikh et al., Flexible vapour sensors using single walled carbon nanotubes, Alan G. MacDiarmid Laboratories for Technical Innovation, Sensors and Actuators B Chemical, available online at www.sciencedirect.com, Mar. 13, 2005, 9 pages.
Bo Li et al., Inkjet printed chemical sensor array based on polythiophene conductive polymers, Department of Electrical and Computer Engineering, Sensors and Actuators B Chemical, available at www.sciencedirect.com, Nov. 30, 2006, 10 pages.
Chi-Yuan Lee, Fabrication of micro sensors on a flexible substrate, Department of Mechanical Engineering, Sensors and Actuators A: Physical, journal homepage: www.elsevier.com/locate/sna, 4 pages.
Pi-Guey Su et al., Novel fully transparent and flexible humidity sensor, Department of Chemistry, Chinese Culture University, Taiwan, Sensors and Actuators B: Chemical, journal homepage: www.elsevier.com/locate/snb, 5 pages.
Pi-Guey Su et al., Flexible humidity sensor based on $TiO_2$ nanoparticles-polypyrrole-poly-[3-(methacrylamino) propyl] trimethyl ammonium chloride composite materials, Department of Chemistry, Sensors and Actuators B, Sep. 15, 2007, 6 pages.
Pi-Guey Su et al., Novel Flexible Resistive-type humidity sensor, Department of Chemistry, Sensors and Actuators B, available online at www.sciencedirect.com, Dec. 8, 2006, 6 pages.
Yugang Sun et al., Electrodeposition of Pd Nanoparticles on single-walled carbon nanotubes for flexible hydrogen sensors, Applied Physics Letters, Published by American Institute of Physics, 4 pages.

Michael C. McAlpine et al., Highly ordered nanowire arrays on plastic substrates for ultrasensitive flexible chemical sensors, Division of Chemistry and Chemical Engineering, vol. 6, May 2007, published Apr. 22, 2007, 7 pages.
I. Sayago et al., Novel selective sensors based on carbon nanotube films for hydrogen detection, Sensors and Actuators B Chemical, available online at www.sciencedirect.com, Jun. 16, 2006, 6 pages.
Kyle Cattanach et al., Flexible Carbon Nanotube Sensors for Nerve Agent Simulants, Institute of Physics Publishing, 2006, 7 pages.
Dongliang Fu et al., Differentiation of Gas Molecules Using Flexible and All-Carbon Nanotube Devices, The Journal of Physical Chemistry C Letters, 2008, 4 pages.
Valery R. Marinov et al., Direct-Write Vapor Sensors on FR4 Plastic Substrates, IEEE Sensors Journal, vol. 7, No. 6, Jun. 6, 2007, 8 pages.
Yvonne Joseph et al., Vapor Sensitivity of Networked Gold Nanoparticle Chemiresistors: Importance of Flexibility and Resistivity of the Interlinkage, American Chemical Society, Published on the web Aug. 4, 2007, 5 pages.
Mathew M. Maye et al., Heating-Induced Evolution of Thiolate-Encapsulated Gold Nanoparticles: A Strategy for Size and Shape Manipulations, Department of Chemistry, State University of New York at Binghamton, Published on the web Nov. 4, 1998, 8 pages.
Li Han et al., Novel Interparticle Spatial Properties of Hydrogen-Bonding Mediated Nanoparticle Assembly, Department of Chemistry, State University of New York at Binghamton, Published on the web Nov. 28, 2002, 9 pages.
Mathew M. Maye et al. Probing pH-Tuned Morphological Changes in Core—Shell Nanoparticle Assembly Using Atomic Force Microscopy, Department of Chemistry, State University of New York at Binghamton, 2001, 5 pages.
Jin Luo et al., Spectroscopic Characterizations of Molecularly Linked Gold Nanoparticle Assemblies Upon Thermal Treatment, Department of Chemistry, State University of New York at Binghamton, Published on the web Mar. 17, 2004, 7 pages.
Nancy N. Kariuki et al., Preparation and Characterization of Gold Nanoparticles Dispersed in Poly (2-hydroxyethyl methacrylate), Department of Chemistry, State University of New York at Binghamton, Published on the web Sep. 19, 2002, 5 pages.
Jin Luo et al., Thermal Activation of Molecularly-Wired Gold Nanoparticles on a Substrate as Catalyst, Department of Chemistry, State University of New York at Binghamton, Aug. 26, 2002, 2 pages.
Jin Luo et al., AFM Probing of Thermal Activation of Molecularly Linked Nanoparticle Assembly, Department of Chemistry, State University of New York at Binghamton, Published on the web Jun. 12, 2004, 9 pages.
Mathias Brust et al., Synthesis of Thiol-derivatised Gold Nanoparticles in a Two-phase Liquid-Liquid System, Department of Chemistry, The University of Liverpool, United Kingdom, 1994, 2 pages.
D. Bethell et al., From monolayers to nanostructured materials: an organic chemist's view of self-assembly, Department of Chemistry, University of Liverpool, United Kingdom, 1995, 7 pages.
Michael J. Hostetler et al., Alkanethiolate Gold Cluster Molecules With Core Diameters from 1.5 to 5.2 nm: Core and Monolayer Properties as a Function of Core Size, Kenan Laboratories of Chemistry, University of North Carolina, Published on the web Jan. 6, 1998, 14 pages.
Cliff Hague, Insulin Pumps—Evolution of an Industry, Business Briefing: European Pharmacotherapy 2003, 3 pages.
C. J. Zhong et al, SUNY Binghamton New Technology Disclosure 2005, 8 pages.
Joseph Walsh, End of Spectrum a Breath of Fresh Air in Diabetes Detection, Mississippi State University's Dial Lab Has Developed a Sensor That Uses Cavity Ringdown Spectroscopy to Noninvasively Screen for the Disease, Spectroscopy Oct. 2004, 1 page.
Shirshendu Chakraborty et al., Detection of Biomarker in breath: A Step towards noninvasive diabetes monitoring, Current Science, vol. 94, No. 2, Jan. 25, 2008, 7 pages.
Michael Phillips et al., Increased breath biomarkers of oxidative stress in diabetes mellitus, Clinica Chimica Acta, 2004, 6 pages.
Pietro R. Galassetti et al., Breath Ethanol and Acetone as Indicators of Serum Glucose Levels: An Initial Report, Diabetes Technology & Therapeutics, vol. 7, No. 1, 2005, 11 pages.

(56) References Cited

OTHER PUBLICATIONS

Seong M. Cho et al., Two-step preconcentration for analysis of exhaled gas of human breath with electronic nose, Sensors and Actuators B, 2006, 8 pages.
Norio Teshima et al., Determination of acetone in breath, Analytica Chimica Acta, 2005, available online at www.sciencedirect.com, 11 pages.
Chunhui Deng et al., Determination of acetone in human breath by gas chromatography-mass spectrometry and solid-phase microextraction with on-fiber derivatization, Journal of Chromatography B, 2004, 7 pages.
Gosta Rooth et al., Acetone in Alveolar Air, and the Control of Diabetes, from the Department of Research and Medicine, University Hospital, Lund, Sweden, 5 pages.
C.N. Tassopoulos et al., Breath-Acetone and Blood-Sugar Measurements in Diabetes, from the Department of Medicine, Royal Postgraduate Medical School, London, 1969, 6 pages.
Oscar B. Crofford et al., Acetone in Breath and Blood, from the Department of Medicine, Venderbilt University School of Medicine, Nashville, Tennessee, 1977, 12 pages.
Wu-Hsun Cheng and Wen-Jin Lee, Technology development in breath microanalysis for clinical diagnosis, Review Articles, Kweishan, Taoyuan, Taiwan, Republic of China, 1999, 11 pages.
S.V. Ryabtsev et al., Application of semiconductor gas sensors for medical diagnostics, Sensors and Actuators B, 1999, 4 pages.
Chuji Wang et al., A Study on Breath Acetone in Diabetic Patients Using a Cavity Ringdown Breath Analyzer: Exploring Correlations of Breath Acetone With Blood Glucose and Glycohemoglobin A1C, IEEE Sensors Journal, vol. 10, No. 1, Jan. 2010, 10 pages.
Qintao Zhang et al., Diagnosis of diabetes by image detection of breath using gas-sensitive laps, Biosensors & Bioelectronics, 2000, 8 pages.
Ilona Koronczi et al., Medical Diagnosis With the Gradient Microarray of the KAMINA, IEEE Sensors Journal, vol. 2, No. 3, Jun. 2002, 6 pages.
Tomasz Ligor, Analytical Methods for Breath Investigation, Critical Review in Analytical Chemistry, available online as of Jan. 26, 2009 at http://www.tandfonline.com/loi/batc20, 12 pages.
Chuji Wang et al., Breath Analysis Using Laser Spectroscopic Techniques: Breath Biomarkers, Spectral Fingerprints, and Detection Limits, Open Access Sensors, 2009, 34 pages.
F. Di Francesco et al., Breath Analysis: Trends in techniques and clinical applications, Science Direct Microchemical Journal 79, 2005, 6 pages.
Marco Righettoni et al., Si: $Wo_3$ Sensors for Highly Selective Detection of Acetone for Easy Diagnosis of Diabetes by Breath Analysis, Analytical Chemistry, vol. 82, No. 9, May 1, 2010, 7 pages.
L. Wang et al., Ferroelectric $WO^3$ Nanoparticles for Acetone Selective Detection, American Chemical Society, Published on the web Jul. 4, 2008, 3 pages.
Kyoung Moo Choi et al., Determination of Gastric emptying in nonobese diabetic mice, American Physiological Society, 2007, 8 pages.
Brett C. Ginsburg, Mouse Breathalyzer, Alcohol Clinical and Experimental Research, vol. 32, No. 7, 2008, 5 pages.
Koichi Matsumura et al., Urinary Volatile Compounds as Biomarkers for Lung Cancer: A Proof of Principle Study Using Odor Signatures in Mouse Models of Lung Cancer, Plos One, vol. 5, Issue 1, Jan. 2009, 11 pages.
Tamar Shalev et al., Evaluation of the $^{13}C$-Octanoate Breath Test as a Surrogate Marker of Liver Damage in Animal Models, Digestive Diseases and Sciences, 2010, 11 pages.
Lewis L. Hsu et al., Computed Tomography Imaging of Lungs in Mouse Models of Human Disease—Advancing the Computing Interfaces with Physiology, Proceedings of the 17th IEEE Symposium on Computer-Based Medical Systems, 6 pages.
Jianpu Wang et al., Intracellular delivery of adenosine triphosphate enhanced healing process in full-thickness skin wounds in diabetic rabbits, Department of Surgery, School of Medicine, University of Louisville, The American Journal of Surgery, 2010, 10 pages.
Paritosh P. Wattamwar et al., Antioxidant Activity of Degradable Polymer Poly(troloxester) to Supress Oxidative Stress Injury in the Cells, Advanced Functional Materials, 2010, 8 pages.
A.W. Jones et al., Comparison of ethanol concentrations in venous blood and end-expired breath during a controlled drinking study, Forensic Science International 132, 2003, 8 pages.
Rod G. Gullberg et al., Breath alcohol measurement variability associated with different instrumentation and protocols, Forensic Science International, 2003, 6 pages.
Michael Phillips et al., Volatile organic compounds in breath as markers of lung cancer: a cross-sectional study Lancet 1999, 353: 1930-33, 4 pages.
Ikuo Ueta et al., Breath acetone analysis with miniaturized sample preparation device: In-needle preconcentration and subsequent determination by gas chromatography-mass spectroscopy, Journal of Chromatography B, School of Materials Science, Toyohashi University of Technology Japan, 2009, 6 pages.
Winston Hu and Pietro Galassetti, MD, PhD., Ethnicity & Disease, vol. 16, 2005-2006, 2 pages.
Jane Lee et al., Improved predictive models for plasma glucose estimation from multi-linear regression analysis of exhaled volatile organic compounds, Departments of Pharmacology, Pediatrics and Chemistry, and General Clinical Research Center/Institute for Clinical Translational Science, University of California, Irvine, Orange, California, May 2, 2009, 7 pages.
Wenqing Cao and Yixiang Duan, Breath Analysis: Potential for Clinical Diagnosis and Exposure Assessment, Clinical Chemistry, 2006, 12 pages.
Michael Phillips, Breath Tests in Medicine, Scientific American, Jul. 1992, 6 pages.
N. Makisimovich et al., Adsorption semiconductor sensor for diabetic ketoacidosis diagnosis, Sonar Research Center for Biotechnological Systems National Academy of Sciences, Kiev, Ukraine, Sensors and Actuators B, 1996, 3 pages.
Maximilian Fleischer et al., Detection of volatile compounds correlated to human diseases through breath analysis with chemical sensors, Siemens, AG, Corporate Technology, Germany, Sensors and Actuators, 2002, 5 pages.
Wolfgang Vautz et al., Analyses of mouse breath with ion mobility spectrometry: a feasibility study, Department of Metabolomics, Germany, Innovative Methodology, Jan. 14, 2010, 9 pages.
Chuan-Jian Zhong et al., Fuel Cell Technology: nano-engineered multimetallic catalysts, Department of Chemistry, State University of New York at Binghamton, Energy & Environment Science, 2008, 13 pages.
Lingyan Wang et al., Flexible chemiresistor sensors: thin film assemblies of Nanoparticles on a polyethylene terephthalate substrates, Journal of Materials Chemistry, 2010, 9 pages.
Joon-Boo Yu et al., Analysis of diabetic patient's breath with conducting polymer sensor array, Department of Material Science and Metallurgy Engineering, Republic of Korea, Sensors and Actuators B 108, 2005, 4 pages.
Yvonne Joseph et al., Vapor Sensitivity of Networked Gold Nanoparticle Chemiresistors: Importance of Flexibility and Resistivity of the Interlinkage, Materials Science Laboratory Germany, American Chemical Society, published on the web Aug. 4, 2007, 5 pages.
C. Drake et al., Metallic nanostructured materials based sensors, International Materials Reviews, vol. 52, No. 5, 2007, 30 pages.
Silvano Dragonieri et al., An electronic nose in the discrimination of patients with non-small cell lung cancer and COPD, Lung Cancer 64, 2009, pp. 166-170.
Xing Chen et al., A Study of the Volatile Organic Compounds Exhaled by Lung Cancer Cells in Vitro for Breath Diagnosis, American Cancer Society, published on the web Jun. 28, 2007, 10 pages.
Jeffrey J. Atkinson et al., Clara cell adhesion and migration to extracellular matrix, Respiratory Research, Published Jan. 7, 2008, 11 pages.

* cited by examiner

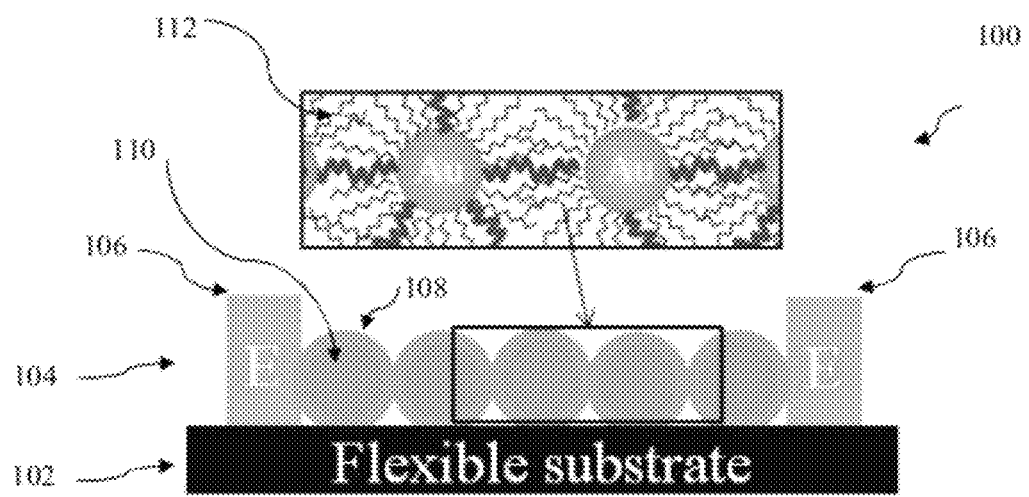
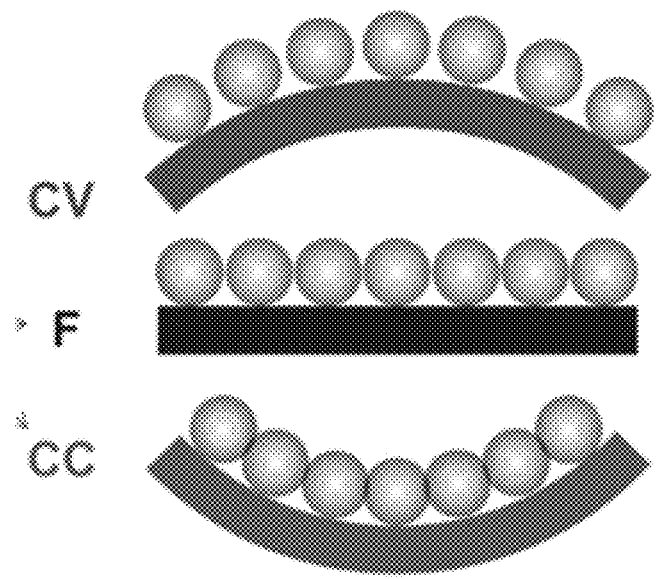
FIGS. 1A-B

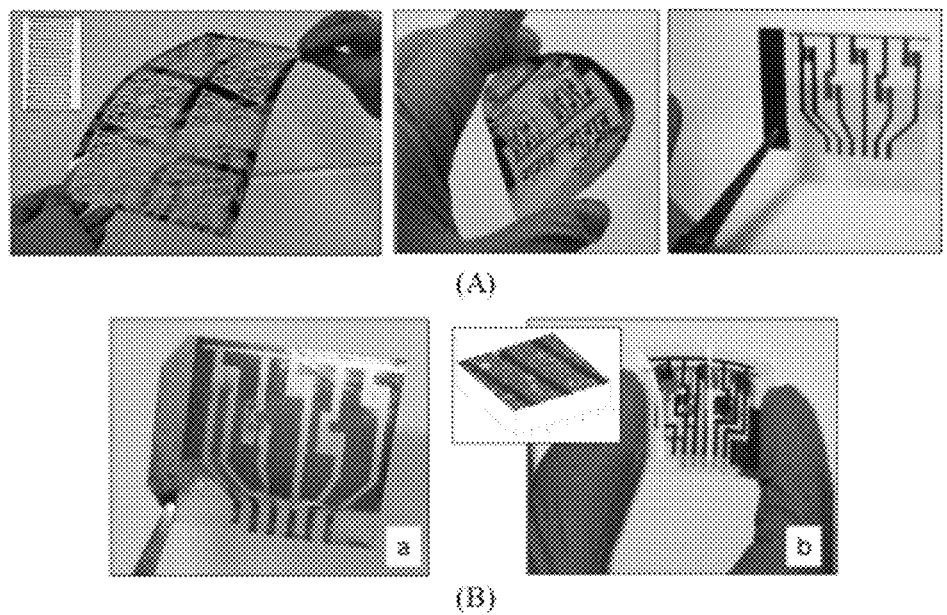
FIGS. 2A-B

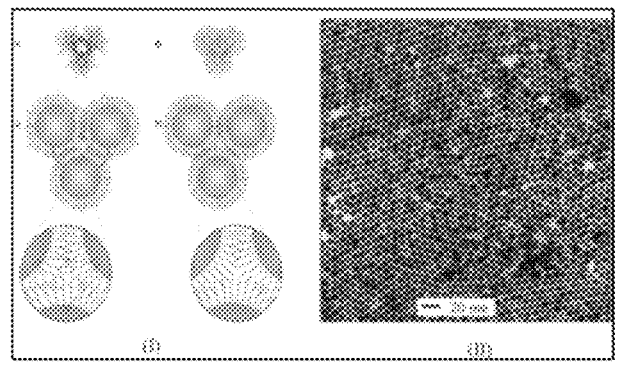
(A)
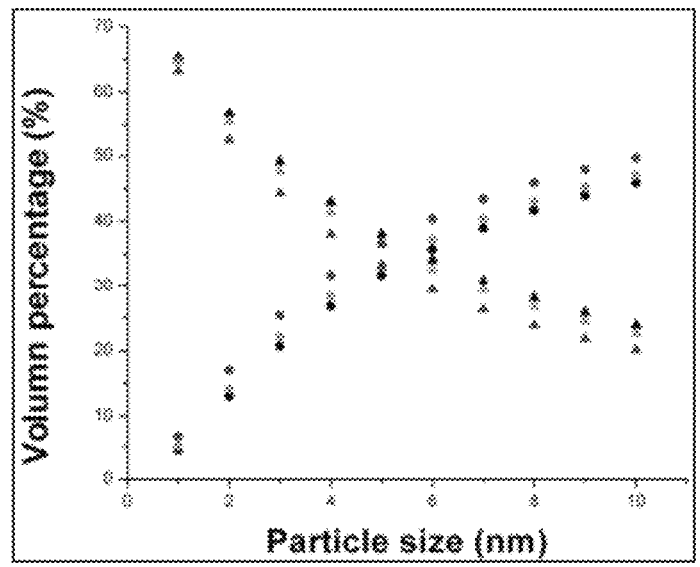
(B)
FIGS. 3A-B

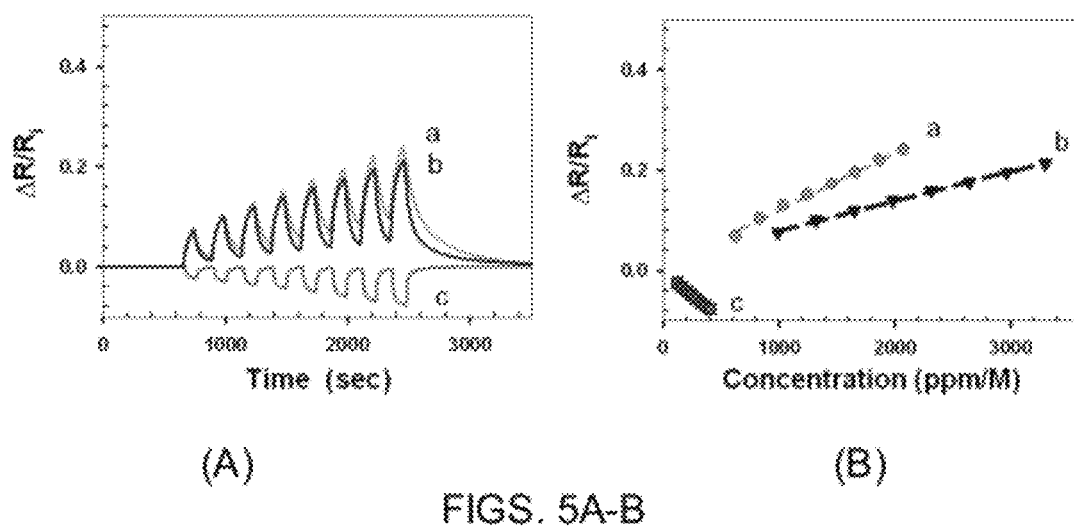
FIGS. 5A-B

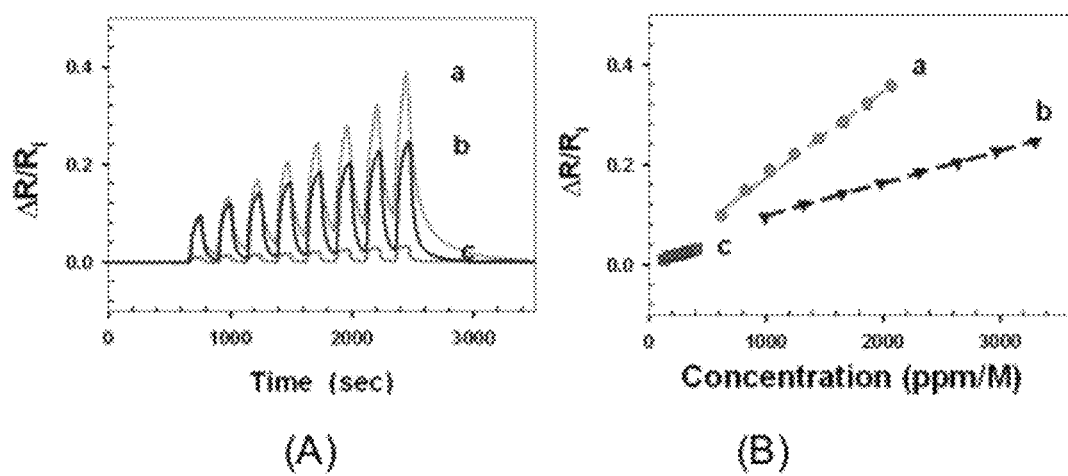
FIGS. 6A-B

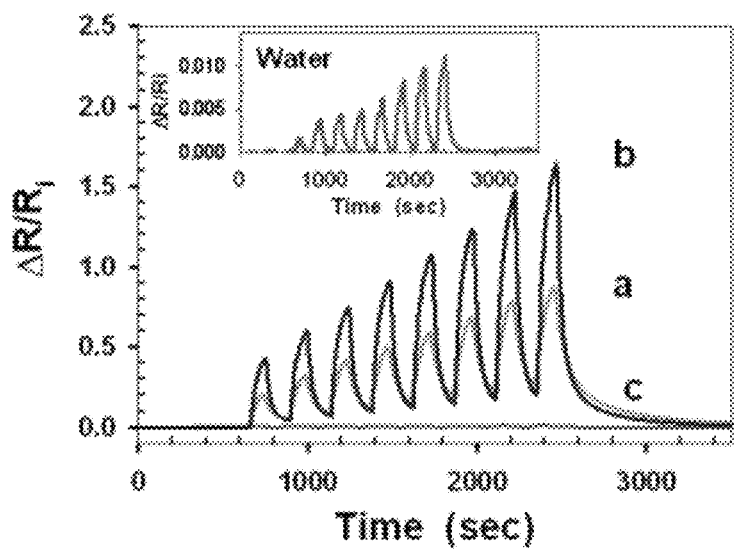
(A)
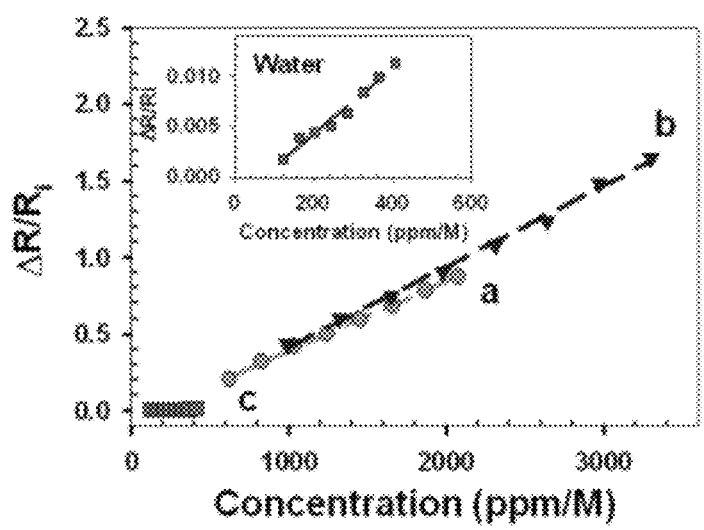
(B)
FIGS. 7A-B

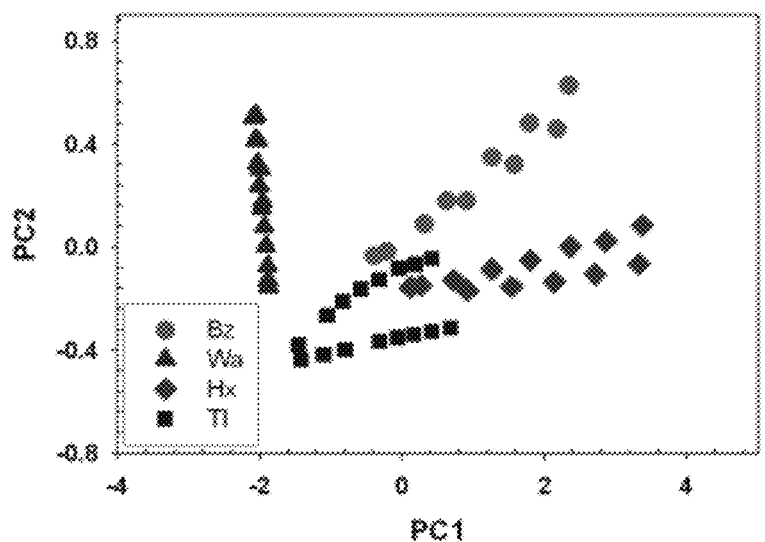
(A)
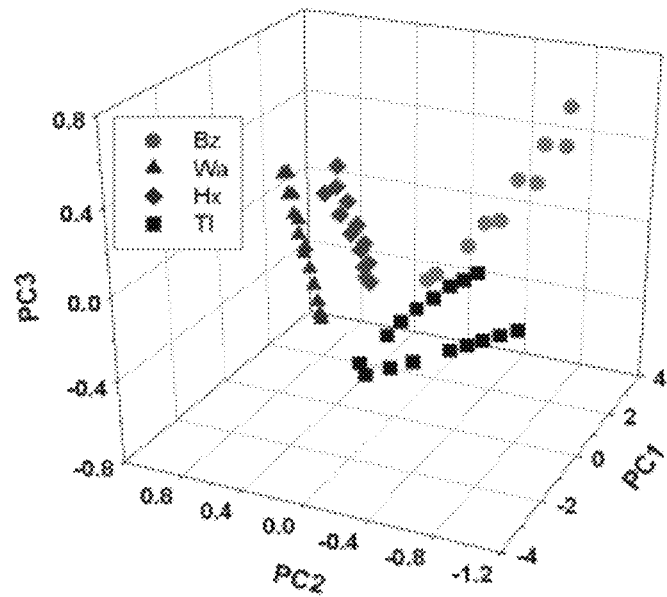
(B)
FIGS. 8A-B

Scheme 1

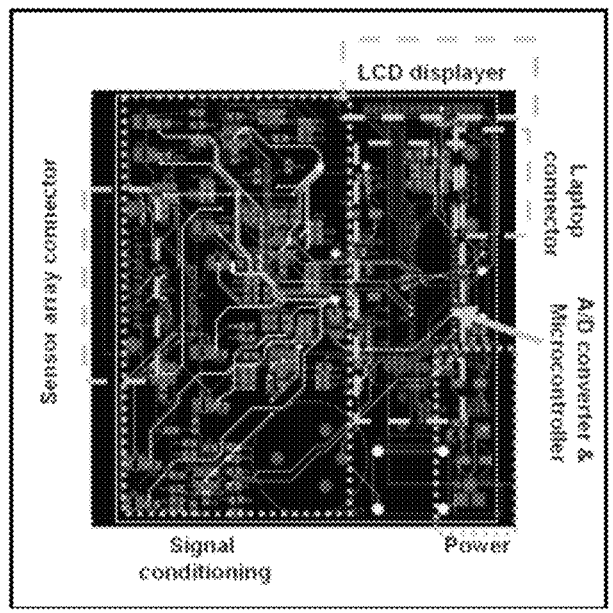
(A)
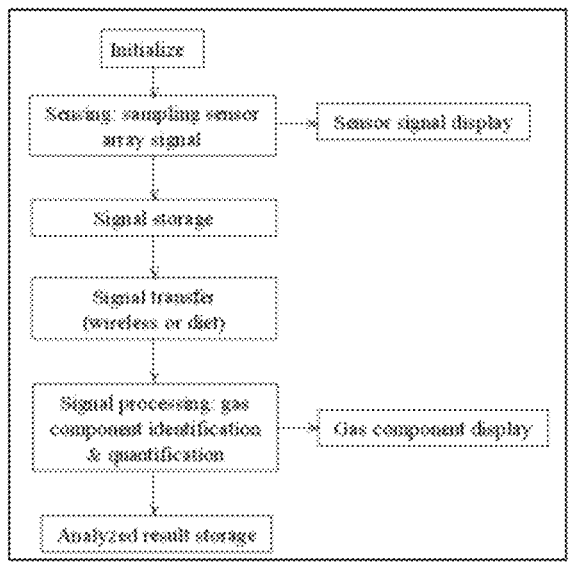
(B)
FIGS. 11A-B

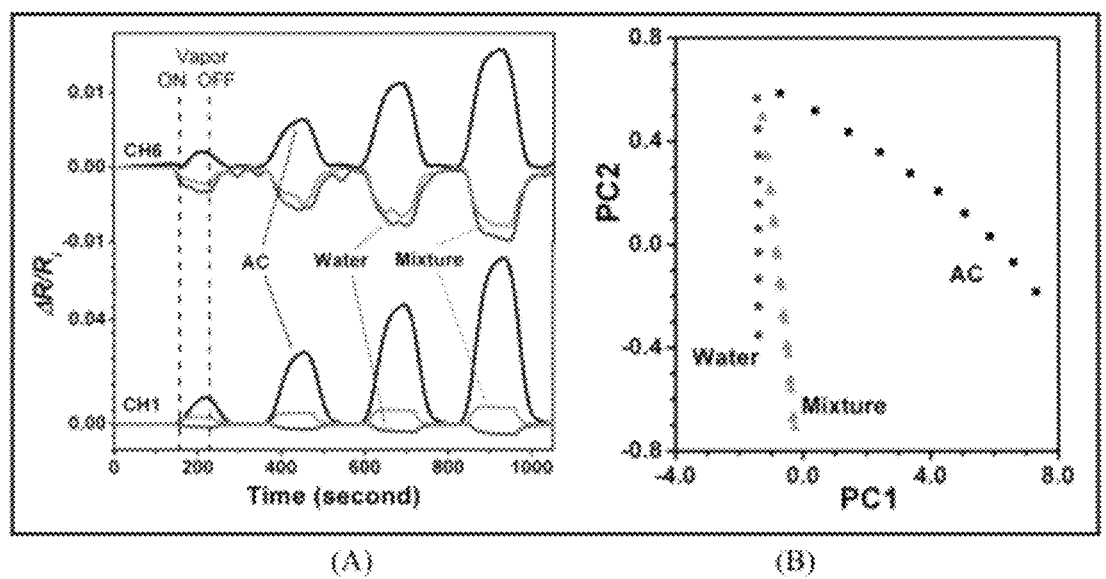
FIGS. 14A-B

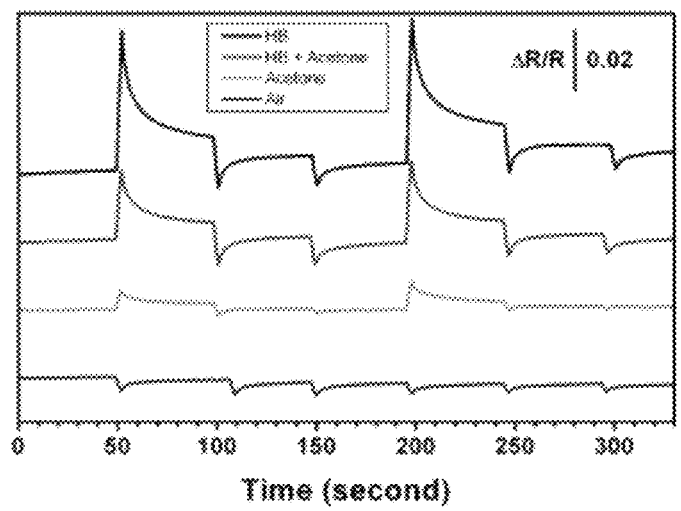
(A)
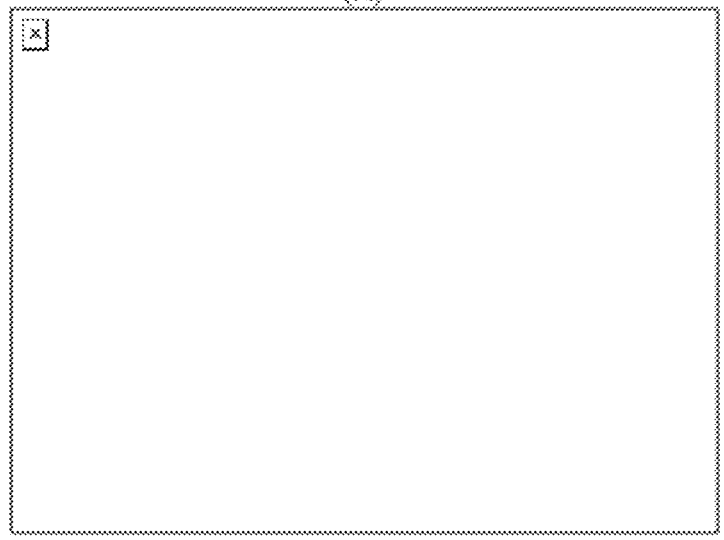
(B)
FIGS. 15A-B

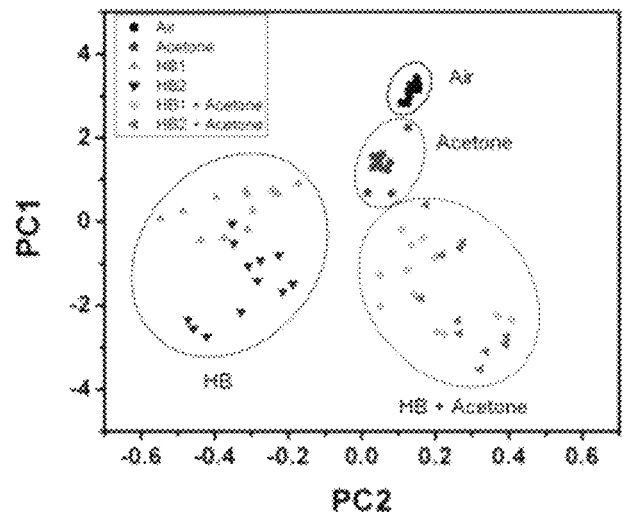
(A)
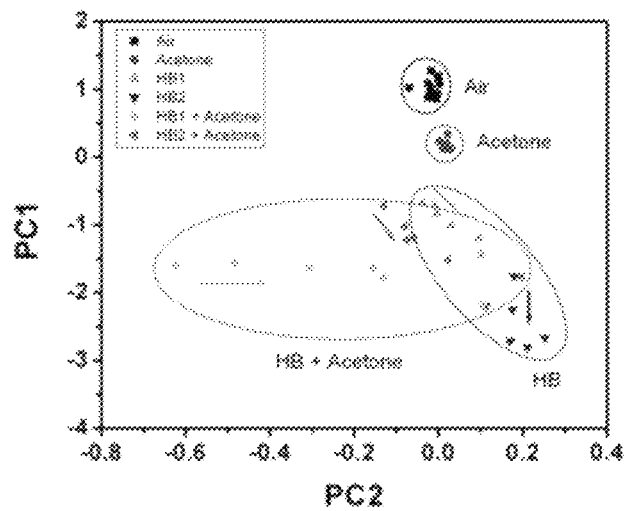
(B)
FIGS. 16A-B

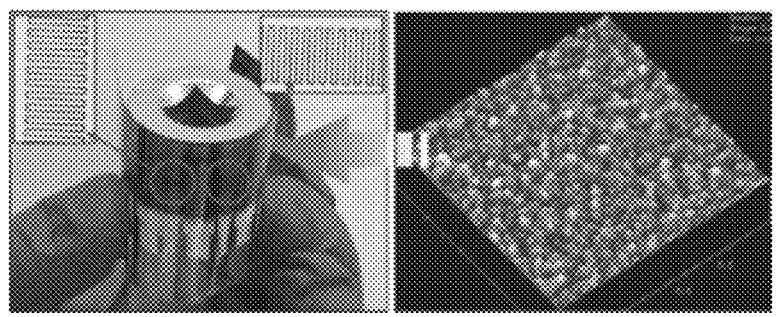
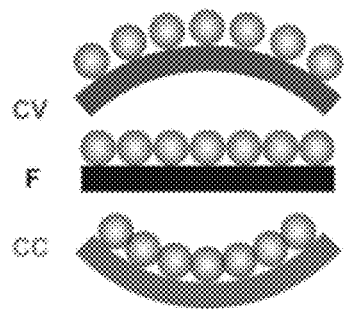 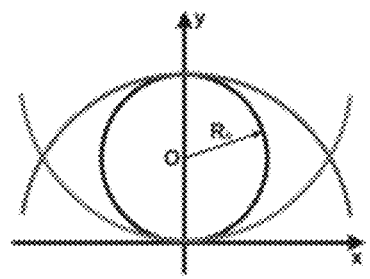
FIGS. 18 A-D

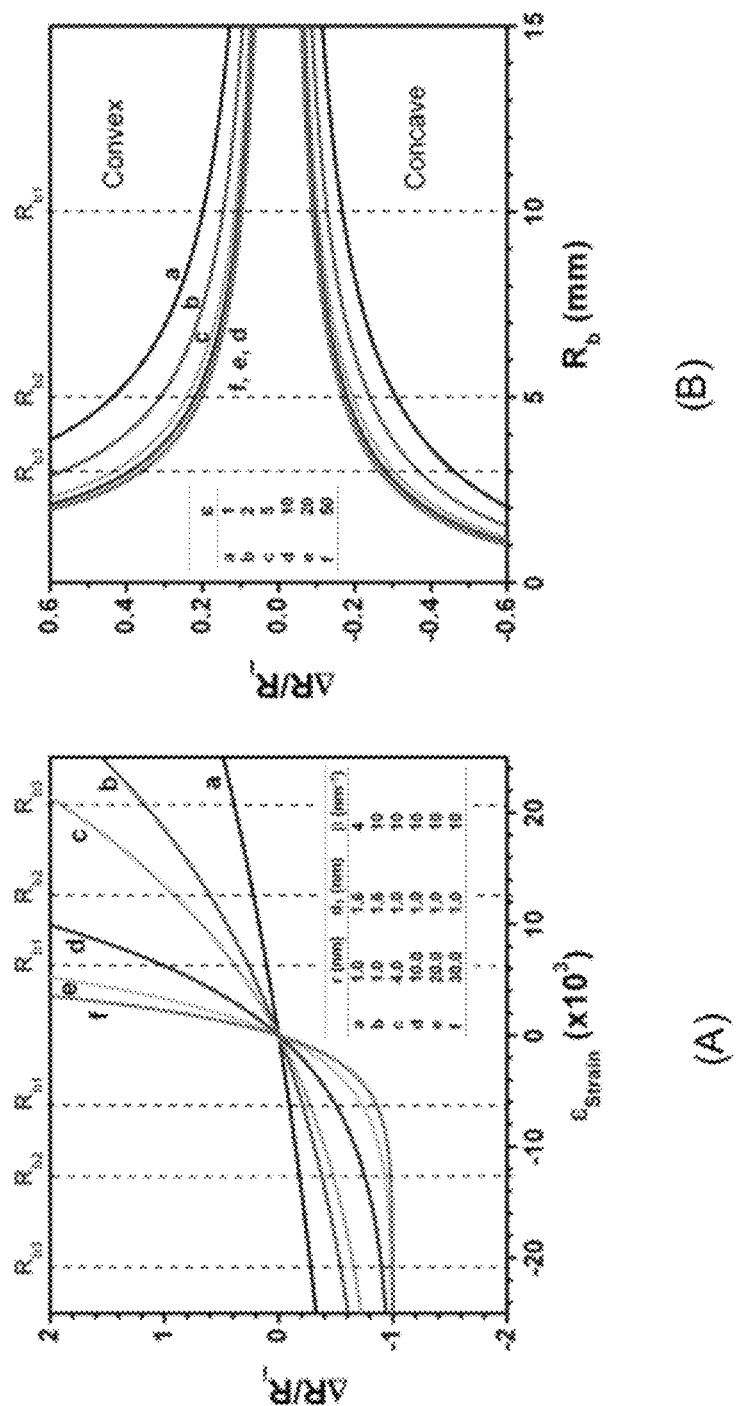
FIGS. 19A-B

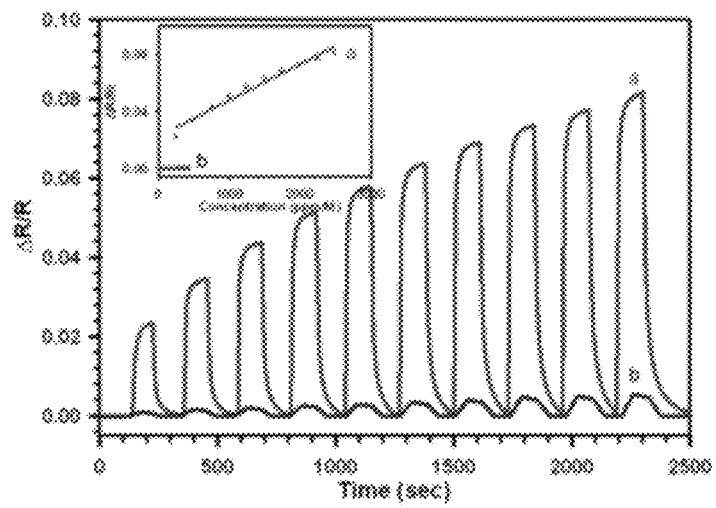
(A)
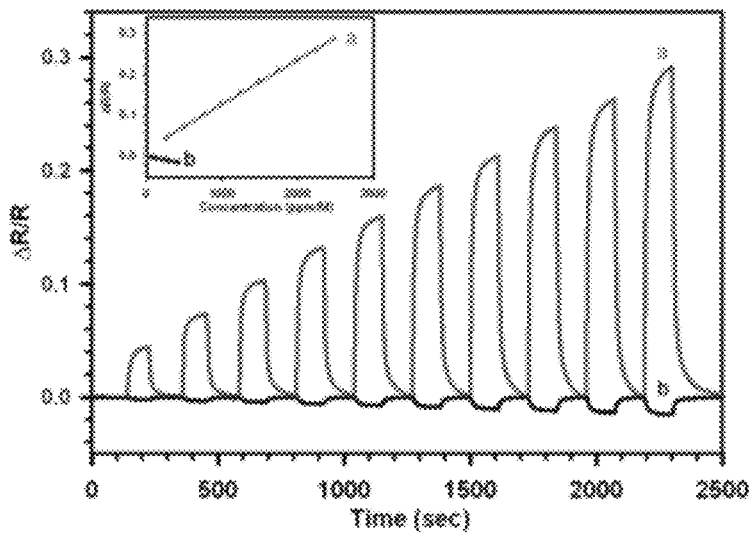
(B)
FIGS. 20A-B

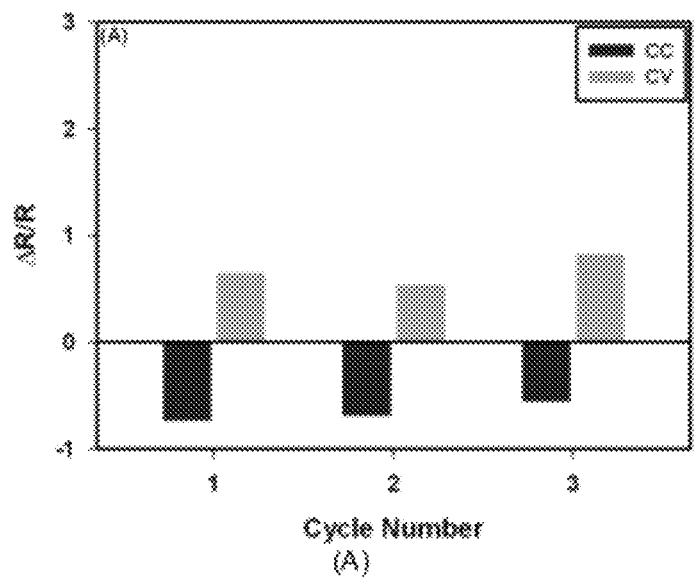
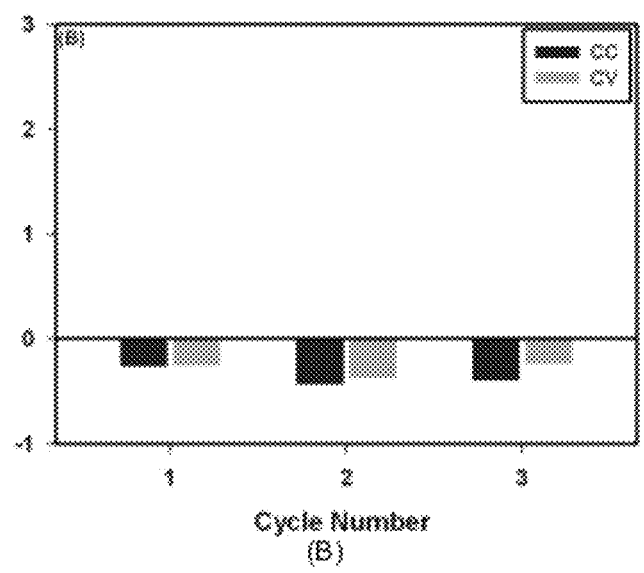
FIGS. 21A-B

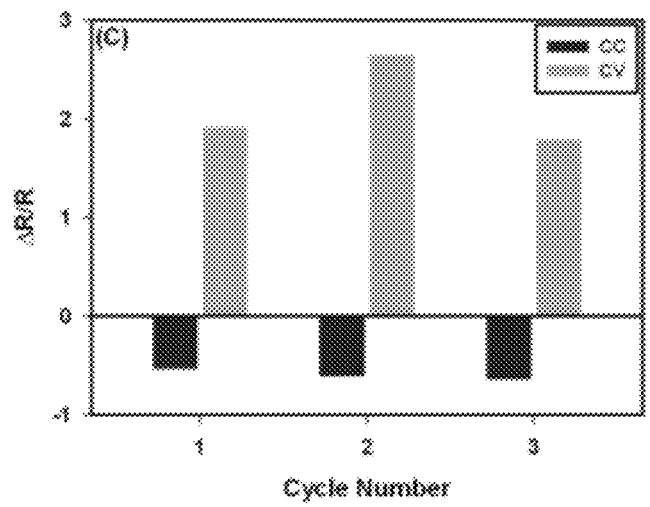
(C)
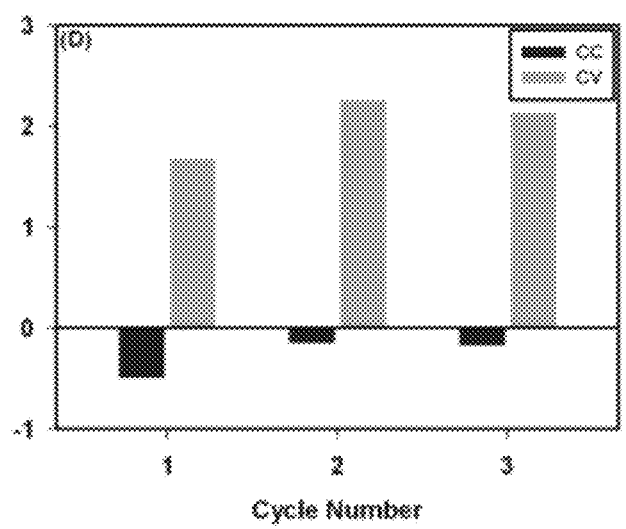
(D)
FIGS. 21C-D

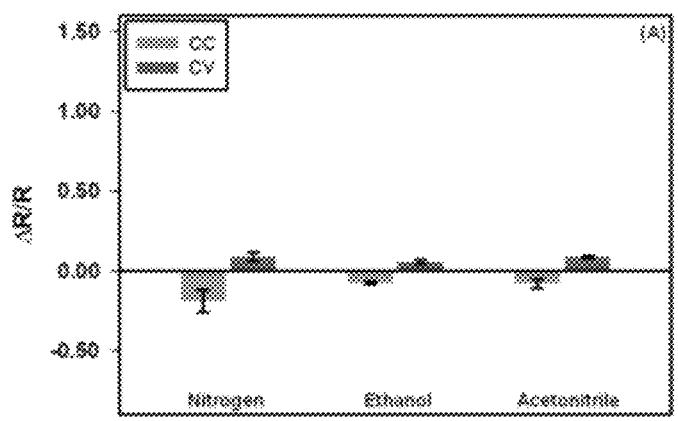
(A)
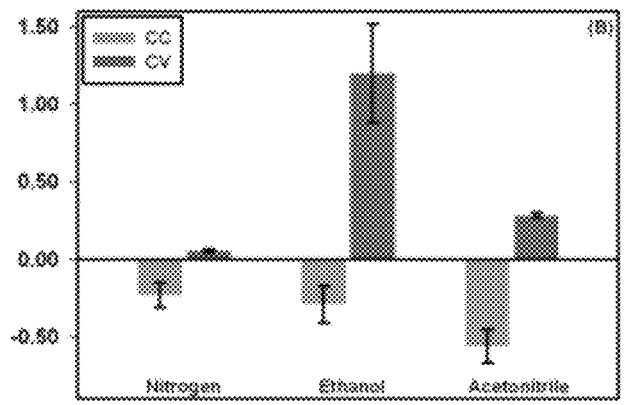
(B)
FIGS. 24A-B

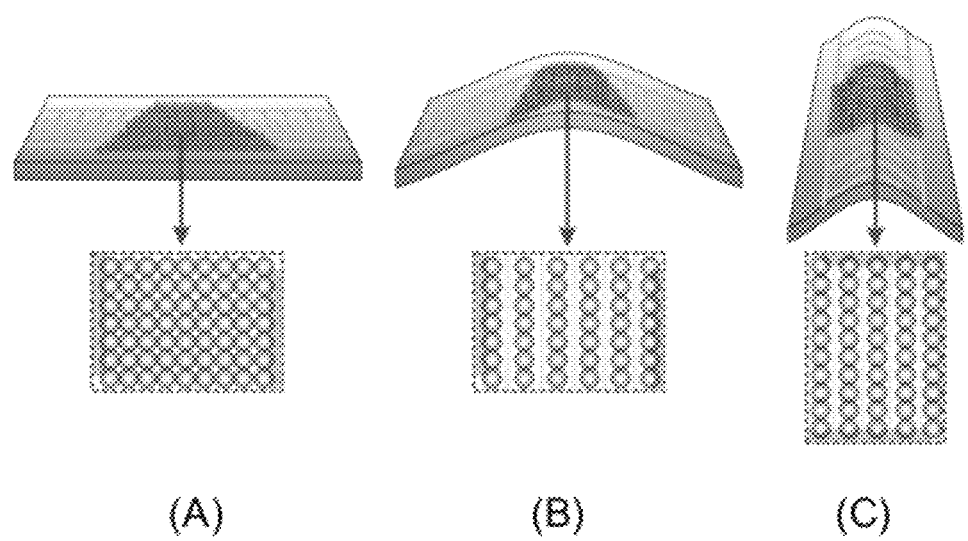
FIGS. 25A-C

FLEXIBLE MULTI-MODULED NANOPARTICLE-STRUCTURED SENSOR ARRAY ON POLYMER SUBSTRATE AND METHODS FOR MANUFACTURE

CROSS-REFERENCE TO RELATED APPLICATIONS

This application claims the benefit of priority under 35 U.S.C. 119(e) to U.S. Provisional Patent Application Ser. No. 61/422,961, filed on Dec. 14, 2010, and entitled "Flexible Multi-Moduled Nanoparticle-Structured Sensor Array on Polymer Substrate and Method for Manufacture." This application is a continuation-in-part of pending U.S. patent application Ser. No. 12/104,984, filed Apr. 17, 2008, and entitled "Multi-Moduled Nanoparticle-Structured Sensing Array and Pattern Recognition Device for Detection of Acetone in Breath," which claims priority to U.S. Provisional Application Ser. No. 60/912,618, filed Apr. 18, 2007, and entitled "Multi-Moduled Nanoparticle-Structured Sensing Array and Pattern Recognition Device for Detection of Acetone in Breath." The content of each of these applications is hereby incorporated by reference in its entirety.

STATEMENT REGARDING FEDERALLY SPONSORED RESEARCH OR DEVELOPMENT

This invention was made with government support under Contract No. CHE0349040 and Contract No. CHE0848701 awarded by the National Science Foundation. The government has certain rights in this invention.

BACKGROUND

1. Technical Field

The present invention relates to multi-moduled nanoparticle-structured sensor arrays on flexible substrates. The invention further relates to methods for fabricating nanoparticle-structured sensor arrays on flexible substrates. The invention also relates to methods for chemical and biological sensing using flexible thin-film based sensors.

2. Description of Related Art

Organic monolayer-capped metal nanoparticles can be used as chemical sensing nanomaterials for chemiresistor and piezoelectric sensors on rigid substrates. In particular, molecularly-mediated thin film assemblies (TFA) of nanoparticles via covalent bonding or hydrogen-bonding of mediator (or linking) molecules can be used to construct chemiresistive sensing arrays on rigid glass substrates. The combination of the organic monolayer shells, the nanocrystal cores, and the molecular linkers for constructing sensing array materials enables the ability to tune the composition, functionality, and interparticle spatial properties of the sensor for enhancing sensitivity, selectivity, detection limit and response time. In employing nanostructured thin film materials for the design of chemiresistive sensing arrays, one can use the correlation between the electrical conductivity and the nanostructural parameters including particle size, interparticle distance, and dielectric constant of the interparticle medium. These parameters determine the activation energy in a thermally-activated conduction path, and thus have an impact on the electrical signal amplification in sensing applications. Recently, sensor devices have begun to be fabricated on flexible, e.g., organic light-emitting diodes. In comparison with conventional silicon, glass or ceramic technology, some of the advantages of flexible sensor devices include simplified processing, low-cost manufacturing, and increased flexibility for their integration in wraps, lightweight electronics packaging platform, and conformal adaptability in various complex or special sensing environment.

Currently, a variety of transducers are available commercially or in research labs to detect volatile organic compounds (VOCs), chemical warfare or toxic agents, e.g., ion mobility spectrometers, surface acoustic devices, mass spectrometers, antibody-based technology with optical reporters, gas chromatography and mass spectroscopy, fluorescence-based sensor array, etc. The sensitivity, selectivity and response speed of some systems, are however limited, especially in monitoring applications. Most commercial gas sensors use semiconductor materials (e.g., $SnO_2$) due to their high sensitivity and simple electronics. The main drawbacks include the lack of selectivity, poor long-term stability, and high temperature requirement.

There is therefore a need in the art for chemiresistor sensors comprising nanoparticle-structured sensing materials on microelectrodes patterned on flexible substrates. There is also a need in the art for chemiresistor sensors that are more selective and stable and that require lower temperatures to operate than existing sensors. There is also a need in the art for methods of fabricating sensors that lower fabrication costs for individual sensors, by reducing the cost of integrating the array onto a single substrate, and by eliminating the sensor-to-processor attach cost. There is also a need in the art for methods for cost-effectively fabricating large-area and high-performance flexible sensor devices.

Citation or identification of any reference in this application shall not be considered an admission that such reference is available as prior art to the present invention.

SUMMARY

A flexible chemiresistor (CR) module for sensing a molecule of interest is provided. In one embodiment the flexible chemiresistor (CR) module comprises: a flexible substrate; and a thin film nanoparticle assembly assembled on the flexible substrate, said thin film nanoparticle assembly comprising: metal or metal alloy core, ligand-capped nanoparticles, and molecular linkers connecting the nanoparticles.

In one embodiment, the flexible substrate is polyethylene terephthalate (PET), polyethylene naphthalate (PEN) or polyimide (PI).

In another embodiment, core material of the metal or metal alloy core is selected from the group consisting of gold, silver, platinum, iron oxide, gold-silver alloy, gold-platinum alloy, gold-copper alloy, or mixtures thereof.

In another embodiment, the thin film nanoparticle assembly has a particle radius (r), of 1 to 50 nm.

In another embodiment, the thin film nanoparticle assembly has an interparticle spacing ($\delta$) of 0.5 to 5 nm.

In another embodiment, the thin film nanoparticle assembly has an interparticle dielectric constant ($\in$) of 1 to 80.

In another embodiment, the module has a high tolerance toward repeated bending or wrapping.

In another embodiment, the molecule of interest is a volatile organic compound (VOC) selected from the group consisting of acetone, toluene, benzene hexane, heptane, octane, iso-octane, cyclohexane, chloroform, tetrahydrofuran, ethyl acetate, methanol, ethanol, isopropanol, butanol, nitrobenzene and xylenes.

In another embodiment, the VOC is acetone.

In another embodiment, the molecular linkers are selected from the group consisting of $\alpha,\omega$-alkyldithiols, $\alpha,\omega$-dicarboxylic acids, mercaptocarboxylic acids, and combinations thereof.

In another embodiment, the molecular linkers are α,ω-alkyldithiols.

In another embodiment, the α,ω-alkyldithiol is HS—$(CH_2)_n$—SH, with n being 3-10.

In another embodiment, the molecular linkers are α,ω-dicarboxylic acids.

In another embodiment, the α,ω-dicarboxylic acid is $HO_2C$—$(CH_2)_n$—$CO_2H$, with n being 2 to 16.

In another embodiment, the molecular linkers are mercaptocarboxylic acids.

In another embodiment, the mercaptocarboxylic acids is HS—$(CH_2)_n$—$CO_2H$, with n being 2 to 18.

In another embodiment, the metal or metal alloy core, ligand-capped nanoparticles are capped with a nanoparticle capping ligand selected from the group consisting of alkanethiols, alkyl amines, alkyl alcohols, alkanoic acids, or mixtures thereof.

In another embodiment, the nanoparticle capping ligand is decanethiol.

A hand-held device is also provided comprising the flexible CR module integrated in the hand-held device.

In one embodiment, the molecule of interest is acetone.

In another embodiment, the hand-held device detects acetone in the breath stream of a mammalian subject.

A flexible chemiresistor (CR) sensor for sensing a molecule of interest is also provided. In one embodiment, the flexible CR sensor comprises a sensor platform, wherein the sensor platform comprises a flexible chemiresistor (CR) module.

In another embodiment, the flexible CR sensor comprises a plurality of different sensor platforms.

In another embodiment, the different sensor platforms differ with regard to nanoparticle capping ligands, nanoparticle cores, molecular linkers, and/or flexible substrate thickness.

In another embodiment, nanoparticle cores differ by size or material.

In another embodiment, the nanoparticle capping ligands differ by size or material.

In another embodiment, molecular linkers differ by length or chemical content.

In another embodiment, the flexible CR sensor comprises a plurality of transducers mounted on the sensor platform and operably linked to the sensor platform.

In another embodiment, the flexible CR sensor comprises an artificial neural network; and a voltage source operably linked to the artificial neural network and the plurality of transducers, wherein the artificial neural network is designed to recognize contact of the molecule of interest with the sensor platform.

In another embodiment, the transducers are quartz-crystal microbalances

In another embodiment, the transducers are interdigitated microelectrodes.

In another embodiment, the flexible CR sensor further comprises a microcontroller operably linked to the transducers.

In another embodiment, the flexible CR sensor further comprises a circuit board operably linked to the transducers.

In another embodiment, the flexible CR sensor further comprising software for data processing or pattern recognition.

In another embodiment, the neural network is trained to distinguish contact of the molecule of interest with the sensor platform from contact of other agents with the sensor platform.

In another embodiment, the neural network is trained to quantitate concentration of the molecule of interest contacting the sensor platform.

A hand-held device is also provided wherein the flexible CR sensor is integrated in the hand-held device.

In one embodiment, the hand-held device detects a molecule of interest. In a specific embodiment, the molecule of interest is a VOC, e.g., acetone.

In another embodiment, the hand-held device detects acetone in the exhaled breath of a mammalian subject.

A method for detecting a molecule of interest in a fluid is provided. In one embodiment, the method comprises the steps of providing a fluid; and contacting the fluid with the flexible CR module or the flexible CR sensor under conditions effective to detect the molecule of interest in the fluid.

In one embodiment, the fluid is a gas.

In another embodiment, the fluid is a breath stream of a mammalian subject.

A method for preparing a thin film nanoparticle assembly on a flexible substrate is also provided.

In one embodiment, the thin film nanoparticle assembly comprises metal or metal alloy core, ligand-capped nanoparticles and molecular linkers connecting the nanoparticles.

In another embodiment, the method comprises the steps of providing a flexible substrate; and assembling the nanoparticles on the flexible substrate, wherein the assembling step comprises the step of molecularly-mediated interparticle linking the nanoparticles, the step of stamping the nanoparticles, or the step of drop-casting the nanoparticles.

In another embodiment, the assembling step comprises the step of stamping the nanoparticles, said method further comprising the step of preparing a nanoparticle assembly ink for stamping prior to the step of stamping the nanoparticles.

In another embodiment, the stamping step comprises transferring the ink using a poly(dimethylsiloxane) (PDMS) stamp onto desired areas of the flexible substrate.

In another embodiment, the method further comprises patterning microelectrodes on the flexible substrate. In a specific embodiment, the flexible substrate is polyethylene terephthalate (PET), polyethylene naphthalate (PEN) or polyimide (PI).

BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1A depicts an exemplary flexible chemiresistor module;

FIG. 1B depicts the exemplary flexible chemiresistor module of FIG. 1A in various states of actuation or bending;

FIG. 2A depicts photos showing exemplary micro-fabricated chemiresistor arrays on polyethylene terephthalate (PET) substrates of two different shapes and, in the insert, a detailed feature of interdigitated microelectrodes;

FIG. 2B depicts photos showing exemplary nanoparticles thin film coated sensor array and, in particular, an example (a) a nanoparticle thin film assembly on the entire array device and an example (b) of four different nanoparticle thin films assembled on four of the active interdigitated microelectrode areas, wherein the insert illustrates an AFM image of the nanoparticle thin film pattern on Au/mica substrate produced by μ-contact printing;

FIG. 3A depicts an illustration (I) of the interparticle spatial structures for 11-mercaptoundecanoic acid (MUA)-Au$_{(small-size)}$ and MUA-Au$_{(large-size)}$, DT-Au$_{(small-size)}$, and DT-Au$_{(large-size)}$ films and a TEM image (II) for a thin film of MUA-Au$_{(6nm)}$;

FIG. 3B depicts a plot showing relative volume percentages of the particle cores (e.g., the filled circles representing d=1.2 nm, d=1.4 nm, d=1.5 nm) and organic shells (e.g., filled triangles representing d=1.2 nm, d=1.4 nm, d=1.5 nm as a function of the particle size for the molecularly-mediated thin films as illustrated in FIG. 3A;

FIG. 5A depicts a plot showing the sensor response profiles for the sensing film of MUA-Au$_{2nm}$ in response to vapors of benzene (a), hexane (b), and water (c);

FIG. 5B depicts a plot showing the response sensitivities for the sensing film of MUA-Au$_{2nm}$ in response to vapors of benzene (a), hexane (b), and water (c);

FIG. 6A depicts a plot showing the sensor response profiles for the sensing film of MUA-Au$_{7nm}$ in response to vapors of benzene (a), hexane (b), and water (c);

FIG. 6B depicts a plot showing the response sensitivities for the sensing film of MUA-Au$_{7nm}$ in response to vapors of benzene (a), hexane (b), and water (c);

FIG. 7A depicts a plot showing the sensor response profiles or the sensing film of DT-Au$_{7nm}$ in response to vapors of benzene (a), hexane (b), and water (c);

FIG. 7B depicts a plot showing the response sensitivities for the sensing film of DT-Au$_{7nm}$ in response to vapors of benzene (a), hexane (b), and water (c);

FIG. 8A depicts a two-dimensional (2D) plot showing PCA scores for the sensor array responses for sensing films comprising MUA-Au$_{2nm}$, MUA-Au$_{7nm}$, and DT-Au$_{7nm}$ in response to test vapors comprising benzene (Bz), water (Wa), hexane (Hx), and toluene (Tl);

FIG. 8B depicts a three-dimensional (3D) plot showing PCA score for the sensor array responses for sensing films comprising MUA-Au$_{2nm}$, MUA-Au$_{7nm}$, and DT-Au$_{7nm}$ in response to test vapors comprising benzene (Bz), water (Wa), hexane (Hx), and toluene (Tl);

FIG. 11A depicts an exemplary printed circuit board (PCB) design with functional block;

FIG. 11B depicts a flow diagram of exemplary software for data processing;

FIG. 14A depicts a plot of sensor response profiles for channels 1 and 6 in detection of acetone (AC), water (H$_2$O), and their mixture (AC+H$_2$O);

FIG. 14B depicts a plot of PCA scores in the PC1-PC2 plane for mixture (blue), water (pink) and acetone (green), wherein PC1 is about 97.3% and PC2 is about 2.5%;

FIG. 15A depicts a plot of response profile from one sensor element of the 6-element array (PDT-Au$_{5nm}$ (Ch6)) in response to several vapor samples comprising air (blank), acetone (AC, 210 ppm in air), human breath (HB), and HB spiked with AC (210 ppm), wherein the top line is HB, the next lower line is HB+Acetone, the next lower line is acetone, and the bottom line is air;

FIG. 15B depicts a plot of the response profiles obtained under two different squeeze-pumping methods, wherein the top curve represents a single large squeeze and release cycle and the bottom curve represents multiple small squeeze and release cycles;

FIG. 16A depicts a plot of PCA scores for results obtained with HB samples from for two healthy persons (HB1 and HB2), wherein the data represents the PC1-PC2 plane for 4-element array (BDT-Au$_{2nm}$ (Ch1), PDT-Au$_{2nm}$ (Ch2), PrDT-Au$_{2nm}$ (Ch3), and PDT-Au$_{5nm}$ (Ch6)) in response to several vapor samples comprising air (blank), acetone (AC, 210 ppm in air), human breath (HB), and HB spiked with AC (210 ppm);

FIG. 16B depicts a plot of PCA scores for results obtained with HB samples from the same two healthy persons (HB1 and HB2), wherein the data represents the PC1-PC2 plane for 4-element array (BDT-Au$_{2nm}$ (Ch1), PDT-Au$_{2nm}$ (Ch2), PrDT-Au$_{2nm}$ (Ch3), and PDT-Au$_{5nm}$ (Ch6)) in response to several vapor samples: air (blank), acetone (AC, 210 ppm in air), human breath (HB), and HB spiked with AC (210 ppm), and wherein the arrows show the decrease of concentration;

FIG. 18A depicts a photo of a flexible sensor device showing bending and the orientations of interdigitated microelectrode patterns in the flexible sensor device relative to the device bending direction including "vertical (upper-left corner) and "horizontal" (upper-right corner).

FIG. 18B depicts an AFM image of NDT-Au$_{2mm}$ thin film;

FIG. 18C depicts an illustration of the two types of bending, wherein F identifies flat, CC identifies concave (compressive strain), and CV identifies convex (tensile strain);

FIG. 18D depicts a plot that describes the definition of the radius of curvature ($R_b$) for the wrapping;

FIG. 19A depicts a plot of $\Delta R/R_1$ vs. $\in_{strain}$, wherein $\in=10$;

FIG. 19B depicts a plot of $\Delta R/R_1$ vs. radius of curvature for the bending ($R_b$), wherein r=1.0 mm, d$_1$=1.6 nm, and $\beta$=4.0 nm$^{-1}$, for both convex (tensile strain) and concave (compressive strain) wrapping directions, and wherein the dashed lines represent data for $R_{b1}$-10 mm, $R_{b2}$=5 mm, and $R_{b3}$=3 mm;

FIG. 20A depicts a plot of the response profile for NDT-Au$_{2nm}$ film in response to hexane (a) and water (b) vapors, wherein the response of NDT-Au$_{2nm}$ to water was multiplied by a factor of 10, and wherein the insert depicts sensitivity for NDT-Au$_{2nm}$ film: 2.5×10$^{-5}$ (ppm$^{-1}$) (a) and 1.2×10$^{-6}$ (ppm$^{-1}$) (b);

FIG. 20B depicts a plot of the response profile for MUA-Au$_{2nm}$ film in response to hexane (a) and water (b) vapors, and wherein the insert depicts sensitivity for MUA-Au$_{2nm}$ film: $1.1\times10^{-4}$ (ppm$^{-1}$) (a) and $-3.5\times10^{-5}$ (ppm$^{-1}$) (b);

FIG. 21A depicts a plot of the differential resistance change, $\Delta R/R$, of a device coated with NDT-Au$_{2nm}$ film in response to repetitive flat vs. bending cycles for a device ($R_b$=10 mm) with the microelectrode pattern in the "vertical" orientation under nitrogen (dry);

FIG. 21B depicts a plot of the differential resistance change, $\Delta R/R$, of a device coated with NDT-Au$_{2nm}$ film in response to repetitive flat vs. bending cycles for a device ($R_b$=10 mm) with the microelectrode pattern in the "vertical" orientation under water (RH=86%);

FIG. 21C depicts a plot of the differential resistance change, $\Delta R/R$, of a device coated with NDT-Au$_{2nm}$ film in response to repetitive flat vs. bending cycles for a device ($R_b$=10 mm) with the microelectrode pattern in the "vertical" orientation under hexane (~4100 ppm);

FIG. 21D depicts a plot of the differential resistance change, $\Delta R/R$, of a device coated with NDT-Au$_{2nm}$ film in response to repetitive flat vs. bending cycles for a device ($R_b$=10 mm) with the microelectrode pattern in the "vertical" orientation under ethanol (~1600 ppm);

FIG. 24A depicts a plot of the average $\Delta R/R$ values in response to convex and concave bending for two devices coated with NDT-Au$_{2nm}$ films ($R_b$=5 mm) but with the microelectrode patterns in two different orientatins with respect to the bending direction, "horizontal" under different gas/vapor molecules;

FIG. 24B depicts a plot of the average $\Delta R/R$ values in response to convex and concave bending for two devices coated with NDT-Au$_{2nm}$ films ($R_b$=5 mm) but with the microelectrode patterns in two different orientations with respect to the bending direction, "vertical," under different gas/vapor molecules;

FIG. 25A depicts illustrations of possible changes in interparticle distances for a microelectrode pattern on a flexible device without strain;

FIG. 25B possible changes in interparticle distances for a microelectrode pattern on a flexible device with strain the interparticle spatial properties may change differently for the two orientations of the microelectrode pattern with respect to device bending in the horizontal direction; and FIG. 25C possible changes in interparticle distances for a microelectrode pattern on a flexible device with strain the interparticle spatial properties may change differently for the two orientations of the microelectrode pattern with respect to device bending in the vertical directions.

DETAILED DESCRIPTION

Figure 4:
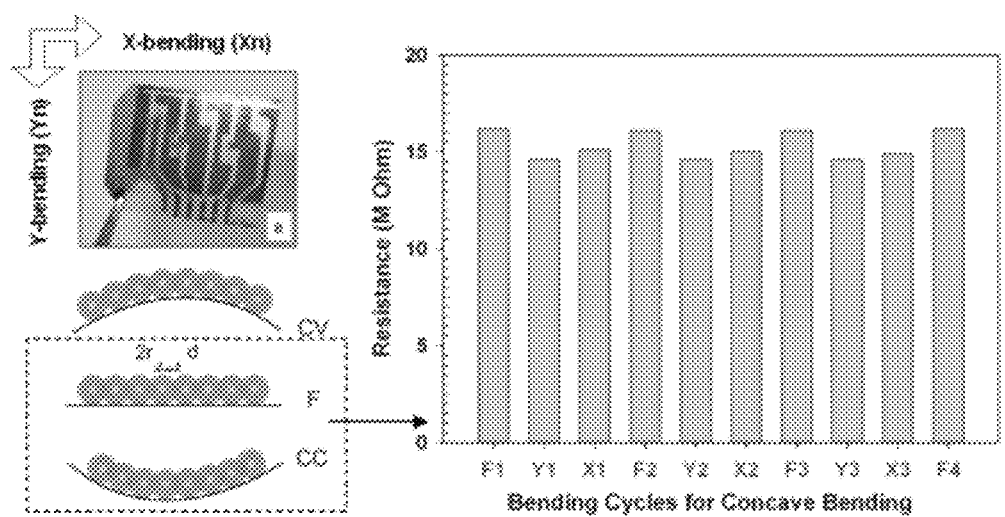
FIG. 4 depicts a plot of data showing the resistance change for an MUA-Au$_{2nm}$/CR/PET device upon bending of the flexible device along the indicated X-bending (Xn) and Y-bending (Yn) directions, wherein F identifies flat, CC identifies concave, CV identifies convex, and n identifies number of cycles.

FIG. 1A depicts an exemplary flexible chemiresistor (CR) module 100 (also "module 100") that can sense a molecule of interest. The module 100 comprises a flexible substrate 102 and a thin film nanoparticle assembly 104, which in the present example includes a plurality of microelectrodes 106 and a plurality of metal or alloy core, ligand-capped nanoparticles 108 (also "nanoparticles 108") that are disposed on or otherwise supported by the flexible substrate 102. The nanoparticles 108 comprise a core 110, which can comprise metal and/or metal-alloys. As shown in the detail, a plurality of nanoparticle capping ligands 112 connect adjacent ones of the nano particles 108.

The structure of the module 100 is discussed in various levels of detail in the discussion that follows below. Generally embodiments of the module 100 provide a robust sensing device, which can sense a wide array of fluidic (e.g., gasses) materials. As shown in FIG. 1B, the module 100 can be manipulated in various states of bending, while maintaining its ability to respond to the various gases in the environment surrounding the module 100. In one embodiment, the module 100 can be bent or wrapped for conformal adaptivity, e.g., for application to a part of the body, about an object having curved surfaces, and the like. Further adaptations of the module 100 can be tuned to withstand various levels, degrees, and directions of bending and wrapping.

A flexible chemiresistor (CR) sensor for sensing a molecule of interest is provided. In one embodiment, the flexible CR sensor (also referred to herein as a flexible CR device) comprises a flexible chemiresistor (CR) module.

A flexible CR module is also provided. The flexible CR module can comprise a flexible substrate and a thin film nanoparticle assembly assembled on the flexible substrate. The thin film nanoparticle assembly comprises metal or metal alloy core, ligand-capped nanoparticles and molecular linkers connecting the nanoparticles.

The flexible CR sensor can comprise nanostructured sensing arrays coupled with chemiresistive (CR) (e.g., interdigitated microelectrode (IME)) or piezoelectric (e.g., quartz-crystal microbalance (QCM)) transducer sensing (or sensor) platforms. The detection mechanism is based on vapor-nanostructure interactions that induce changes in electronic conductivity or in mass loading with unique response signatures that can be identified by pattern recognition technique. The electronic conduction and framework affinity display electronic or mass responses that are highly sensitive owing to fine-tunability of size, shape, composition, and spatial properties, large surface area-to-volume ratio, multidentate ligating specificity, and molecularly-defined nanoporosity.

In various embodiments, the flexible CR sensor can comprise sensing nanomaterials, transducers, microelectronics, microprocessor, battery-based power supply, and software for data processing and pattern recognition. The coupling of flexible thin film assemblies of nanoparticles and pattern-recognition capability in an integrated chip device constitutes an important strength leading to unprecedented enhancement in sensitivity, selectivity, detection limit, and response time. In addition to the viability of charging a single electron on a single nanoparticle or hopping/tunneling electrons in a collective ensemble of nanoparticles as highly sensitive materials, there are other technical attributes that can be employed in the flexible CR sensor, including enrichment of ligands and voids in the high surface area-to-volume ratio microenvironment, non-covalent character such as hydrogen-bonding, coordination and van der Waals sites, and chemically-active nanocrystal catalytic sites for tuning selectivity. The technical attributes of the flexible CR sensor address some of the drawbacks in existing sensor technology, including high detection limit, limited selectivity, slow response, lack of portability, and high cost.

In one embodiment, the flexible CR sensor and an intelligent pattern recognition engine are incorporated in a handheld device that can detect a molecule of interest in a fluid (e.g., a liquid or gas) accurately, rapidly, and without false positives. Any sensing array nanomaterial, pattern recognition, and compact/or electronic hardware can be integrated with one another with a desired detection limit (e.g., ~10 ppb) and response speed.

In embodiments in which the flexible CR sensor is incorporated into a handheld device, the device can also comprise a conditioning circuit and a microcontroller. The microcontroller provides program instructions and controls for the sensor arrays and sensor platforms and processes detection readings from the sensor arrays and sensor platforms. The microcontroller also provides switching and current control over the sensor array and sensor platform and receives output data from the sensor array and sensor platform. The microcontroller further processes the output data from the sensor array and sensor platform and provides a readout or other indication to a user or to a data collection device. In one embodiment, the microcontroller is operably linked to a transducer or plurality of transducers.

The handheld device may also include a storage device for retaining the output data and environmental factors during sampling, including detected levels of a molecule of interest, concentration ranges, analysis criteria, and other qualitative and quantitative evaluation criteria and performance factors.

The flexible chemiresistor (CR) sensor and devices incorporating it can be used in many applications, for example, for the detection of volatile and toxic gases emitted or present in the environment or for characterization or diagnosis of the breath of a subject (e.g., a human patient). The flexible CR sensor has (1) the ability to respond to molecules of interest with high sensitivity and low detection limit, (2) the ability to differentiate molecules of interest from other chemicals in a fluid with high selectivity to minimize false positives, (3) rapid response time, (4) device portability, (5) non-invasive detection mode, and (6) cost-effectiveness of the device For clarity of disclosure, and not by way of limitation, the detailed description of the invention is divided into various subsections as set forth below.

Nanoparticles

A flexible chemiresistor (CR) sensor for sensing a molecule of interest is provided. In one embodiment the flexible CR sensor comprises a flexible chemiresistor (CR) module. A flexible CR module is also provided.

The flexible CR module can comprise a flexible substrate and a thin film nanoparticle assembly assembled on the flexible substrate. The thin film nanoparticle assembly comprises metal or metal alloy core, ligand-capped nanoparticles and molecular linkers connecting the nanoparticles. The nanoparticle radius (r) can be from 1 nm to 50 nm.

The core material of the metal or metal alloy core of the nanoparticles can be selected from the group consisting of gold, silver, platinum, iron oxide, gold-silver alloy, gold-platinum alloy, gold-copper alloy, or mixtures, compositions, derivations, and composites thereof. The nanoparticles are preferably encapsulated in a monolayer shell (see, e.g., U.S. Patent Application Publication No. US2009/0049890 filed by Zhong et al. (hereinafter, "the '890 publication")).

The metal or metal-alloy core nanoparticles are preferably 2 to 10 nm in diameter. In other embodiments, the metal or metal-alloy core nanoparticles have diameters that range from 1.0 nm to 100 nm.

Metal or metal-alloy core nanoparticles can be synthesized and encapsulated using methods known in the art. For example, gold nanoparticles of 2-nm diameter ($Au_{2nm}$) encapsulated with decanethiolate monolayer shells can be synthesized by two-phase reduction of $AuCl_4^-$ according to Brust's two-phase protocol and a synthetic modification. Gold nanoparticles with larger sizes can be synthesized by a thermally-activated processing route known in the art. The solution containing the as-synthesized $DT-Au_{2nm}$ nanoparticles from the synthesis can be heated at 150° C. to produce larger-sized Au nanoparticles. This method produces gold nanoparticles of 7.0±0.5 nm diameters ($Au_{7nm}$). Details for the morphology and size distribution of desired metal or metal-alloy core nanoparticles can be determined from previously published studies.

Examples 1, 2, and 3 hereinbelow and the '890 publication disclose methods for synthesizing, capping, and linking of nanoparticles suitable for use in the present invention.

Flexible Chemiresistor (CR) Module

The flexible chemiresistor (CR) module comprises a flexible substrate and a thin film nanoparticle assembly assembled on the flexible substrate. In one embodiment, the flexible CR module is a "plug-and-play" module, one or more of which can be operably linked to desired microelectronic hardware or data acquisition/processing/readout software.

The thin film nanoparticle assembly comprises metal or metal alloy core, ligand-capped nanoparticles and molecular linkers connecting the nanoparticles.

The thin film nanoparticle assembly preferably has an interparticle spacing ($\delta$) of 0.5 nm to 5 nm and an interparticle dielectric constant ($\in$) of 1 to 80 with respect to that for air.

In one embodiment, the molecular linkers are selected from the group consisting of α,ω-alkyldithiols, α,ω-dicarboxylic acids, mercaptocarboxylic acids, and combinations thereof.

In another embodiment, the molecular linkers are α,ω-alkyldithiols. In another embodiment, the α,ω-alkyldithiol is HS—$(CH_2)_n$—SH, with n being 3-10.

In another embodiment, the molecular linkers are α,ω-dicarboxylic acids. In another embodiment, the α,ω-dicarboxylic acid is $HO_2C$—$(CH_2)_n$—$CO_2H$, with n being 2 to 16.

In another embodiment, the molecular linkers are mercaptocarboxylic acids. In another embodiment, the mercaptocarboxylic acid is HS—$(CH_2)_n$—$CO_2H$, with n being 2 to 18.

In another embodiment, the molecular linkers differ by length or chemical content.

In another embodiment, the nanoparticle capping ligand is selected from the group consisting of alkanethiols, alkyl amines, alkyl alcohols, alkanoic acids, or mixtures thereof.

In another embodiment, the nanoparticle capping ligand is alkanethiols with different chain lengths HS—$(CH_2)_n$—$CH_3$, in which n=1 to 17.

In another embodiment, the flexible CR module comprises a plurality of transducers mounted on a sensor platform and operably linked to the sensor platform.

Sensor Platform

The flexible CR sensor can comprise a sensor (sensing) platform. In one embodiment, the sensor platform comprises one or more flexible chemiresistor (CR) modules, and can additionally comprise, in certain embodiments, microelectronic hardware, and data acquisition/processing/readout software. As will be apparent to the skilled artisan, flexible CR modules can be operably linked to the microelectronic hardware and the data acquisition/processing/readout software using standard methods known in the art.

The flexible CR sensor can comprise a single type of sensor platform or a plurality of different types of sensor platforms. The different sensor platforms can differ, for example, with regard to the nanoparticle capping ligands, the nanoparticle cores, the molecular linkers, and/or thickness of the flexible substrate (i.e., film thickness).

In one embodiment, the nanoparticle cores differ by size or material.

In another embodiment, the capping ligands differ by size or material.

In another embodiment, the molecular linkers differ by length or chemical content.

Molecules of Interest

In one embodiment, the flexible CR sensor detects molecule of interest. Molecules of interest can be, for example, any volatile organic compounds (VOCs), e.g., benzene, hexane, toluene, acetone, chemical warfare agent, and/or toxic agent known in the art.

The molecule of interest is preferably dissolved in a fluid, comprised in a fluid, or forms a fluid. The fluid can be a liquid fluid or a gaseous fluid (gas).

In one embodiment, the molecule of interest (e.g., VOC) can be a biomarker in the breath indicative of a condition, disease or disorder of interest in a subject mammal (e.g., a primate such as a human, a carnivore, an ungulate or a rodent). The condition, disease or disorder can be a metabolic or hormonal disorder.

In a specific embodiment, the VOC is acetone, which is a biomarker in the breath and can be used for detecting a diabetic condition or disorder in a mammal.

Methods for Preparing Thin Film Assemblies of Nanoparticles on Flexible Substrates Methods for fabricating flexible CR modules are provided. In one embodiment, a flexible CR module is fabricated by preparing a thin film assembly of nanoparticles on a flexible substrates.

Metal or metal alloy core, ligand-capped nanoparticles can be assembled on a flexible substrate using molecularly-mediated interparticle linking, or stamping methods. For example, NDT-linked thin films (NDT-$Au_{2nm}$) can be prepared via an "exchanging-crosslinking-precipitation" route using a $10^3$-$10^4$ ratio of NDT to Au nanoparticles.

The solvent used for assembly preferably does not affect the flexible substrates chemically or physically. Compatibility of a particular solvent with a desired flexible substrate can be determined by the skilled artisan using methods known in the art.

Thin films with metal or metal alloy core nanoparticles can be prepared via stamping methods known in the art. The nanoparticle assembly inks for stamping the thin films can be prepared by first producing 11-mercaptoundecanoic acid (MUA)-linked nanoparticle precipitates via an assembly route known in the art and then re-dispersing the precipitates in an ethanol solution.

For example, a hexane solution of mixed MUA and DT-capped gold nanoparticles at controlled concentrations, typically in the concentration range of 30 μM for $Au_{2nm}$ and 10 mM for MUA, can be maintained under stirring for overnight. A known quantity of the precipitation is then re-dispersed in ethanol solution as an ink solution (~120 μM). Before stamping, the chemiresistor devices are cleaned with water and ethanol and are also immersed into an ethanol solution of 1-octadecanethiol to form a monolayer to enhance the adhesion for stamping.

The ink is then transferred using a poly(dimethylsiloxane) (PDMS) stamp onto the desired microelectrode areas on the pretreated sensor device and dried under ambient conditions.

In another example, a thin film of nanoparticles can be prepared by the drop-cast (drop-casting) method. FIG. 16 illustrates the basic steps of the drop-cast method. A solution of the desired combination of nanoparticles and linking or capping agents can be prepared as inks with controlled or desired concentrations. A PDMS master stamp can then be used to transfer the nanoparticle ink onto the device (stamping method) or a micropipette can be used to transfer the nanoparticle ink onto the device. The inked device is then dried under a dry atmosphere.

A series of combinations of linking molecules (L), capping molecules (C), and nanoparticles (NP), including hydrogen-bonding domains/voids with hydrophobic environment, hydrophobic domains with catalytic sites, hydrophobic dense packing with multidentate ligands and ionic character, etc. can be used. In one embodiment, a two-component assembly strategy is used, where the exchanging molecules (R') form H-bonding whereas the original capping shell molecules (R) form interdigitated structures via VW interactions. Examples include:

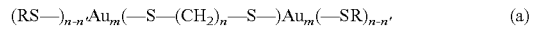
(a)

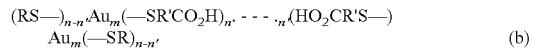
(b)

(c)

which involve interparticle covalent (a), hydrogen-bonding (b), metal-carboxylate bonding (c), and hydrophobic chain-chain interdigitation as well.

Examples of L include HS—$(CH_2)_n$—SH, $H_2N$—$(CH_2)_n$—$NH_2$, HS-$(\Phi)_n$-SH, HS—$(CH_2)_n$—$CO_2H$, $HO_2C$—$(CH_2)_n$—$CO_2H$, HS—$(CH_2)_n CH(NH_2)CO_2H$, and HS—$(CH_2)_n$—$NH_2$. Examples of C include HS—$(CH_2)_n$—$CH_3$ and functionalized thiols [—$NH_2$, —OH, —$CO_2H$]. Examples of NPs include metal, alloy, oxide, and core-shell nanoparticles (e.g., Au, Ag, AuAg, AuPt, Cu, Au/$SnO_2$, Au/$TiO_2$, etc).

The micro-contact stamping method and the drop-casting method (described above) can be used for transferring nanoparticle thin films onto the flexible array. The micro-contact stamping method can employ polydimethysiloxane (PDMS) masters of different dimensions. The composition and concentration of the nanoparticle inks can be manipulated, using standard methods, to control the thin film structure and thickness.

Interdigitated microelectrodes, e.g., copper microelectrodes, can be patterned on a flexible substrate, e.g., a thin film of polyethylene terephthalate (PET), polyethylene naphthalate (PEN) or polyimide (PI).

The flexible substrate is preferably 0.05 mm to 2 mm in thickness. In a specific embodiment, the flexible substrate is polyethylene terephthalate (PET) with a thickness of 125 μm.

PET (or PEN or PI) sheets can be cleaned using art known methods (e.g., isopropyl alcohol and oxygen plasma) before sputtering of, e.g., 5 nm Cr and 300 nm Cu films.

In one embodiment, the flexible substrate comprises one or more pairs of microelectrodes with well-defined length, width and spacing (e.g., 100-400 μm in length, 5-10 μm in width and 5-10 μm in spacing) on the flexible substrate.

The flexible substrate can be patterned by photolithography and etched using methods known in the art. Microfabrication of microelectrodes on thin films has been reported previously.

Nanoparticles can be assembled on either an entire array, using, e.g., a molecularly-mediated assembly method, or on each of the active interdigitated microelectrode areas using PDMS stamp transferring method. The thin films prepared by the latter method are reproducible, and consistent with those prepared by the molecularly-mediated thin film assembly method.

Testing Thin Film Assemblies of Nanoparticles on Flexible Chemiresistor (CR) Modules A computer-interfaced multi-channel meter (e.g., Keithley, Model 2700) can be used to measure the lateral resistance of the thin film assemblies of nanoparticles on flexible CR modules.

For example, to test the thin film assemblies of nanoparticles on flexible CR modules, they can be tested inside a Teflon chamber with tubing connections to vapor and $N_2$ sources. Testing can be conducted at room temperature, 22±1° C. $N_2$ gas (99.99%) can be used as a reference gas and as a diluent to change the vapor concentration by controlling mixing ratio. The vapor concentration can be controlled by a flow system bubbling dry $N_2$ gas through a selected vapor solvent. The gas flow can be controlled by a calibrated mass-flow controller (e.g., Aalborg AFC-2600). The flow rates of the vapor stream can be varied, e.g., between 3 and 99 mL/min, with $N_2$ added to a total of 100 mL/min. The vapor generating system can be a multi-channel module linked to different vapor sources.

In one embodiment, the test chamber is purged with pure nitrogen to establish the baseline before introducing analyte vapor. The vapor concentration in the unit of ppm (M) was determined from the partial vapor pressure and the mixing ratio of vapor and $N_2$ flows, which can be converted to ppm (V) by multiplying a factor of 24.5. Detailed measurement protocols are known in the art.

The measured resistance ($R_\Omega$) is related to the lateral conductivity (σ) of the film. ΔR is the difference of the maximum and minimum values of the resistance in response to vapor exposure, and $R_i$ is the initial resistance of the film. The response sensitivity is determined from the relative differential resistance change, $\Delta R/R_i$, versus vapor concentration, C (ppm).

Characteristics of Chemiresistive (CR) Sensors

Flexible CR sensors with different microelectrode parameters and comprising different types of flexible CR modules (e.g., having different sensitivities) can be evaluated for their general electrical and chemiresistor characteristics using methods known in the art.

Thin film flexible substrates can display different colors depending on the particle size and interparticle linking molecules or distance. The colors can be seen by the naked eye of the observer. Quantitatively, the color can be determined, and the thin film characterized, using a UV-visible spectrometer and methods known in the art.

On the basis of the interparticle spatial structures and properties shown in FIG. 2A, and the relative core-shell composition revealed in previously published studies, the flexible CR modules comprising, e.g., MUA-linked thin film assemblies can be distinguished from unlinked assemblies of DT-capped gold nanoparticles by several criteria.

First, there is difference associated with the interparticle interactions. The presence of hydrogen bonding in combination with interdigitation of the alkyl chains creates a mediator-template structure for the interparticle structure of the MUA-linked assemblies. In contrast to the relatively strong mediator-templating interparticle interactions, there is only weak interparticle interaction due to the interdigitation of alkyl chains for the unlinked assemblies of DT-capped nanoparticles. This difference can be observed in the solubility difference for these films. For example, an unlinked DT-$Au_{2nm}$ film can be dissolved in hexane solvent. The MUA-linked DT-$Au_{2nm}$ film is insoluble in hexane solvent, but can be dissolved in the presence of more polar solvent such as ethanol.

Second, there is a significant difference in relative volume percentages of metal versus organic components in terms of the particle cores and the organic capping/linking shells in these thin film assemblies as a function of particle size. As shown in FIG. 3B, while the relative percentage of the particle cores (filled circles) increases with the particle size, the relative percentage of the organic capping/linking shells (filled triangles) decreases with the particle size. It is clear that the assemblies of the 2-nm sized particles have a shell-to-core ratio of ~4 whereas that for the 7-nm particles is less than 1. Such difference can be confirmed by thermogravimetric analysis of metal to organic ratios for the nanoparticles with different sizes.

Third, the size difference leads to a major difference in the relative composition of linking versus capping molecules in the organic shells between the different sized particles. For example, as shown in Table 1 below, the extent of MUA-DT exchange has been found to be about 8% for $Au_{6nm}$ particles and ~46% for $Au_{2nm}$ particles. According to this trend, the MUA linked $Au_{7nm}$ film is expected to exhibit an even lower extent of exchange. This type of difference leads to differences for these thin films in terms of chemical and physical characteristics of the overall nanostructure. For example, the interparticle hydrogen-bonding and hydrophobicity properties have been shown to play an important role in the regulating the adsorption and fluxes of molecules and ionic species across the nanostructured thin film interfaces.

TABLE 1

| Film | Particle size (nm) | % wt of organic shell[a] | MUA Exchange Rate[b] | Resistance (MΩ) |
|---|---|---|---|---|
| NDT-$Au_{2\,nm}$ | 2 | 20.7% | 0 | 6.1 |
| MUA-$Au_{2\,nm}$ | 2 | 20.7% | 46% | 13.8 |
| MUA-$Au_{7\,nm}$ | 7 | 5.9% | 8%< | 0.81 |
| DT-$Au_{7\,nm}$ | 7 | 5.9% | 0 | 17.7 |
| DT-$Au_{2\,nm}$ | 2 | 20.7% | 0 | ~350 |

For the flexible CR sensors provided herein, the interparticle nanostructural differences lead to significant differences in electrical conductivity of the thin film assemblies, which has been shown to be highly dependent on the relative metal core vs. organic linking/capping shell structures. This dependence is reflected by the initial resistance values of the nanostructured thin films (Table 1). The initial resistance of MUA-$Au_{2nm}$ films is larger than that from MUA-$Au_{7nm}$ films, which is due to the activation energy for the thin film of the 2-nm sized particles is greater than that for the 7-nm sized particles.

The initial resistance of NDT-$Au_{2nm}$ films is smaller than that from MUA-$Au_{2nm}$ film and other films. The initial resistance of MUA-$Au_{7nm}$ films is smaller than that from DT-$Au_{2nm}$. The differences of the initial conductivities reflect the differences of a combination of several parameters including interparticle distances and dielectric medium constants. The average resistance for cast DT-$Au_{2nm}$ films is about 350 MΩ.

The electrical properties are also dependent on the design parameters of the interdigitated microelectrodes for the chemiresistor on the flexible substrate. Table 2 below lists a representative set of design parameters in terms of finger space (S), finger width (W), and finger length (L), as well as the resistance values for MUA-$Au_{2nm}$ thin films. The measured initial resistance (R) is related to the lateral conductivity (σ) of the film (σ=(1/R)(S/dL(N−1)), wherein S is the finger space, L is the finger length of the microelectrodes, N is the number of microelectrode pairs, and d is the film thickness. The thickness of the film can be controlled by assembly time and interparticle distance.

TABLE 2

| Design # | W (μm) | S (μm) | L (μm) | Initial Resistance R (MΩ) |
|---|---|---|---|---|
| 1 | 5 | 5 | 100 | 8 |
| 2 | 5 | 10 | 100 | 19 |
| 3 | 10 | 5 | 100 | 11 |
| 4 | 10 | 5 | 300 | 9 |
| 5 | 10 | 10 | 100 | 26 |
| 6 | 10 | 10 | 400 | 20 |

The initial resistance (R) increases with increasing finger space (S) for MUA-$Au_{2nm}$ films due to increase of W and decrease of the number pairs of electrode N in the equation for lateral conductivity (σ). The initial resistance (R) decreases with increasing the number pairs of electrodes by shrinking the finger width in a same total height of fingers. Finger space has significant effects on the thin film resistance properties. Flexible CR modules with smaller S exhibit smaller initial resistance value than those with larger S. This finding is qualitatively consistent with the expectation based on thin film conductivity. In addition, finger length (L) plays an important role in thin film resistance properties. By comparing flexible CR modules with the same finger space but different finger length, it is found that those with longer L have smaller initial resistance values. There is a relatively insignificant effect of the finger width (W) on the thin film resistance properties.

One property of the flexible CR devices is the viability of high tolerance toward repeated bending or wrapping. High tolerance towards repeated bending or wrapping can be determined using methods known in the art. The change of the resistance in response to bending of the device from two different directions (in each direction the approximate diameter for the bent circle is about 0.5 cm) can be measured. A typical set of testing results showing the resistance change for the MUA-$Au_{2nm}$ thin film assembly upon bending of the flexible device along the indicated directions is shown in FIG. 4.

Bending decreases the resistance by about 10% upon concave bending along the two indicated directions. Bending may create a better electrical continuity between the assembled nanoparticles and the electrode fingers. However, when the flexible CR device is allowed to return to a flat position, the resistance will recover, indicating that the film on the flexible substrate is quite stable and has good adhesion on the PET substrate.

The relative change in resistance or conductivity of the nanostructured thin films can be further characterized in terms of concave or convex wrapping of the TFA/CR/PET device. The electrical conductivity of the thin films can be described by a thermally-activated conduction path as shown in Equation (1) below:

$$\sigma = \sigma_0 \exp(-\beta d)\exp\left[-\frac{0.5e^2}{4\pi\varepsilon\varepsilon_0 RT}\left(\frac{1}{r} - \frac{1}{r+d}\right)\right] \quad (1)$$

wherein e=1.6×10$^{-19}$ C, $\varepsilon_0$=8.854×10$^{-12}$ F/m, R=1.38×10$^{-23}$ J/K, T=300 K, and r and d represent particle radius and interparticle spacing (nm), respectively. The interparticle distance can change as a result of the wrapping.

Response Characteristics of Chemiresistive (CR) Sensors

There is a correlation of the response characteristics of nanostructured thin film assemblies on the flexible substrates with the nanostructural parameters and device design parameters. This correlation builds upon on the dependence of the overall electronic conduction (electron hopping and/or electron tunneling) on the nanostructural parameters such as particle core radius (r), interparticle distance (d), and dielectric constant of interparticle medium (∈). Equation (1) can be written in terms of activation energy as shown in Equation (2a) and (2b) below:

$$\sigma = \sigma_0 \exp\left(-\frac{E_a}{RT}\right) \quad (2a)$$

$$E_a = 0.5e^2 \frac{r^{-1} - (r+d)^{-1}}{4\pi\varepsilon\varepsilon_0} \quad (2b)$$

Table 3 provides information for assessing the correlation between the sensor response sensitivities and the thin film nanostructural parameters in terms of r, d, and ∈ (e.g., as a comparison of response sensitivities for MUA-$Au_{2nm}$, MUA-$Au_{7nm}$, and DT-$Au_{7nm}$ films on PET substrates). For NDT-$Au_{2nm}$ and MUA-$Au_{2nm}$ films, the combination of the small particle size and the relatively large interparticle spacing leads to a high percentage of organics, or a high percentage of MUA (for MUA-$Au_{2nm}$ film). Such films have a relatively low electrical conductivity. For vapors that are hydrophobic (Bz, Hx, and Tl) and have small ∈ values, the change in interparticle spacing (d) upon the sorption of these vapors in the film is dominant. A positive response characteristic is thus observed.

TABLE 3

| | Response sensitivity[c] (ppm$^{-1}$) × 10$^4$ | | | |
|---|---|---|---|---|
| Sensing films | Hx | Bz | Tl | Wa |
| NDT-$Au_{2\,nm}$ | 0.54 | 0.95 | 3.03 | — |
| MUA-$Au_{2\,nm}$ | 0.59 | 1.15 | 2.78 | −1.84 |
| MUA-$Au_{7\,nm}$ | 0.65 | 1.73 | 2.65 | 0.65 |
| DT-$Au_{7\,nm}$ | 5.28 | 4.53 | 5.49 | 0.32 | wherein the response sensitivity is given in the unit of ppm (M), which can be converted to the unit of ppm (V) by dividing the value by a factor of 24.5.

From this comparison, it can be seen that the increase in particle size (i.e., MUA-Au$_{7nm}$) leads to a lower percentage for both organics and MUA, and thus a higher electrical conductivity. The positive response characteristic remains unchanged for vapors such as Bz, Hx, and Tl because the change in interparticle spacing (d) upon the sorption of these vapors in the film is still dominant. However, a slightly-larger positive response is observed in the case of Bz and Hx, which reflects the change in conductivity as a result of the increased particle size.

Neural Networks, Pattern Recognition, and Transducers

Neural networks, cluster analysis, principal component analysis techniques, and other artificial intelligence systems may be coupled with the handheld device or otherwise implemented within the handheld device to further train the sensor array, sensor platform, and microcontroller and to provide a quantitative and qualitative indication of sampled acetone concentrations.

The conditioning circuit may include filter networks and circuitry to modify the sensor array and sensor platform outputs to meet the operational requirements of the handheld device. The conditioning circuit may include noise reduction circuitry, phase equalization components, level stability circuits, frequency response correction circuitry, circuitry to correct impedance discontinuities, and other conditioning circuitry.

In one embodiment, the flexible CR sensor comprises an artificial neural network, and a voltage source operably linked to the artificial neural network and the plurality of transducers, wherein the artificial neural network is designed to recognize contact of the molecule of interest with the sensor platform.

In another embodiment, the transducers are quartz-crystal microbalances.

In another embodiment, the transducers are interdigitated microelectrodes.

In another embodiment, the flexible CR sensor further comprises a micro controller operably linked to the transducers.

In another embodiment, the flexible CR sensor further comprises a circuit board operably linked to the transducers.

While flexible thin film assemblies of metal and metal-alloy core nanoparticles using alkyl dithiols (ADTs) and dicarboxylic acids (DCAs) with different alkyl chain length (m, i.e., number of methylenes in the alkyl chain) are different in terms of binding properties and nanoparticle composition, their common property of tunable alkyl chain length can be used for assessing the correlation between sensing properties and interparticle spatial parameters. Flexible thin film based flexible CR sensors can be assembled on interdigitated microelectrode (IME) for the detection of molecules of interest. Coupling of sensor array data output with pattern recognition techniques can be used to delineate the interparticle spatial properties for constructing nano structured sensing arrays.

The flexible CR sensor can further comprises a neural network that is trained to quantitate concentration of the molecule of interest contacting the sensor platform.

In another embodiment, the neural network can be trained to distinguish contact of the molecule of interest with the sensor platform from contact of other agents with the sensor platform.

The '890 publication discloses methods for neural network training and pattern recognition suitable for use in the invention, and is incorporated herein by reference in its entirety.

There are many known approaches to pattern recognition with sensor arrays, including, Artificial Neural Networks (ANNs), Cluster Analysis (CA), and Principal Component Analysis (PCA) techniques. Among these methods, ANNs are universally recognized as one of the most effective approaches. However, the current ANNs applications in sensor array only involve single ANN module/architecture, which is very difficult to simultaneously obtain the satisfying correct identification rates for multiple molecules of interest.

The flexible CR sensor can use a more sophisticated multi-module ANNs approach with each module dedicated to a sub group/class of molecules of interest. Each specific module may have different sensing signals as inputs, which are determined by the results of sensor optimization for each vapor subgroup. The art-known Cluster Analysis (CA) technique is used for arranging the vapors to different groups, with each group having one dedicated ANNs module to serve as specific vapor recognizer.

Cluster Analysis (CA) can be used to group the vapors for assisting the construction of multi-module ANNs. In this method, the responses from the sensor array are first processed with PCA techniques to extract the main distinguishing features for different patterns.

The PCA data obtained for different molecules of interest are then clustered into different classes based on their similarities obtained by cluster analysis techniques known in the art. Because of different separation distance scales, a set of target vapors can be grouped into different subgroups with each one having a dedicated intelligent classifier, before an individual vapor is identified. The objective of this step is to further enhance the correct recognition rate for each individual vapor. The grouping task is accomplished by cluster analysis technique with K-clustering algorithm.

CA is a statistical method for assigning sets of similar items into different groups (clusters) with meaningful structures. There are different algorithms and approaches for clustering. The K-clustering algorithm is one of the most common non-parametric partition-clustering one for exclusive test patterns which attempts to find a K-clustering with minimal MSE. In other words, its goal is to minimize dissimilarity in the items within each cluster while maximizing the value between items in different clusters. It searches for the best set of clusters centroids, and determines the structure of the partition by assigning each input vector to its nearest centroid. The centroid of a cluster is defined as the point whose value are the average values of every point in the current cluster.

The distance to the centroids is calculated based on Euclidean distance metric, which is given by Equation (3):

$$Ed_{ij} = \sqrt{\sum_{k=1}^{n} (x_{ik} - x_{jk})^2} \quad (3)$$

wherein $Ed_{ij}$ is the Euclidean distance between patterns $x_i$ and $x_j$, each with n samples.

Principle Component Analysis (PCA) is a mathematical method that converts a large number of potentially correlated variables into relatively small number of uncorrelated variables. PCA is used for variable dimension reduction (feature extraction) and clustering purpose. Sensor output profiles from the sensor array differ in response to targeted molecules of interest, therefore, pattern recognition techniques can be used to analyze the data. The analysis involves two steps: signal preprocessing and pattern recognition. In the step of signal processing, the data is first normalized by the equation $\Delta R/R_i$. After normalization, the baseline is corrected, and PCA is then employed for feature extraction and clustering purpose. Features extracted by PCA serve as the inputs to the neural network pattern recognizers. The PCA method also functions as a clustering technique in which the targeted VOCs are grouped into different clusters. In order to enhance the recognition rate, different neural network modules are applied to each cluster.

Multiple neural network modules with back propagation algorithm (BPN) can be used for pattern recognition following the data processing. The BP algorithm is based on gradient descent in an error method which minimizes the mean square error between the network's output and the desired output for all input patterns. BPN is a multi-layer feed-forward network which has one input, one output, and at least one hidden layer. Each layer is fully connected to the succeeding layer, as shown, for example, in FIG. 3. During the learning process, the input vectors and the output of each neuron are computed layer by layer. The differences between the outputs of the final layer and the desired target vectors are back-propagated to the previous layer(s), modified by the derivative of the transfer function, and the connection weights are adjusted using the Widrow-Hoff learning rule.

Based on the cluster analysis result, an intelligent classifier with multi-module (or multi-level) neural network can be constructed with each one dedicated to specific vapor group to perform vapor recognition. Each module consists of a Back Propagation Network (BPN) with its own suitable architecture. The advantage of the multi-module ANNs is to eliminate the need for accommodating all the identification knowledge for all target vapors in a single network. By using multiple networks, each network is trained for learning more specific knowledge on certain vapors. In this way, the overall correct recognition rate is enhanced by "multiple experts".

Pattern Recognition Analysis

The characteristics of flexible CR sensors can be analyzed based on principal component analysis (PCA), which assesses the potential selectivity of the flexible sensor arrays for the detection of VOCs. Using methods known in the art for analyzing sensor array responses of thin film assemblies on rigid substrates, the PCA technique can be used to analyze flexible sensor arrays with different nanoparticle thin film assemblies in response to selected VOCs. PCA analysis can extract the information from a great deal of raw data, which can be achieved by converting a large number of potentially correlated variables into relatively small number of uncorrelated variables. PCA analysis can be used to assess the selectivity of a sensor array in distinguishing different vapors through the reduction of variable dimensions (feature extraction) and classification. To establish the relation between the classification capability of the sensor array and the nanostructural parameters, data can be analyzed from sensor arrays with different combinations of the thin films. The classification capability of each array will depend on the specific combination.

One representative example of such an analysis can be illustrated by the analysis of two sets of sensor response data for a 3-film sensor array consisting of MUA-$Au_{2nm}$, MUA-$Au_{7nm}$, and DT-$Au_{7nm}$ thin films in response to four different vapors (hexane, benzene, toluene, and water). FIG. 7 shows a set of the PCA score plots for the sensor responses to hexane, benzene, toluene, and water vapors in the PC1-PC3 and PC1-PC2-PC3 plane. This set of results was obtained from the PCA analysis of the normalized responses at eight different vapor concentrations. From the PCA score plots, it was observed that there is no overlap of the normalized responses, as evidenced by the separation of the clusters in both the PC1-PC3 and PC1-PC2-PC3 planes. Therefore, each of the four vapors can be clearly identified by the selected sensor array.

The further application of the art-known discriminant analysis technique with a quadratic discriminant function to the sensor array data for classifying observations into predefined classes and determining the class of an observation based on a training data set can also be used to identify molecules of interest. In this type of data analysis, the first three principle components (PC1, PC2, PC3) are used as the classification features.

The following Examples 1, Example 2, and Example 3 are offered by way of illustration and not by way of limitation.

EXPERIMENTAL SECTION

Example 1

In one embodiment, a flexible chemiresistor sensor comprises thin film assemblies of nanoparticles on polyethylene terephthalate substrate.

The thin film assembly of metal nanoparticles on flexible chemiresistor (CR) arrays can be used to address the versatility of chemical sensor design. In this example, thin film assemblies of gold nanoparticles in size range of 2-8 nm diameters with high monodispersity (unlinked or linked by molecular mediators) were assembled on an CR array with polyethylene terephthalate (PET) substrate to demonstrate the flexible chemiresistor characteristics of the nanostructured materials. The correlation between the relative change in electrical conductivity and the change in dielectric medium constant in response to flexible wrapping of the device demonstrated the viability of manipulating the electrical responses in terms of wrapping direction.

The responses of the devices in response to volatile organic compounds (VOCs) were analyzed in terms of particle size, interparticle properties, and substrate-film interactions. For molecularly-linked films with small particle size and large interparticle spacing which is characterized by a high percentage of organics and linker molecules, the relatively-low electrical conductivity renders the change in interparticle spacing to play a dominant role in the sensor response to VOCs with small dielectric constants. The combination of a high percentage of linker molecules in the thin film assembly and a high dielectric constant for the VOCs was found to produce a negative response characteristic. In contrast, the response characteristic for the unlinked film via weak interparticle interactions was dominated by the change in interparticle spacing regardless of the percentage of organics in the nanostructure. The delineation between these factors and the sensing characteristics is useful in enabling a rationale design of the nanostructures on flexible chemiresistors.

Organic monolayer-capped metal nanoparticles can be used as chemical sensing nanomaterials for chemiresistor and piezoelectric sensors on rigid substrates. In particular, molecularly-mediated thin film assemblies (TFA) of nanoparticles via covalent bonding or hydrogen-bonding of mediator (or linking) molecules can be used to construct chemiresistive sensing arrays on rigid glass substrates. The combination of the organic monolayer shells, the nanocrystal cores, and the molecular linkers for constructing sensing array materials enables the ability to tune the composition, functionality, and interparticle spatial properties of the sensor for enhancing sensitivity, selectivity, detection limit and response time. In employing nanostructured thin film materials for the design of chemiresistive sensing arrays, one can use the correlation between the electrical conductivity and the nanostructural parameters including particle size, interparticle distance, and dielectric constant of the interparticle medium.

These parameters determine the activation energy in a thermally-activated conduction path, and thus have an impact on the electrical signal amplification in sensing applications. Recently, sensor devices have begun to be fabricated on flexible, e.g., organic light-emitting diodes. In comparison with conventional silicon, glass or ceramic technology, some of the advantages of flexible sensor devices include simplified processing, low-cost manufacturing, and increased flexibility for their integration in wraps, lightweight electronics packaging platform, and conformal adaptability in various complex or special sensing environment. There is therefore a need in the art for chemiresistor sensors with nanoparticle-structured sensing materials on microelectrodes patterned on flexible substrates. Printing the sensor array could reduce the cost by lowering the fabrication costs for individual sensors, by reducing the cost of integrating the array onto a single substrate, and by eliminating the sensor-to-processor attach cost. The utilization of roll-to-roll (R2R) manufacturing technology, a promising approach to electronic devices by using organic electronics for some or all of the components, could be used for cost-effectively fabricating large-area and high-performance flexible sensor devices.

To achieve smaller, faster, reliable and disposable chemical sensors for gas or vapor detection in a wide range of complex sensing environment, device module flexibility can be achieved by conformal adaptivity to different sensor platforms. This example demonstrates nanoparticle thin film assemblies on flexible chemiresistor sensors and arrays for the detection of volatile organic compounds (VOCs). The development of such integrated sensor array systems on flexible polymer substrates such as polyethylene terephthalate (PET), polyethylene naphthalate (PEN) or polyimide (PI) exploits the attractive features such as low-cost fabrication, lightweight electronics and packaging platforms for flexible sensor applications. The flexible sensor array technology targets a wide range of complex environment including air pollution and human breath, especially in applications that demand fast and sensitive detection under conditions such as conformal wrapping over curvilinear surfaces, high tolerance toward repeated bending, mechanical shock resistance, and special sensing environment. The integration of nanostructured thin film assemblies to the sensing interfaces on a flexible sensor device presents new opportunities to address many of the existing problems because of the unique processibility, stability, tunability, and low-cost production capability.

At the time of filing, a variety of transducers are available commercially or in research labs to detect VOCs, chemical warfare or toxic agents, e.g., ion mobility spectrometers, surface acoustic devices, mass spectrometers, antibody-based technology with optical reporters, gas chromatography and mass spectroscopy, fluorescence-based sensor array, etc. The sensitivity, selectivity, and response speed of some systems are, however, limited, especially in monitoring applications. Most commercial gas sensors use semiconductor materials (e.g., $SnO_2$) due to their high sensitivity and simple electronics. The main drawbacks include the lack of selectivity, poor long-term stability, and high temperature requirement. In contrast, the coupling of nanostructured sensing materials to the flexible sensing interfaces is expected to overcome some of the drawbacks because the analyte-nanostructure interactions induce unique interparticle electrical response signatures at ambient conditions, in addition to the added values in terms of disposability and cost-effectiveness because of the viability of R2R large-scale production on sheets of polymer substrates.

FIG. 8 illustrates the general concept of a flexible chemiresistor (CR) sensor array of patterned microelectrodes on a flexible polymer substrate as a plug-and-play module, and the nanoparticle thin film assembly on the microelectrodes of the chemiresistor as sensing materials for detection of VOCs. The patterned microelectrode arrays on the flexible polymer substrate function as the sensor devices, whereas the nanoparticle thin film assemblies function as the sensing materials in which the electrical properties are tuned by the nanostructural parameters such as particle radius (r), interparticle spacing ($\delta$), and interparticle dielectric constants ($\in$). While there have been increasing studies of flexible substrates for chemical sensor device development, relatively few reports have appeared in the area of exploring nanoparticle thin film assemblies as sensing materials on the flexible substrates. How the nanostructures of the thin film assemblies of nanoparticles on the flexible chemiresistor device operate in terms of the response characteristics to VOCs is the focus of this work. Prior studies of the nanostructured sensor properties on glass substrates have been conducted, but no information is available to assess the sensing properties of the nanostructured materials on flexible substrates. To gain such a mechanistic understanding, thin films of decanethiolate monolayer-capped gold (Au) nanoparticles of less than 10 nm diameters were assembled onto the chemiresistor array on flexible PET substrates, including molecularly-linked and unlinked (e.g., drop-cast) thin film assemblies. The response characteristics of the thin films (TFA-Au/CR/PET) in response to selected VOCs and water vapor are compared to assess the effects of the subtle differences in particle size, interparticle properties, and substrate-film interactions, which are important parameters for establishing the correlation between the response characteristics and the nanostructural properties.

Chemicals and Preparation of Nanoparticles

Hydrogen tetrachloroaurate trihydrate (99%), tetraoctylammonium bromide (99%), decanethiol (DT, 96%), sodium borohydride (99%), 1,9-nonadithiol (NDT, 95%), and 11-mercaptoundecanoic acid (MUA, 95%) were purchased from Aldrich. Solvents included hexane Hx, 99.9%), toluene (Tl, 99%), and benzene (Bz, 99.0%) from Fisher, and ethanol (99.9%) from Aldrich. Water (Wa) was purified with a Millipore Milli-Q water system.

Gold nanoparticles of 2-nm diameter ($Au_{2nm}$) encapsulated with decanethiolate monolayer shells were synthesized by two-phase reduction of $AuCl_4^-$ according to Brust's two-phase protocol and a synthetic modification. The as-synthesized gold nanoparticles ($DT-Au_{2nm}$) exhibited an average size of 2.0±0.7 nm. Gold nanoparticles with larger sizes were synthesized by a thermally-activated processing route known in the art. Briefly, the solution containing the as-synthesized $DT-Au_{2nm}$ nanoparticles from the synthesis was heated at 150° C. to produce larger-sized Au nanoparticles. Gold nanoparticles of 7.0±0.5 nm diameters ($Au_{7nm}$) produced by this method were used in this work. Details for the morphology and size distribution can be found in previous reports.

Preparation of Thin Film Assemblies of Nanoparticles on Flexible Devices.

The DT-capped Au nanoparticles were assembled on the flexible chemiresistor devices using molecularly-mediated interparticle linking, or stamping methods. For example, NDT-linked thin films ($NDT-Au_{2nm}$) were prepared via an "exchanging-crosslinking-precipitation" route using a $10^3$-$10^4$ ratio of NDT to Au nanoparticles.

The MUA-Au$_{2nm}$ and MUA-Au$_{7nm}$ thin films were prepared via stamping method. The nanoparticle assembly inks for stamping the thin films were prepared by first producing MUA-linked nanoparticle precipitates via a similar assembly route and then re-dispersing the precipitates in an ethanol solution. For example, a hexane solution of mixed MUA and DT-capped gold nanoparticles at controlled concentrations, typically in the concentration range of 30 µM for Au$_{2nm}$ and 10 mM for MUA, was kept under stirring for overnight. A known quantity of the precipitation was re-dispersed in ethanol solution as an ink solution (~120 µM). Before stamping, the chemiresistor devices were well cleaned by water and ethanol, and were also immersed into an ethanol solution of 1-octadecanethiol to form a monolayer to enhance the adhesion for stamping. The ink was then transferred using a poly (dimethylsiloxane) (PDMS) stamp onto the desired microelectrode areas on the pretreated sensor device and dried under ambient condition. For thin film of DT-capped Au$_{7nm}$, the film was prepared by drop-cast method.

Device Fabrication and Sensor Measurements

Interdigitated copper microelectrodes were patterned on polyethylene terephthalate (PET) (DuPont Tejin Films Melinex ST507) film with 125 µm thickness. The PET sheets were cleaned using isopropyl alcohol and oxygen plasma before sputtering of 5 nm Cr and 300 nm Cu films. The microelectrode devices feature 150 pairs of microelectrodes with well-defined length, width and spacing (100-400 µm in length, 5-10 µm in width and 5-10 µm in spacing) on the flexible substrates, which were patterned by photolithography facility at Center for Advanced Microelectronics Manufacturing (Binghamton University, Binghamton, N.Y.), and were etched in house. Some details for the microfabrication were reported previously.

A computer-interfaced multi-channel meter (Keithley, Model 2700) was used to measure the lateral resistance of the nanostructured thin films on the chemiresistor devices, which were housed in a Teflon chamber with tubing connections to vapor and N$_2$ sources. All experiments were performed at room temperature, 22±1° C. N$_2$ gas (99.99%, Airgas) was used as reference gas and as diluent to change vapor concentration by controlling mixing ratio. The vapor concentration was controlled by a flow system bubbling dry N$_2$ gas through a selected vapor solvent. The gas flow was controlled by a calibrated Aalborg mass-flow controller (AFC-2600). The flow rates of the vapor stream were varied between 3 and 99 mL/min, with N$_2$ added to a total of 100 mL/min. The vapor generating system consisted of multi-channel module linked to different vapor sources. The modular platform components permitted different vapor flow with minimum dead-volume and virtually no cross-contamination.

The test chamber was purged with pure nitrogen to establish the baseline before introducing analyte vapor. The vapor concentration in the unit of ppm (M) was determined from the partial vapor pressure and the mixing ratio of vapor and N$_2$ flows, which can be converted to ppm (V) by multiplying a factor of 24.5. Details of the measurement protocols were described previously. The measured resistance ($R_\Omega$) is related to the lateral conductivity ($\sigma$) of the film. $\Delta R$ is the difference of the maximum and minimum values of the resistance in response to vapor exposure, and $R_i$ is the initial resistance of the film. The response sensitivity was determined from the relative differential resistance change, $\Delta R/R_i$, versus vapor concentration, C (ppm).

Figure 9:
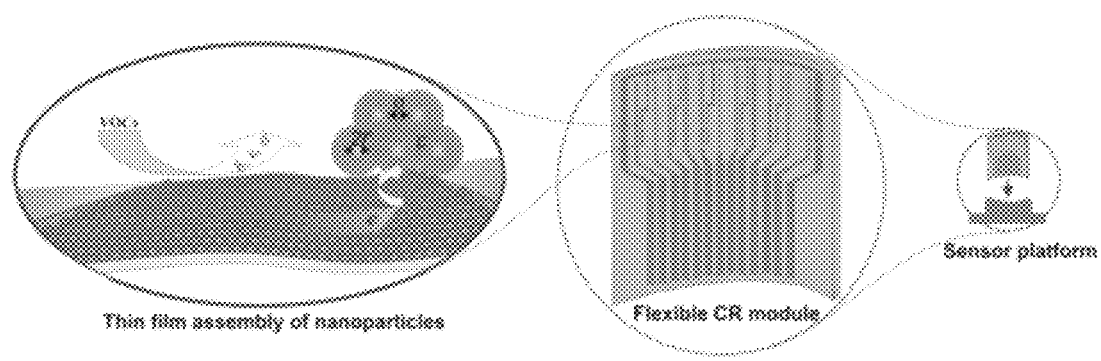
FIG. 9 depicts an exemplary flexible chemiresistor (CR) sensor array of patterned microelectrodes on a flexible polymer substrate as a plug-and-play module, wherein the nanoparticle thin film assembly on the microelectrodes of the chemiresistor as sensing materials for detection of VOCs, in which the electrical properties are tuned by the nanostructural parameters including one or more of particle radius (r), interparticle distance ($\delta$), and interparticle dielectric medium constant ($\in$)

The general electrical properties of the flexible TFA-Au/CR/PET devices with different microelectrode parameters and different nanoparticle thin films were first characterized. FIG. 9 shows a representative set of flexible CR arrays with the interdigitated copper microelectrode arrays patterned on PET substrates and TFA-Au assemblies or patterns on the flexible devices.

Thin film assemblies of decanethiolate-capped gold nanoparticles on chemiresistor/PET substrates (TFA-Au/CR/PET), which are unlinked or linked by molecular mediators (e.g., 11-mercaptoundecanoic acids or 9-nonanedithiols), were studied as a model system for assessing the chemiresistor characteristics. Thin film of nanoparticles were assembled on either the entire array by molecularly-mediated assembly method, or on each of the active interdigitated microelectrode areas using PDMS stamp transferring method, as shown for a few examples in FIG. 1B. The thin films prepared by the latter method were largely reproducible, and was basically consistent with those prepared by the molecularly-mediated thin film assembly method.

These films displayed different colors depending on the particle size, and interparticle linking molecules or distance. In general, MUA-Au$_{2nm}$ and NDT-Au$_{2nm}$ films appeared to be dark-drown whereas MUA-Au$_{7nm}$ films displayed dark-blue color. In comparison with the brown color for DT-Au$_{2nm}$ films, the DT-Au$_{7nm}$ films appeared dark-purple color.

The selection of the TFA-Au/CR/PET films for the present work were based on the interparticle structural differences in terms of linking molecules and particle sizes. In FIG. 2A, a set of idealized models is shown to illustrate the interparticle structures for the thin film assemblies of Au nanoparticles with small and large sizes which are unlinked or linked by 11-mercaptoundecanoic acids (MUA). The TEM image shows an example of MUA-linked thin film assemblies of 6-nm sized Au nanoparticles. On the basis of the interparticle spatial structures and properties shown in FIG. 2A and the relative core-shell composition revealed in previously published studies, there are important differences between MUA-linked thin film assemblies and unlinked assemblies of DT-capped gold nanoparticles. The first difference is associated with the interparticle interactions. The presence of hydrogen bonding in combination with interdigitation of the alkyl chains creates a mediator-template structure for the interparticle structure of the MUA-linked assemblies. In contrast to the relatively strong mediator-templating interparticle interactions, there is only weak interparticle interaction due to the interdigitation of alkyl chains for the unlinked assemblies of DT-capped nanoparticles. This difference is evidenced by the solubility difference for these films. For example, the unlinked DT-Au$_{2nm}$ film can be dissolved in hexane solvent. The MUA-linked DT-Au$_{2nm}$ film is insoluble in hexane solvent, but can be dissolved in the presence of more polar solvent such as ethanol.

Secondly, there is a significant difference in relative volume percentages of metal vs. organic components in terms of the particle cores and the organic capping/linking shells in these thin film assemblies as a function of particle size. As shown in FIG. 2B, while the relative percentage of the particle cores (filled circles) increases with the particle size, the relative percentage of the organic capping/linking shells (filled triangles) decreases with the particle size. It is clear that the assemblies of the 2-nm sized particles have a shell-to-core ratio of ~4 whereas that for the 7-nm particles is less than 1. Such difference was in fact supported by thermogravimetric analysis of metal to organic ratios for the nanoparticles with different sizes.

Thirdly, the size difference leads to a major difference in the relative composition of linking versus capping molecules in the organic shells between the different sized particles. As shown in Table 4 below, the extent of MUA-DT exchange was found to be about 8% for Au$_{6nm}$ particles and ~46% for Au$_{2nm}$ particles. According to this trend, the MUA linked $Au_{7nm}$ film is expected to exhibit an even lower extent of exchange. This type of difference leads to differences for these thin films in terms of chemical and physical characteristics of the overall nanostructure. For example, the interparticle hydrogen-bonding and hydrophobicity properties have been shown to play an important role in the regulating the adsorption and fluxes of molecules and ionic species across the nanostructured thin film interfaces.

TABLE 4

| Film | Particle size (nm) | % wt of organic shell[a] | MUA Exchange Rate[b] | Resistance (MΩ) |
|---|---|---|---|---|
| $NDT-Au_{2\,nm}$ | 2 | 20.7% | 0 | 6.1 |
| $MUA-Au_{2\,nn}$ | 2 | 20.7% | 46% | 13.8 |
| $MUA-Au_{7\,nn}$ | 7 | 5.9% | 8%< | 0.81 |
| $DT-Au_{7\,nm}$ | 7 | 5.9% | 0 | 17.7 |
| $DT-Au_{2\,nm}$ | 2 | 20.7% | 0 | ~350 |

For the chemiresistor sensors, the interparticle nanostructural differences lead to significant differences in electrical conductivity of the thin film assemblies, which has been shown to be highly dependent on the relative metal core vs. organic linking/capping shell structures. This dependence is reflected by the initial resistance values of the nano structured thin films (Table 4). The initial resistance of $MUA-Au_{2nm}$ films is larger than that from $MUA-Au_{7nm}$ films, which is due to the activation energy for the thin film of the 2-nm sized particles is greater than that for the 7-nm sized particles. The initial resistance of $NDT-Au_{2nm}$ films is smaller than that from $MUA-Au_{2nm}$ film and other films. The initial resistance of $MUA-Au_{7nm}$ films is smaller than that from $DT-Au_{7nm}$. The differences of the initial conductivities reflect the differences of a combination of several parameters including interparticle distances and dielectric medium constants. The average resistance for cast $DT-Au_{2nm}$ films was about 350 MΩ, a value too large and beyond the measurement range of the Keithley, Model 2700 instrument used in this work.

The electrical properties are also dependent on the design parameters of the interdigitated microelectrodes for the chemiresistor on the flexible substrate. Table 5 lists a representative set of design parameters in terms of finger space (S), finger width (W) and finger length (L), and the resistance values for $MUA-Au_{2nm}$ thin films. The measured initial resistance (R) is related to the lateral conductivity (σ) of the film ($\sigma=(1/R)(S/dL(N-1))$, where S is the finger space, L is the finger length of the microelectrodes, N is the number of microelectrode pairs, and d is the film thickness). The thickness of the film can be controlled by assembly time and interparticle distance. In this example, for all chemiresistors with different design parameters of the interdigitated microelectrodes, the MUA-linked thin films were prepared from the same assembly solution within the same time frame.

TABLE 5

| Design # | W (μm) | S (μm) | L (μm) | Initial Resistance R (MΩ) |
|---|---|---|---|---|
| 1 | 5 | 5 | 100 | 8 |
| 2 | 5 | 10 | 100 | 19 |
| 3 | 10 | 5 | 100 | 11 |
| 4 | 10 | 5 | 300 | 9 |
| 5 | 10 | 10 | 100 | 26 |
| 6 | 10 | 10 | 400 | 20 |

Under such conditions, the variation of the film thickness was shown to be insignificant. The initial resistance (R) was found to increase with increasing finger space (S) for $MUA-Au_{2nm}$ films due to increase of W and decrease of the number pairs of electrode N in the equation. It was found that the initial resistance (R) was decrease with increasing the number pairs of electrodes by shrinking the finger width in a same total height of fingers. The data indicated that the finger space had significant effects on the thin film resistance properties. The CR devices with smaller S exhibited smaller initial resistance value than those with larger S. This finding is qualitatively consistent with the expectation based on thin film conductivity. In addition, finger length (L) also seemed to play an important role in the thin film resistance properties. By comparing the CR devices with the same finger space but different finger length, it is found that those with longer L had smaller initial resistance values. There was a relatively insignificant effect of the finger width (W) on the thin film resistance properties.

One property of flexible devices is the viability of high tolerance toward repeated bending or wrapping, which was also examined for the TFA-Au/CR/PET devices. The change of the resistance in response to bending of the device from two different directions (in each direction the approximate diameter for the bent circle is about 0.5 cm) was also measured. A typical set of testing results showing the resistance change for the $MUA-Au_{2nm}$ thin film assembly upon bending of the flexible device along the indicated directions is shown in FIG. 4.

The results showed that the bending decreased the resistance by about 10% upon concave bending along the two indicated directions. While the exact origin for the slight decrease of the resistance is not known at this time, it is hypothesized that the bending creates a better electrical continuity between the assembled nanoparticles and the electrode fingers. However when the flexible device was allowed to return to flat position, the resistance recovered, indicating that the film on the flexible substrate was quite stable and had a good adhesion on the PET substrate.

The relative change in resistance or conductivity of the nanostructured thin films were further analyzed in terms of concave or convex wrapping of the TFA/CR/PET device. The electrical conductivity of the thin films can be described by a thermally-activated conduction path as shown in Equation (4):

$$\sigma = \sigma_0 \exp(-\beta d)\exp\left[-\frac{0.5e^2}{4\pi\varepsilon\varepsilon_0 RT}\left(\frac{1}{r}-\frac{1}{r+d}\right)\right] \quad (4)$$

where $e=1.6\times10^{-19}$ C, $\varepsilon_0=8.854\times10^{-12}$ F/m, $R=1.38\times10^{-23}$ J/K, $T=300$ K, and r and d represent particle radius and interparticle spacing (nm), respectively.

The response characteristics of the TFA-Au/CR/PET chemiresistors to selected VOCs and water vapor were examined. One of the main emphases is the understanding of the correlation of the response characteristics of the nanostructured thin film assemblies on the flexible substrates with the nanostructural parameters and the device design parameters. This correlation builds upon on the dependence of the overall electronic conduction (electron hopping and/or electron tunneling) on the nanostructural parameters such as particle core radius (r), interparticle distance (d), and dielectric constant of interparticle medium ($\varepsilon$).

Equation (4) can be written in terms of activation energy as shown in Equation (5a) and (5b) below:

$$\sigma = \sigma_0 \exp\left(-\frac{E_a}{RT}\right) \quad (5a)$$

$$E_a = 0.5 e^2 \frac{r^{-1} - (r+d)^{-1}}{4\pi\varepsilon\varepsilon_0} \quad (5b)$$

For the four types of thin film assemblies of gold nanoparticles, i.e., MUA-$Au_{2nm}$, MUA-$Au_{7nm}$, DT-$Au_{2nm}$, and DT-$Au_{7nm}$ films, the nanostructures differ in particle size and interparticle properties. Therefore, the determination of their sensor response characteristics provides a model system for assessing the correlation of the electrical signals with the three nanostructural parameters, r, d, and ∈. In this subsection, the results obtained for the sensor response characteristics of these thin film assemblies are discussed. Note that the resistance for the DT-$Au_{2nm}$ films was often too large and beyond the measurement range of the instrument used in this work.

A series of VOCs such as benzene (Bz), hexane (Hx), and toluene (Tl) and water vapor were tested with the TFA-Au/CR/PET chemiresistors. FIGS. 5A-B shows a representative set of the sensor response profiles for the MUA-$Au_{2nm}$ film. The response profile features an increase in $\Delta R/R_i$ upon exposure to the vapor which returns to baseline upon purge with nitrogen. The response is rapid and reversible. In most cases, the responses increased linearly with vapor concentration when the concentration is not too high. The slope serves as a measure of the response sensitivity. Deviation from the linear relationship occurs when the vapor concentration is above a certain value, the exact value of which depends on the vapor. Such a deviation is due to the existence of a saturation effect and or the complication of both bulk and surface adsorption phenomena. For the convenience of an overall assessment of the data, the linear approximation was used for assessing the response data. An important finding for this MUA-$Au_{2nm}$ film from the data in FIGS. 5A-B was that while similar positive trends of response and sensitivity profiles were observed for benzene, hexane, and toluene (not shown) vapors, a negative response was observed for the response to water vapor.

FIGS. 6A-B shows another representative set of the sensor response and sensitivity profiles for MUA-$Au_{7nm}$ film in response to the same set of vapors. In contrast to the response characteristics observed for the MUA-$Au_{2nm}$ film, the data for the MUA-$Au_{7nm}$ film showed positive trends in response to all these vapors.

In comparison with the data for the above molecularly-linked thin film assemblies, the unlinked DT-$Au_{7nm}$ film showed similar response profiles to benzene, hexane, and toluene (not shown) vapors with subtle differences in response sensitivity (FIGS. 7A-B). The response sensitivity of the DT-$Au_{7nm}$ film is found to be about 2~5 times larger for the tested VOCs than that of MUA-$Au_{2nm}$ and MUA-$Au_{7nm}$ films. For water vapor, the DT-$Au_{7nm}$ film showed positive response to water vapor but with a very small sensitivity in comparison with MUA-$Au_{2nm}$ films.

The above response characteristics for MUA-$Au_{2nm}$, MUA-$Au_{7nm}$, DT-$Au_{7nm}$, and NDT-$Au_{2nm}$ films are further compared (see, e.g., Table 6 below). The response sensitivity is expressed in differential change of resistance per ppm of vapor concentration. By comparing the response sensitivities for the nanoparticle thin films, a high sensitivity was observed for DT-$Au_{7nm}$ in response to benzene, hexane, and toluene vapors. The response of DT-$Au_{7nm}$ to hexane is almost 10 times larger than those for the other two films. For water vapor, the MUA-$Au_{2nm}$ film showed a negative response profile, whereas the unlinked DT-$Au_{7nm}$ film showed the smallest response sensitivity to water vapor among the three different films. Note that the response signal of NDT-$Au_{2nm}$ film to water vapor was very small and difficult to be extracted from the background noise. The issue on a possible effect of film thickness on the sensor response sensitivity was addressed by examining the dependence of the sensitivity vs. the relative film thickness. The sensitivity was found to be dependent on the thickness only for very thin films with a relative thickness<100 layers. For relatively thicker films, the sensitivity is essentially independent on the film thickness. The fact that the films tested were all relatively thicker substantiated the comparison of the response sensitivity data in the experiment.

A summary of the above data is shown in Table 6, which provides important information for assessing the correlation between the sensor response sensitivities and the thin film nanostructural parameters in terms of r, d, and ∈. For NDT-$Au_{2nm}$ and MUA-$Au_{2nm}$ films, the combination of the small particle size and the relatively large interparticle spacing leads to a high percentage of organics, or a high percentage of MUA (for MUA-$Au_{2nm}$ film). Such films have a relatively low electrical conductivity. For vapors that are hydrophobic (Bz, Hx, and Tl) and have small ∈ values, the change in interparticle spacing (d) upon the sorption of these vapors in the film is dominant. A positive response characteristic is thus observed.

TABLE 6

| | Response sensitivity[c] ($ppm^{-1}$) × $10^4$ | | | |
|---|---|---|---|---|
| Sensing films | Hx | Bz | Tl | Wa |
| NDT-$Au_{2\,nm}$ | 0.54 | 0.95 | 3.03 | — |
| MUA-$Au_{2\,nm}$ | 0.59 | 1.15 | 2.78 | −1.84 |
| MUA-$Au_{7\,nm}$ | 0.65 | 1.73 | 2.65 | 0.65 |
| DT-$Au_{7\,nm}$ | 5.28 | 4.53 | 5.49 | 0.32 | wherein the response sensitivity is given in the unit of ppm (M), which can be converted to the unit of ppm (V) by dividing the value by a factor of 24.5.

In comparison, the increase in particle size (i.e., MUA-$Au_{7nm}$) leads to a lower percentage for both organics and MUA, and thus a higher electrical conductivity. The positive response characteristic remains unchanged for vapors such as Bz, Hx, and Tl because the change in interparticle spacing (d) upon the sorption of these vapors in the film is still dominant. However, a slightly-larger positive response is observed in the case of Bz and Hx, which reflects the change in conductivity as a result of the increased particle size. Interestingly, a negative response characteristic is observed for the sorption of water vapor in the MUA-$Au_{2nm}$ film. This finding may reflect the dominant role of the change in dielectric constant (∈) in the thin film as a result of the combination of the relatively high percentage of MUA in the film and the high dielectric constant for water. When the percentage of MUA in the thin film is significantly reduced, i.e., the MUA-$Au_{7nm}$ film, a positive response characteristic is observed.

In contrast to the MUA and NDT linked thin film assemblies of nanoparticles, the unlinked DT-Au thin film features a highly-hydrophobic structure, and the interparticle packing relies on weak van der Waals interaction only. In this case, the thin film (e.g., DT-$Au_{2nm}$) is highly resistive, often too resistive to be measured with the conventional instrumental capability range. The thin film (e.g., DT-$Au_{7nm}$) can also show a positive response characteristic regardless of the hydrophobicity or dielectric constant of the vapors because the change in interparticle spacing is always dominant upon the sorption of the vapors in the hydrophobic and loose-packing thin film. The characters of loose packing and low conductivity are in fact supported by the significant differences in resistance between the molecularly-linked nanoparticle assemblies (lower resistance) and the unlinked nanoparticle assemblies (higher resistance).

The thin film response characteristics were further analyzed based on principal component analysis (PCA), which was aimed at assessing the potential selectivity of the flexible sensor arrays for the detection of VOCs. Using methods known in the art for analyzing sensor array responses of thin film assemblies on rigid substrates, the PCA technique was applied to the data analysis for a flexible sensor array with different nanoparticle thin film assemblies in response to selected VOCs. The PCA analysis can extract the information from a great deal of raw data, which was achieved by converting a large number of potentially correlated variables into relatively small number of uncorrelated variables. PCA analysis was used to assess the selectivity of a sensor array in distinguishing different vapors through the reduction of variable dimensions (feature extraction) and classification. To establish the relation between the classification capability of the sensor array and the nanostructural parameters, data was analyzed from sensor arrays with different combinations of the thin films. The classification capability of each array was dependent on the specific combination.

One representative example of such an analysis can be illustrated by the analysis of two sets of sensor response data for a 3-film sensor array consisting of MUA-$Au_{2nm}$, MUA-$Au_{7nm}$, and DT-$Au_{7nm}$ thin films in response to four different vapors (hexane, benzene, toluene, and water). FIGS. 8A-B shows a set of the PCA score plots for the sensor responses to hexane, benzene, toluene, and water vapors in the PC1-PC3 and PC1-PC2-PC3 plane. This set of results was obtained from the PCA analysis of the normalized responses at eight different vapor concentrations. From the PCA score plots, it was observed that there is no overlap of the normalized responses, as evidenced by the separation of the clusters in both the PC1-PC3 and PC1-PC2-PC3 planes. Therefore, each of the four vapors can be clearly identified by the selected sensor array.

The further application of the discriminant analysis technique with a quadratic discriminant function to the sensor array data for classifying observations into predefined classes and determining the class of an observation based on a training data set has also demonstrated identification of each of the four tested vapors. In this type of data analysis, the first three principle components (PC1, PC2, PC3) were used as the classification features. The results showed that the recognition rates with 100% for hexane vapor, 90% for benzene vapor, 94% of toluene vapor, and 100% of water vapor were achieved with the selected flexible sensor array. This finding, upon further delineation with other different combinations of thin films and analytes, has important implication to increase the selectivity of the flexible TFA-Au/CR/PET arrays for the detection of VOCs.

In view of the foregoing, Example 1 demonstrates flexible chemiresistor sensors comprising thin film assemblies of nanoparticles as sensing materials and a polymer such as polyethylene terephthalate as a substrate. The finding on the correlation between the relative change in electrical conductivity and relative change in dielectric medium constant in response to flexible wrapping of the device demonstrated that electrical responses can be manipulated in terms of the wrapping direction of the flexible substrates. The response characteristics of the nanostructured flexible array in response to VOCs have been shown to be dependent on the particle size, the interparticle properties, and the substrate-thin film interactions. The results show a correlation between the response characteristics and the nonstructural properties for exploiting the combination of nanoparticle-structured sensing materials and flexible sensor array devices for the detection of VOCs.

For molecularly-linked nanoparticle thin film assemblies with small particle size and large interparticle spacing which have a high percentage of organics and linker molecules, the relatively low conductivity renders the change in interparticle spacing to play a dominant role in the sensor response to vapors that are hydrophobic and have small $\in$ values. In this case, the positive response is characteristic of the response profile. In comparison, the combination of the relatively high percentage of linker molecules in the thin film and the high dielectric constant for the vapor molecules (e.g., water vapor) leads to a negative response characteristic which is determined by the dominant role of dielectric constant. In contrast to the molecularly-linked thin films, the response characteristic for thin films with only weak interparticle VW interactions is always dominated by the change in interparticle spacing regardless of the percentage of organics in the film and the dielectric constant of the vapor.

Example 2

In one embodiment, a flexible chemiresistor (CR) breach sensor array for detecting acetone in breath.

This example demonstrates the use of molecularly-mediated thin film assemblies on flexible devices as sensor arrays for detecting biomarkers for diabetic breath. This example also demonstrates a noninvasive device for diagnostic monitoring.

There is a significant market need for cost-effective medical devices for rapid diagnostics of diabetes and glucose monitoring. While different devices have been developed for detecting glucose levels in diabetic patients, there is a need in the art for diagnostic analysis of glucose level via breath detection, especially portable sensor devices. Glucose sensors coupled with insulin delivery pumps are well known in the art. Recently, a "pumpless" micropump has been developed. The working principle involves electrically-induced interfacial tension at the boundary of two immiscible liquids that produces actuation force. This is a low-power-driven micropump which is potentially applicable to the fabrication of implantable micropump for insulin delivery and glucose sensing in a micro chip. Many practical issues, however, remain to be solved in interfacing such a device with a patient. As an alternative, the expansion of Portable Sensor Array (PSA) technology for breath sensors is highly attractive for the market because it involves a simple detection mechanism. Importantly, the portable, non-invasive, and cost-effective features could well compete with other related technologies such as the sensor that uses cavity ringdown spectroscopy to screen for the diabetes.

There are certain VOCs that can serve as biomarkers for diabetes in the human breath. Acetone is qualitatively known as a biomarker of diabetes. The acetone levels are <0.9 ppm for healthy individual and >0.9 ppm for diabetic individual. Relations between breath acetone and blood glucose (BG), glycohemoglobin A1C (A1C), and several other bio indices, such as the type of diabetes, onset-time, gender, age, and weight were investigated, and the linear correlation between the mean group acetone and the mean group BG level was reported.

Currently, the frequent monitoring of blood glucose levels in diabetes involves blood samples collected by pricking the finger up to four times daily. These blood tests are painful and expensive. While the cost of test supplies and volume of blood needed for testing both have decreased over the years, finger sticks remain painful and pose risks for infection, especially for people with diabetes. Noninvasive glucose measurement methods, therefore, would be extremely desirable. Although patents for noninvasive skin-based glucose measurement devices exist (e.g. spectrophotometric monitoring), no such device is commercially available today.

The breath is a mixture of volatiles, including volatile organic compounds (VOCs) such as acetone, ethanol, etc, and in some cases contains markers of disease, making breath analysis a useful screening, diagnostic, and monitoring tool. Breath samples are already routinely used to diagnose some conditions that involve problems with carbohydrate digestion (e.g. lactose intolerance) and to measure blood ethanol levels, (e.g. breathalyzer test), and exhaled acetone has been studied since the 1960s as a marker for diabetes. Breath analysis using gas chromatography (GC) and GC-mass spectroscopy (GC-MS) methods has been well established, and applied to studies of diabetes, lung cancer, respiratory tract diseases, oxidative stress in diabetes, and liver deficiency. The GC-MS analysis of breath samples taken from patients with type II diabetes showed a clear correlation between the concentration of breath acetone and HbA1c level (a marker of long term glucose levels).

In addition to detecting breath acetone level, a correlation between the breath and urine acetone concentration was also observed, suggesting potential applications of breath analysis to determine the blood glucose level. Breath ethanol and acetone (produced via alcoholic fermentation of glucose and oxidation of free fatty acids, respectively) were recently shown to serve as indicators of serum glucose levels. Multilinear regression analysis of exhaled VOCs as biomarkers of endogenous metabolism indicated the possibility of measuring plasma glucose and demonstrated the feasibility of potential breath-based glucose testing. The major advantages of breath analysis over existing serum or urine analysis include noninvasiveness, close reflection of the arterial concentrations of biomarkers, less complicated mixture than serum or urine, and real-time monitoring.

In comparison with GC or GC-MS based breath analysis, electronic noses have the advantages of portability, cost-effectiveness, easy operation, fast reading, and the potential to produce a chemical fingerprint of overlapping sensitivities when an array of chemical sensors coupled with pattern recognition are used. The latter allows building a database of complex composition for speciation in a way resembling human noses. Early work in the detection of acetone in human breath demonstrated that large amounts of acetone, a marker of a widespread metabolic syndrome, were excreted through the lung in patients suffering from diabetes by bubbling breath in an alkaline iodine solution. While there were studies of semiconductor acetone sensor, quartz crystal microbalance array, and potentiometric sensors in this area, one of the main problems in diagnostic breath analysis is the difficulty to establish the correlation between the biomarker with a pathology due to the fact that the substance concentrations in the exhaled air change under various conditions which are often at trace levels. Most commercial gas sensors suffer from poor detection limit, poor selectivity, and high cost, and are inadequate for addressing the challenges in breath sensing of diabetes. The proposed coupling of a flexible nanostructured sensor array with mouse model of diabetes breath offers a new strategy to address the existing problems in breath detection of diabetes.

In this example, molecularly-mediated thin film assemblies of nanoparticles are coupled with a pattern-recognition engine in a flexible array device for enhancing sensitivity and selectivity. FIG. 9 illustrates the design principles of the nanostructured sensor array in terms of three types of analyte-binding sites (I, II, & III), and pattern recognition in an integrated sensor platform.

This sensor platform not only employs the hopping/tunneling of electrons in a collective ensemble of nanoparticles as a highly sensitive interface, but also employs the attributes of the nanostructure, including enrichment of molecular ligands/voids with high surface area-to-volume ratio, non-covalent character of molecular interactions (e.g., hydrogen-bonding, ligand coordination, van der Waals interaction), and selective catalytic binding sites. To achieve a portable and reliable breath sensor array for use in a wide range of complex sensing environment, this example shows that device module flexibility can be used that is conformal adaptively to different sensor platforms, and that can be used in applications under conditions such as conformal wrapping over curvilinear surfaces, high tolerance toward repeated bending, and mechanical shock resistance. Thin films of monolayer-capped metal or metal oxide nanoparticles can be assembled on either the entire chemiresistor array by molecular mediators (e.g., 11-mercaptoundecanoic acids (MUA) or 9-nonanedithiols (NDT), or on each of the active interdigitated microelectrode areas by PDMS-stamp transferring method. The nanoparticle thin film assemblies function as the sensing materials in which the electrical properties are tuned by the nanostructural parameters such as particle radius (r), interparticle spacing (d), and interparticle dielectric constants ($\in$), whereas the flexible substrate enables device adaptively and low cost. The molecular interactions of biomarkers in the nanostructure induce changes in electronic conductivity with response signatures identifiable by the array coupled with pattern-recognition engine with high sensitivity and selectivity, low detection limit, and rapid response time. The thermally-activated electrical conductivity is dependent on particle size, interparticle spacing, dielectric constant, and linker/capping structures as shown in Equation (6) below:

$$\sigma = \sigma_0 \exp(-\beta d) \exp\left[-\frac{0.5 e^2}{4\pi \varepsilon \varepsilon_0 RT}\left(\frac{1}{r} - \frac{1}{r+d}\right)\right] \quad (6)$$

In addition to the change of d associated with r, the change of the apparent $\in$ is possible depending on the packing of the interparticle capping/linking molecules, the tolerance toward repeated bending or wrapping, and the gas/vapor environment. It is hypothesized that the bending under different gases/vapors creates a tunable electrical continuity between the assembled nanoparticles and the microelectrodes. As such, conformal bending of the flexible device provides a useful means for manipulating the sensor responses.

As known in the art and as demonstrated by the data presented in this example, the variance of the results from day-to-day and person-to-person tests in the existing breath analysis data reflects the complication caused by uncontrolled variables such as dietary or food differences, personal care product usage, and other environmental variables that can impact on breath composition. While the data provided a promising lead to the feasibility of human breath sensing, the overlaps of different human breath samples and the data spread are clearly complex, calling for innovation in addressing both multiplex sensor detection and animal model testing. The composition of human breath is complex because there are strong indications that many VOCs found in human breath may be markers of certain diseases. In the air breathed out of the lungs which contains approximately 15% $O_2$, 6% $H_2O$, and 5% $CO_2$, acetone is identified to be associated with diabetes, in addition to about ten other major biomarkers including hydrocarbons in actual human breath. In view of the complexity of breath composition, the sensors is preferably designed to be exceptionally fine-tunable towards high sensitivity, low detection limit, high selectivity, and importantly reproducibility. A recent study of polypyrrole thin film based sensor array demonstrated the feasibility to separate breaths from the normal people and the diabetic patients, but the data were based on a very small number of people (3 diabetes patients). Clearly, in addition to low sensitivity and selectivity for diabetes breath analysis, the inability for reliable and reproducible detection of human breaths under various conditions constitutes a main drawback in existing approaches to diabetes breath sensor research. This example demonstrates the performance of a nanostructured multiplex sensor array in a mouse model for diabetic breath.

A variety of chemicals can be used. 11-mercaptoundecanoic acid (HS—$(CH_2)_{10}$—$CO_2H$, MUA), 1,9-nonanedithiol (HS—$(CH_2)_9$—SH, NDT), and decanethiol (HS—$(CH_2)_9$—$CH_3$, DT) were used as received (Aldrich). Vapors were generated from hexane ($C_6H_{14}$, Hx, 99.9%, Fisher), benzene ($C_6H_6$ ($\phi$), Bz, 99.0%, Fisher), toluene ($\phi$-$CH_3$, Tl, 99.9%, J. T. Baker).

Gold nanoparticles of 2 nm core size encapsulated with decanethiolate (DT) monolayer shells were synthesized according to a two-phase method using a synthetic modification. Details for the synthesis of 2-nm gold nanoparticles ($Au_{nm}$, 1.9±0.7 nm) have been previously described. Gold nanoparticles with larger sizes were synthesized by a thermally-activated processing route known in the art. Briefly, the solution containing the as-synthesized DT-$Au_{2nm}$ nanoparticles from the synthesis was heated at 150° C. to produce larger-sized Au nanoparticles. Gold nanoparticles of 7.0±0.5 nm diameters ($Au_{7nm}$) produced by this method were used in this work.

In one exemplary fabrication, IMEs of microelectrode parameters were fabricated by microfabrication, including 150 pairs of gold (150 nm thick) electrodes of 10 μm finger width, 10 μm finger space and 100 μm finger length, 200 pairs of gold electrodes of different finger width (5 μm, 10 μm), different finger space (10 μm, 5 μm) and 200 μm finger length, and 300 pairs of gold electrodes of 5 μm finger width, 5 μm finger space, and 100 μm finger length. The thin film electrodes were manufactured on glass substrate using Nordiko 2000 vacuum sputtering deposition system, in a base pressure below $1.5 \times 10^{-6}$ torr with ultrahigh purity (99.999% pure) inert Ar acting as a sputtering gas. The IME device structure was patterned by photolithography, using standard methods, at the Cornell Nanoscale Facility (CNF, Cornell University, Ithaca, N.Y.). To address the problems associated with the lack of controllability over the electrode adhesion and spacing of IMEs by standard microfabrication techniques, each of the microfabrication steps was modified using routine modifications known in the art, ranging from wafer cleaning, gold deposition, lithographic patterning, and wet chemical etching. Adhesion test, electrical testing, microscopic examination, and sensor array testing all showed that these IMEs produced by the modified processing control parameters met the desired performance criteria. A 30 nm Ti was sputtered onto glass substrates to act as an adhesion layer before the subsequent Au films of about 150 nm was deposited.

The deposited Au/Ti films were subsequently processed at the CNF clean-room facility. Lithographic processing was carried out using standard methods known in the art. The first step of lithographic processing began with spin-coating with P-20 primer followed by a layer of S-1813 photoresist. These polymer-treated wafers were then baked on a hot plate for 120 sec, followed by proper exposure to the UV light from a Contact Aligner using a negative image chrome mask with designed patterns. Next, the exposed wafers were baked in oven for 85 min. The wafers were then flood-exposed to the contact aligner for 60 seconds and then developed by MF-321 developer. The acid mixture used for etching away the Au film layer was $HCl:HNO_3:H_2O$ in 3:1:1 ratio with the acid bath at lukewarm temperature of 30° C. The etching period in the solution was typically 30~32 sec for 150 nm Au film. Once the upper layer of the Ti/Au film was removed, the underlying Ti adhesion layer was etched for approximately 50 seconds with $NH_3OH:H_2O_2$ (30%) mixture of 1:2 ratio at room temperature.

In one exemplary preparation of thin film, the nanoparticle thin films prepared for the present work included two types: (1) NDT-linked nanoparticles (NDT-$Au_{nm}$) and (2) MUA-linked nanoparticles (MUA-$Au_{nm}$). The thin films were prepared via an "exchanging-crosslinking-precipitation" route. The reaction involved an exchange of linker molecule (NDT, MUA) with the gold-bound alkanethiolates, followed by crosslinking and precipitation via either Au—S bonding at both ends of NDT, or hydrogen bonding at the carboxylic acid terminals of MUA. The IME substrates of the four different designs were then immersed into the same solution of the mixed nanoparticles and thiols at room temperature, and solvent evaporation was prevented during the film formation. The thickness of the thin films grown on the surface of the substrates was controlled by immersion time. Thin films of the same thickness were assembled on the IMEs of four different designs. The thin films thus produced were thoroughly rinsed with the solvent and dried under nitrogen. The NDT-$Au_{nm}$ coated sensors are denoted as NDT-$Au_{nm}$/IME. Similar notations are for MUA-$Au_{nm}$/IME.

One challenge in the design of the circuit boards was the control of low currents which cause instability of the sensing films. Based on test results, it was discovered that the current flow of more than several μA might have an effect on the sensor stability. The design provided herein solved the problem of large current flow impacting sensor stability.

The multichannel sensor array board employed reference resistors for performing measurements. This approach allowed elimination of the switch components to avoid harmful pulse currents. The sensor signals were amplified by adjusting the value of each reference resistor to match the corresponding sensing film in the sensor array. The amplified analog signals were conditioned and converted to digital signals in the control and data acquisition circuit. The output digital signals were processed by computer.

The circuit board design included a precision current generator, non-inverting amplifier, 24-bits A/D converter, and pulse current filter. A high signal-noise ratio (noise<1%) and wide measurement range (100 KΩ-300 MΩ) was achieved with this design.

The hardware had the following features: 1) accurate differential amplification for removing noise, 2) elimination of multiplexers, 3) accurate bias current supply for accurate signal read-out, 4) incorporation of plug-and-play bias resistors which have more flexibility in the measurement, and 5) faster response and reliable data.

Figure 10:
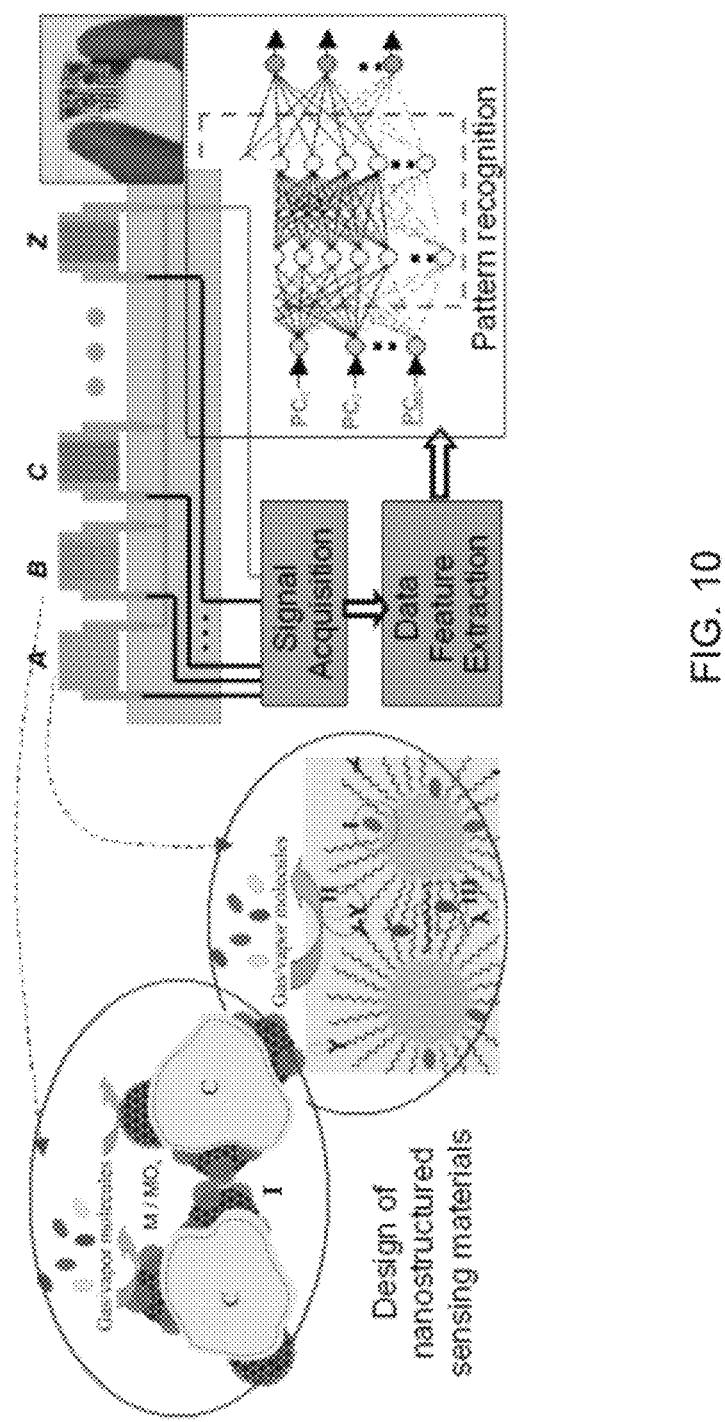
FIG. 10 depicts one or more design principles of an exemplary nanostructured sensor array in terms of three types of analyte-binding sites (e.g., sites I, II, and III) and pattern recognition in an integrated sensor platform.

The circuit board design with functional block is shown in FIGS. 10A-C. The software design and data processing development was for achieving a better way to process sensor signals which aided the pattern recognition process. Filtering methods were developed to increase the signal-to-noise ratio. Three filtering methods were used: moving average, locally weighted scatter plot smooth, and Savitzky-Golay filtering methods. The noise was reduced by applying these filters. FIG. 10A shows the PCB design with functional block. FIG. 10B shows the flow diagram of software. FIG. 10C shows that flow-diagram for the sensor array data processing and optimization procedure. Through optimization, i) a stable, efficient, and flexible sensor array optimization approach can be developed; ii) the diversity of sensor array, and remove redundant information from input can be increased, and iii) associating optimization with some specific classification algorithm can be avoided.

Figure 11C:
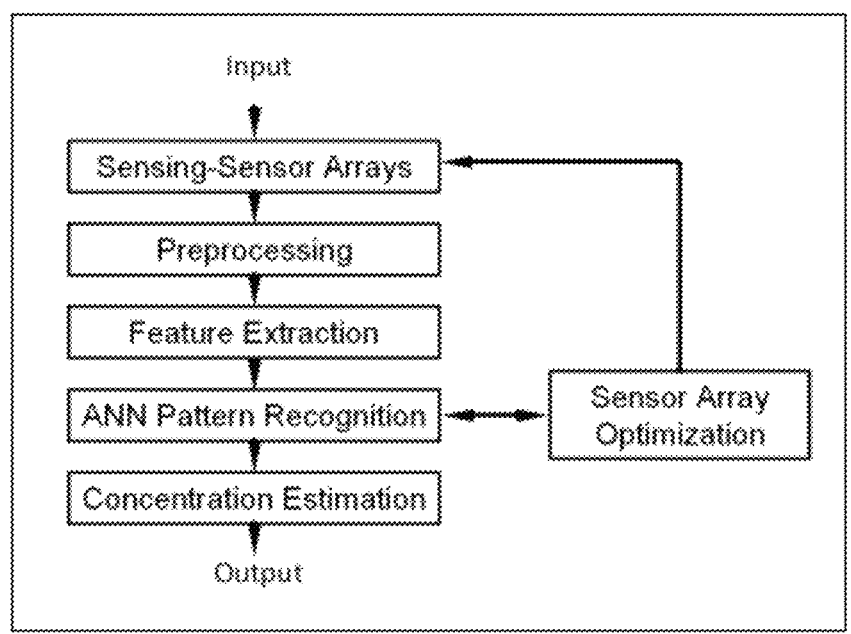
FIG. 11C depicts a flow diagram of an exemplary sensor array data processing and optimization.

The sensor array test chamber array modules was designed for more compact and robust applications. FIGS. 11A-B show the photo of sensor array chamber with six sensor devices and the overall assembly. The basic features included (1) compact design (5 cm diameter and 4 cm high), (2) minimized gas volume above sensor devices, and (3) uniform exposure of each sensor to the gas/vapor.

FIG. 11B shows photos of the various components for the Portable Sensor Test System. The circuit board, powered by batteries, is interfaced with the sensor array and read-out is through laptop computer. Air was pumped into the array manifold using an on-way squeeze-pump (6-sensor array) as background before and after the vapor testing. For example, when a VOC vapor is pumped into the sensor array chamber by putting the squeeze-pump tube into the bottle containing acetone, the computer screen will display the response profiles.

Figure 12A:
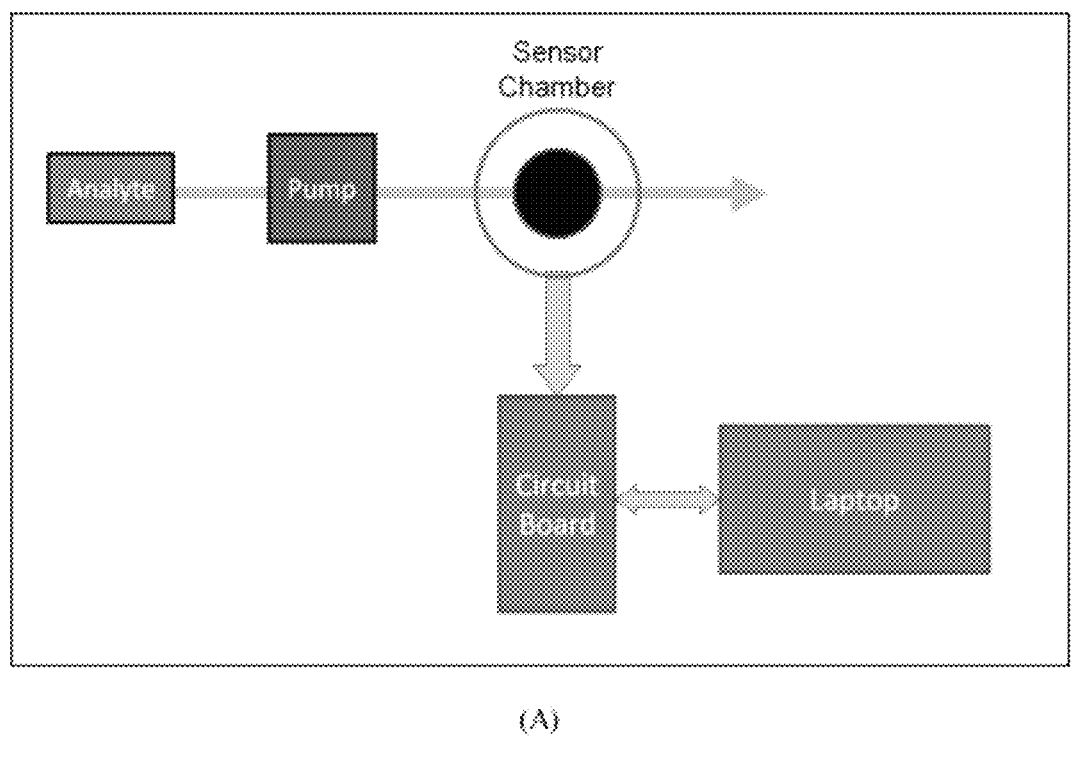
FIG. 12A depicts Scheme showing the various components for the Portable Sensor Test System.
Figure 12B:
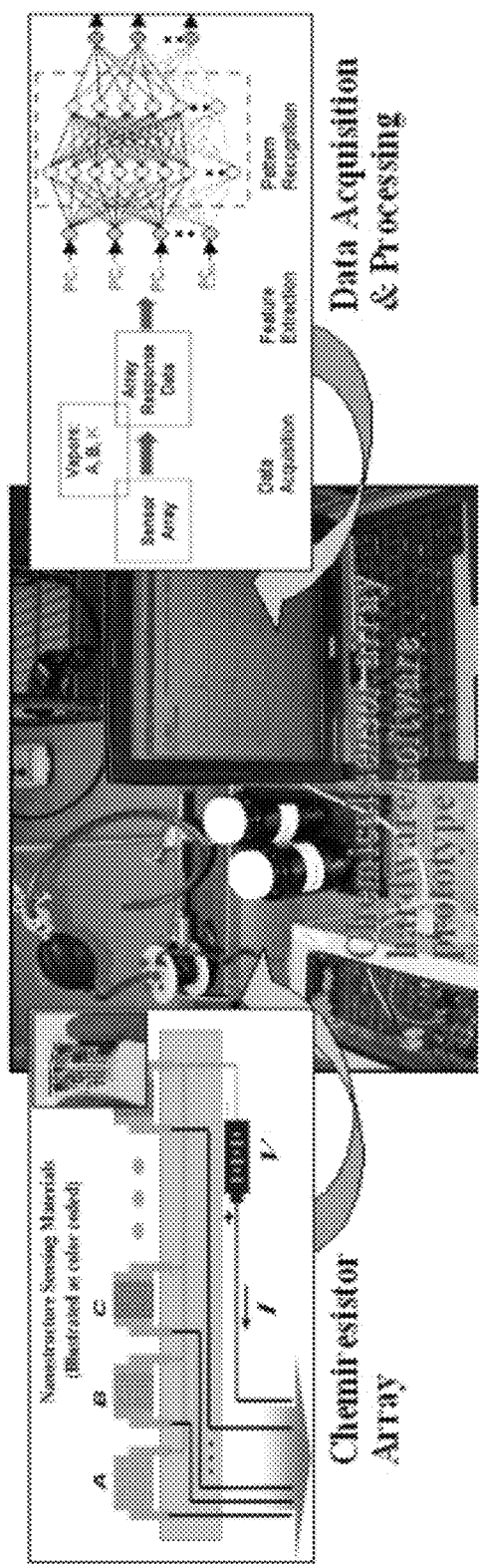
FIG. 12B depicts photo and schemes showing the initial prototype circuit board with data acquisition via a plug-and-play sensor array module for the study.

FIG. 12 shows data for the detection of acetone of various concentrations on a 10-channel IME-array with different design parameters. These IMEs were coated with 11-mercaptoundecanoic acid (MUA)-mediated thin film assemblies of gold nanoparticles of 2-nm diameter (MUA-$Au_{2-nm}$). The initial data of the sensor array seem to be very promising. It exhibits linear response vs. acetone concentration (FIG. 12). The detection limit reached 1 ppm to ~10 ppb depending on the actual combination of the IME design parameters and the array nanomaterials structures.

The sharp contrast of the response profiles between acetone and water vapors, i.e., positive response (resistance increase) for acetone and negative (resistance decrease) for water (FIG. 13A) demonstrates that the sensor arrays demonstrated in this example achieve high selectivity between acetone and water. The ability to selectively differentiate water and acetone is a major difficulty in many other existing sensor technologies. The sensor arrays coated with different nanoparticle-structured thin films, including MUA-mediated assembly of Au nanoparticles of 7-nm diameter (MUA-$Au_{7-nm}$), and 9-nonedithiol (NDT) mediated assembly of Au nanoparticles of 2-nm diameter (NDT-$Au_{2-nm}$) were also tested for these vapors.

Based on these results, the optimum combination of the sensor array was selected from the different array candidates as illustrated in the table in FIG. 12 to achieve the best selectivity. Linear Discriminant Analysis (LDA) was used to facilitate the optimum selection of sensor elements from the initial candidates by investigating how films in each group (MUA-$Au_{7-nm}$, MUA-$Au_{2-nm}$, and NDT-$Au_{2-nm}$) contribute to vapor separation. LDA is a method used in statistics and machine learning to find the linear combination of features which best separate two or more classes of objects. It approaches the problem by assuming that the probability density functions of the two classes $p(\vec{x}|y=1)$ and $p(\vec{x}|y=0)$ are both normally distributed, and the classes decision criterion can be described as in Equation (7):

$$(\vec{x}-\vec{\mu}_0)^T \Sigma_{y=0}^{-1}(\vec{x}-\vec{\mu}_0)+\ln|\Sigma_{y=0}|- \\ (\vec{x}-\vec{\mu}_1)^T \Sigma_{y=1}^{-1}(\vec{x}-\vec{\mu}_1)-\ln|\Sigma_{y=1}|<T \quad (7)$$

The separation between the two classes is then defined as the ratio of the variance between the classes to the variance within the classes as shown in Equation (8) below:

$$S = \frac{\sigma_{between}^2}{\sigma_{within}^2} = \frac{(\vec{w}\cdot\vec{\mu}_{y=1}-\vec{w}\cdot\vec{\mu}_{y=0})^2}{\vec{w}^T \sum_{y=1} \vec{w} + \vec{w}^T \sum_{y=0} \vec{w}} = \frac{(\vec{w}\cdot(\vec{\mu}_{y=1}-\vec{\mu}_{y=0}))^2}{\vec{w}^T \left(\sum_{y=1}+\sum_{y=0}\right)\vec{w}} \quad (8)$$

The films are selected with LDA method based on their response to water and mixture of water and acetone at different concentration levels. Out of initial 10 candidates, the 5 best sensors selected and their DA distances are shown in Table 7 below, which shows LDA distance between water and mixture for the selected films (film type and IME design)

TABLE 7

| MUA-$Au_{7-nm}$ (CH2) | MUA-$Au_{2-nm}$ (CH1) | MUA-$Au_{2-nm}$ (CH2) | NDT-$Au_{2-nm}$ (CH9) | NDT-$Au_{2-nm}$ (CH10) |
|---|---|---|---|---|
| 1.5379 | 18.1097 | 4.4274 | 4.8547 | 5.23877 |

The responses from the selected sensor elements are first preprocessed to eliminate some noise, and then the principal component analysis (PCA) is applied for feature extraction for the optimized sensor array. PCA is a mathematical method that converts a large number of potentially correlated variables into relatively small number of uncorrelated variables. For a data matrix, $X^T$, with zero empirical mean, the PCA transformation is given by: $Y^T = X^T W = V\Sigma^T$, where the matrix $\Sigma$ is an m-by-n diagonal matrix with nonnegative real numbers on the diagonal and $W\Sigma V^T$ is the singular value decomposition (svd) of X. PCA is used to study the responses of the five-sensor array to mixture ($H_2O$+acetone), $H_2O$, and acetone. It's observed that each of the three vapors is well separated from the others in the score plots in PC1-PC2 plane, as shown in FIG. 13B.

The sensor array performance was examined by performing pattern recognition with a Back Propagation Neural Network (BPN) on the sensor array responses to water and mixture. Since the first principle component has explained 97.3% of the variance, PC1 is used as the only input unit of the BPN. There are two units in the output layer of the BPN, in which each unit stands for the presence (+1) or absence (0) of the targeted vapor. The target output for water and water/acetone mixture are (1,0), and (0,1), respectively. The complete data set of 50 response patterns was split into a 30-pattern training set, a 10-pattern verifying set, and a 10-pattern test set. The test set consisted of testing vapors having ten different concentration levels. The performance of the BPN is evaluated by Mean Square Error (MSE), which yields a value of $2.6\times10^{-9}$ in this case. The fact that this value is so close to 0 suggests an optimal performance of this BPN. The BPN outputs for 10 test samples (acetone, water, and mixture) show that the recognition rates were 100%.

Measurements for the detection of human breath were performed using an array of 6 different sensing films (BDT- $Au_{2nm}$ (Ch1), PDT-$Au_{2nm}$ (Ch2), PrDT-$Au_{2nm}$ (Ch3), MUA-$Au_{2nm}$ (Ch4), MUA-$Au_{2nm}$ (Ch5), and PDT-$Au_{5nm}$ (Ch6)). The human breaths from healthy people were collected for the test. A small amount (210 ppm(M)) of acetone vapor was introduced into the human breath to simulate the breath with the biomarker vapor from diabetes. A squeeze-pump was used as flow controller to introduce vapor samples to the sensor chamber or air to flush the chamber. The sensor array response profiles were collected, and the data were processed for feature extraction. To examine the reproducibility of the sensor data, measurements were performed many times during a period of two months with human breath samples collected form different dates. FIG. 14A shows a representative set of data to illustrate the response profiles from one sensor element of the array. The exact profile depends on the method of introducing the samples into the test chamber using the squeeze pump (FIG. 14B), but it does not show significant impact to the data processing and final conclusion.

The sensor response data of the array were first processed to eliminate some noise before the principal component analysis (PCA) was applied for feature extraction. An optimized array was identified to consist of four-sensor elements (BDT-$Au_{2nm}$ (Ch1), PDT-$Au_{2nm}$ (Ch2), PrDT-$Au_{2nm}$ (Ch3), and PDT-$Au_{5nm}$ (Ch6)) with which the response data to human breath samples from two different healthy persons (HB1 and HB2) along with the various control experiments were processed and compared. The measurements were performed many times during a period of six months with human breath samples collected from different dates. A representative set of PCA score plots in PC1-PC2 plane are shown in FIGS. 15A-B for the results obtained on two different dates.

Thus identifying human breath with or without spiked acetone from air or acetone in air is clearly demonstrated by the separation of the data points regardless of the date. Furthermore, human breaths can be separated from acetone-spiked human breaths. However, the degree of separation is found to vary with the date when the experiment is performed. For example, a full separation was shown for the human breaths and the acetone-spiked human breaths obtained for the two healthy persons (A), whereas a limited or poorer separation was found for the human breaths and the acetone-spiked human breaths obtained several months later for the same two healthy persons. These finding were substantiated by 12 experiments performed in the 6-month period. The variance of the results with the date is due to complication caused by uncontrolled variables such as dietary or food differences, personal care product usage, and other environmental variables that can impact on breath composition.

Figure 13:
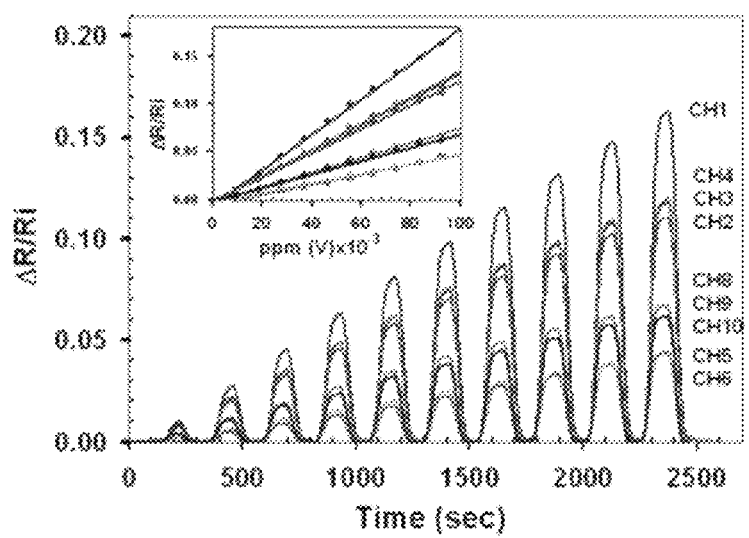
FIG. 13 depicts a plot and data for responses to acetone on a 10-channel array of different design parameters, wherein FW identifies finger width and FS identifies finger spacing coated with MUA-Au$_{nm}$ film.
Figure 17:
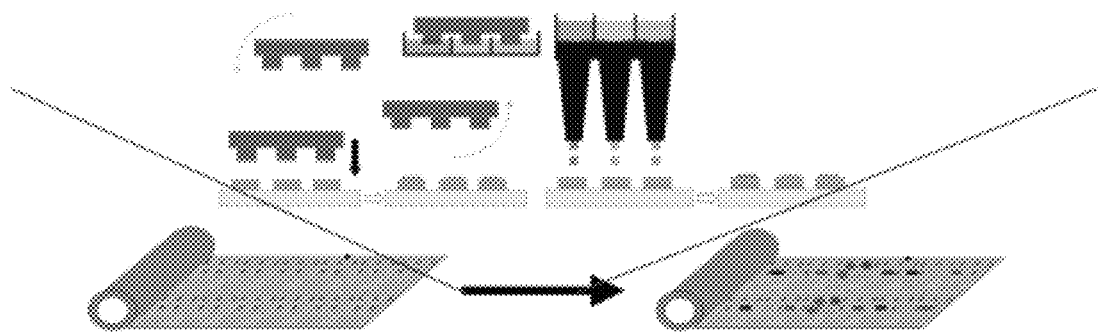
FIG. 17 depicts a schematic of an exemplary nano-manufacturing system for manufacturing a nanoparticle thin film on a flexible sensor array device.

In view of the foregoing discussion, Example 2 describes a prototype of the chemical sensor system (FIGS. 11A-C) for detection of VOCs. While the detection of VOCs by chemiresistor sensors coated with nanoparticle thin films has been demonstrated in earlier reports, this example demonstrates that the nanostructured sensor device detects acetone from vapor mixtures and normal human breath. FIG. 13 shows the detection of acetone from a mixture of acetone and water vapors is as evidenced by the result of a chemiresistor array with MUA- and NDT-mediated thin film assemblies of gold nanoparticles. This has been a major difficulty for many existing sensors in terms of differentiation of acetone from high moisture. A linear relationship was observed between the response and acetone concentration with a detection limit of 1 ppm down to ~10 ppb depending on the combination of microelectrode design parameters and nanomaterials structures (note that the concentration of acetone was shown to range from ~300 ppb for healthy people to ~2000 ppb for diabetic people). The sharp contrast of the response profiles between acetone and water vapors, i.e., positive response (resistance increase) for acetone and negative (resistance decrease) for water, and the excellent separation of binary vapors based on principal component analysis (PCA) of the response data, demonstrated the viability of achieving high selectivity.

In the second set of measurements performed many times during a period of six months using an array of 4 different sensing films, samples of human breaths from healthy people or spiked with acetone were examined. The PCA analysis of the data for breath samples from two different healthy persons on two different dates, e.g., as shown in FIGS. 15A-B and 16A-B, reveals two important findings. The first is the demonstration of the feasibility of identifying human breath with or without spiked acetone from air or acetone/air by separation of the different sets of data points. Secondly, while it demonstrated the possibility of separating the normal breaths from the acetone-spiked ones, the degree of separation varied with the date of the actual measurement. A full separation was shown for the breath samples and the acetone-spiked ones on one day whereas a limited or poorer separation was found on other day for the same two people. These two findings supported the feasibility of the nanostructured array for breath sensing in both biomarker identification and concentration differentiation, but indicated the complexity of human breath sampling in terms of the data statistics.

Having thus described the basic concept of the invention, it will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations, such as arrows in the diagrams therefore is not intended to limit the claimed processes to any order or direction of travel of signals or other data and/or information except as may be specified in the claims. Accordingly, the invention is limited only by claims that can be supported by the specification herein and equivalents thereto.

Example 3

Metal or alloy nanoparticles have attracted increasing interests as chemical or biological sensing materials for various electrical devices such as chemiresistors and piezoelectric resonators on rigid substrates. One example involves molecularly-mediated thin film assemblies of gold or alloy nanoparticles via interparticle covalent bonding, hydrogen-bonding, or van der Waals interaction on microelectrode patterned glass substrates. Recently, the study of functional devices on flexible substrates becomes an important focal area of interests. In comparison with conventional devices on rigid silicon, glass or ceramic substrates, the attributes of flexible devices include simplified processing, low-cost manufacturing, and increased flexibility for their integration in wraps, lightweight electronics packaging platform, and conformal adaptability in various complex or special sensing environment. There have been an increasing number of reports on flexible substrates for chemical sensor devices, a few of which explore nanoparticle thin film assemblies as sensing materials, including our recent work. However, relatively little is understood about how the electrical conductivity of the nanostructured materials functions on flexible chemiresistor devices. This understanding is important because the correlation between the electrical conductivity and the nanostructural parameters including particle size, interparticle distance, dielectric medium, and device strain is crucial for design of sensing arrays on flexible devices. These parameters determine the activation energy in a thermally-activated conduction path, and thus have an important impact to the electrical signal amplification in sensing applications.

One of the important characteristics of the nanoparticle assembly on flexible electrical devices is the device strain effect on electrical conductivity as a result of bending or wrapping. There have been a few recent reports on this type of electrical-mechanical properties. In a recent study of mechanical flexibility of single-crystal transistors, the device field-effect mobility was found to change as a function of bending radius and strain. When the substrate was bent from a radius of 7.4 mm to 5.9 mm, the mobility dramatically drops more than two orders of magnitude. The bending was believed to induce a large interfacial strain on the crystal and possibly the dielectric, which results in a decrease of mobility. In another study of the bending effect on the electrical properties of flexible organic thin-film transistors on stainless steel substrates, the compressive strain was found to result in an increased mobility, while the tensile strain degraded the electrical performance. The mechanical strains were believed to influence the energy barrier height between the grains of pentacene thin films, thereby resulting in the variation of channel resistances. In another study, the graphene structure on polyethylene terephthalate (PET) flexible substrate was demonstrated to function as a flexible and transparent electrode for field emission displays. Thin films consisting of crosslinked nanoparticle aggregates have been shown to function as highly sensitive strain gauges which exploits the exponential dependence of the interparticle tunnel resistance on the particle separation. Importantly, the modeling of the strain gauge behavior predicts the dependence of the gauge factor on several parameters, including the nanoparticle size, the interparticle separation gap, and the conductance of the linker molecules.

These previous studies have demonstrated the importance of strain effect on flexible device performance. However, little has been addressed for one of the critical factors responsible for the strain-induced responses, i.e., the molecular atmosphere in the device strain environment. In a recent report of our preliminary work, it was hypothesized that the resistance of nanoparticle thin film assemblies on flexible chemiresistor devices under strain could change significantly as a result of the change in dielectric properties. An in-depth investigation is thus needed for assessing the bending responses of the nanostructured flexible devices in different bending environment. In this report, we describe new findings of an investigation of the electrical conductivity properties of molecularly-mediated thin film assemblies of nanoparticles on flexible chemiresistor devices under different conformal wrapping or bending conditions and different exposure molecules. One important focus is the understanding of the resistance dependence on the bending directions for the devices exposed to various gas/vapor molecules. The goal is to gain fundamental insights into the correlation between the electrical response characteristics of the detailed nanostructures and the device stain parameters.

Device bending was performed manually by wrapping the flexible device around a cylinder with a defined diameter. FIG. 18A shows an example of the flexible sensor device coated with an NDT (1,9-nonadithiol) linked Au nanoparticle (2-nm) thin film under concave wrapping, i.e., tensile strain. Details for the quantitative analysis of the mechanisms for the molecularly-mediated thin film assembly in terms of film mass or thickness growth kinetics were described in our previous reports. As shown by the AFM image (FIG. 1B), the thin film of nanoparticles displays a relatively uniform morphology. The NDT-linked DT-$Au_{2nm}$ (NDT-$Au_{2nm}$) thin films were assembled as sensing materials with a thickness of about 320 nm. The molecularly-mediated thin film assemblies of gold nanoparticles by different linker molecules have been characterized in terms of thin film morphology, crystalline structure, nanoparticle ordering, interparticle molecular interaction, and interparticle distance properties using transmission electron microscopy, x-ray powder diffraction and Grazing-angle x-ray diffraction, FTIR, etc., details of which were described in our previous reports.

Two specific orientations of the interdigitated copper microelectrode lines in the flexible device were examined with respect to the wrapping direction: vertical and horizontal (FIG. 18A). The thin film assembly on the microelectrode patterns undergoes compressive strain or tensile strain depending on the wrapping direction. The changes of the resistance in response to bending of the device were measured under different radius of curvature upon bending of the flexible device along the indicated directions as shown in FIG. 18C. For bending at specific radius of curvature ($R_b$) (FIG. 18D), one cycle is defined as "Flat-Concave bending-Flat-Convex bending-Flat" ("F-C-F-V"). The differential resistance changes ($\Delta R/R$) were measured in each cycle in terms of concave bending ("CC", i.e., compressive strain) and convex bending ("CV", i.e., tensile strain). The viability of the flexible device's tolerance toward bending or wrapping was also examined in multiple cycles of bending.

The overall electrical conduction (electron hopping and/or electron tunneling) of the nanostructured thin film assemblies on the flexible substrates depends on several nanostructural parameters such as particle core radius (r), interparticle distance (d), and dielectric constant of interparticle medium ($\in$). By controlling the number of methylene groups of the linking molecules and the particle sizes, the electrical conductivity of the nanoparticle thin film assemblies in the absence of device strains has been found to follow the thermally-activated conduction pathway in which the activation energy increases with the interparticle distance and decreases with the particle size, details of which are described in our previous reports. In the present study, the electrical conductivity vs. device strain correlation for the flexible device coated the nanoparticle thin film assemblies is the focus of our investigation. The relative change in electrical resistance or conductivity of the nanostructured thin films in response to conformal device bending is first modeled in terms of concave or convex wrapping of the device. The electrical conductivity of the thin films can be described by a thermally-activated conduction path in Equation (9):

$$\sigma = \sigma_0 \exp(-\beta d)\exp\left[-\frac{0.5e^2}{4\pi\varepsilon\varepsilon_0 RT}\left(\frac{1}{r} - \frac{1}{r+d}\right)\right] \quad (9)$$

where $e=1.6\times10^{-19}$ C, $\in_0 = 8.854\times10^{-12}$ F/m, $R=1.38\times10^{-23}$ J/K, T=300 K, $\beta$ is the electron coupling term, and r and d represent particle radius and interparticle spacing (nm), respectively. In our previous study, the electron coupling term ($\beta$) was shown to be dependent on particle size, and relatively independent on the distance of the interparticle linkages. Assuming that the change of the interparticle distances from flat ($d_1$) to bent ($d_2$) is $\Delta L$ (=$d_2-d_1$), the ratio of the electrical conductivity can be written as in Equation (10):

$$\frac{\sigma_2}{\sigma_1} = \exp[-\beta(d_2 - d_1)]\exp\left[\frac{0.5e^2}{4\pi\varepsilon\varepsilon_0 RT}\left(\frac{1}{r+d_2} - \frac{1}{r+d_1}\right)\right] \text{ or} \quad (10)$$

$$\frac{R_2}{R_1} = \frac{\sigma_1}{\sigma_2} = \exp[-\beta(d_1 - d_2)]\exp\left[\frac{0.5e^2}{4\pi\varepsilon\varepsilon_0 RT}\left(\frac{1}{r+d_1} - \frac{1}{r+d_2}\right)\right]$$

This ratio contains two exponential components. The first component is mainly determined by the interparticle distance change and the β value ("β-d component"), whereas the second component is largely dependent on the particle size, interparticle distance change, and ∈ value ("∈-r component"). Assume that ∈=10 and T=300 K, the $R_2/R_1$ ratio is derived as shown in Equation (11):

$$\frac{R_2}{R_1} = \exp[\beta(d_2 - d_1)]\exp\left[2.78 \text{ nm} \times \left(\frac{1}{r+d_1} - \frac{1}{r+d_2}\right)\right] \quad (11)$$

Consider now the relative contributions of the above two components to the electrical conductivity of the thin films under different device strain effects. The "β-d component" is largely determined by the strain effect ($\in_{strain}$) as shown in Equation (12):

$$\varepsilon_{Strain} = \frac{\Delta L}{L} = \frac{d_2 - d_1}{2r + d_1} = \frac{T_s}{2R_b} \quad (12)$$

For our nanoparticle thin film coated flexible PET substrate, the substrate thickness $T_s$=125 μm, the radius of bending $R_b$=5 mm=5,000 μm, r=1 nm, and $d_1$=1.6 nm. In our earlier report, we obtained β=4.0 $nm^{-1}$. Substituting these values into the equation, we can express the $\Delta R/R_1$ ratio as a function of Strain $\in_{strain}$, in Equation (13):

$$\frac{\Delta R}{R_1} = \frac{R_2 - R_1}{R_1} = \quad (13)$$
$$\exp[3.6 \times \beta\varepsilon_{Strain}]\exp\left[2.78 \times \left(\frac{1}{2.6} - \frac{1}{2.6 + 3.6 \times \varepsilon_{Strain}}\right)\right] - 1$$

In this case, $\Delta R/R_1$ would be dependent on $\in_{strain}$. FIG. 19A shows the plot of $\Delta R/R_1$ vs. $\in_{strain}$ for both convex (tensile strain) and concave (compressive strain) wrapping directions. There are three observations. First, $\Delta R/R_1$ increases with $\in_{strain}$. Second, the magnitude of $\Delta R/R_1$ is larger for tensile strain than that for compressive strain. Third, the magnitude of $\Delta R/R_1$ depends on particle size and β value. $\Delta R/R_1$ is greater for larger sized particles if all other parameters are fixed. At fixed particle size, $\Delta R/R_1$ is greater for larger β value.

For the "∈-r component", we consider the possible change of ∈ due to the filling in the interparticle void spaces with gas/vapor molecules as a result of device exposure in different bending environment. The derived changes in electrical resistance for CV and CC wrapping directions are as shown in Equations (14a) and (14b):

$$\frac{\Delta R}{R_{1(CV)}} = \exp[900/R_b]\exp\left[\frac{27.8 \text{ nm}}{\varepsilon} \times \left(\frac{1}{2.6} - \frac{1}{2.6 + \frac{225}{R_b}}\right)\right] - 1 \quad (14a)$$

$$\frac{\Delta R}{R_{1(CC)}} = \exp[-900/R_b]\exp\left[\frac{27.8 \text{ nm}}{\varepsilon} \times \left(\frac{1}{2.6} - \frac{1}{2.6 - \frac{225}{R_b}}\right)\right] - 1 \quad (14b)$$

In this case, $\Delta R/R_1$ would be dependent on ∈ under a fixed $R_b$. FIG. 19B shows the plots of $\Delta R/R_1$ vs. $R_b$ for both convex (tensile strain) and concave (compressive strain) wrapping directions. In addition to the observation of $\Delta R/R_1$ increase with $R_b$, and the opposite signs for both convex (tensile strain) and concave (compressive strain) wrapping directions, the magnitude of $\Delta R/R_1$ decreases with the increase of ∈.

Figure 20C:
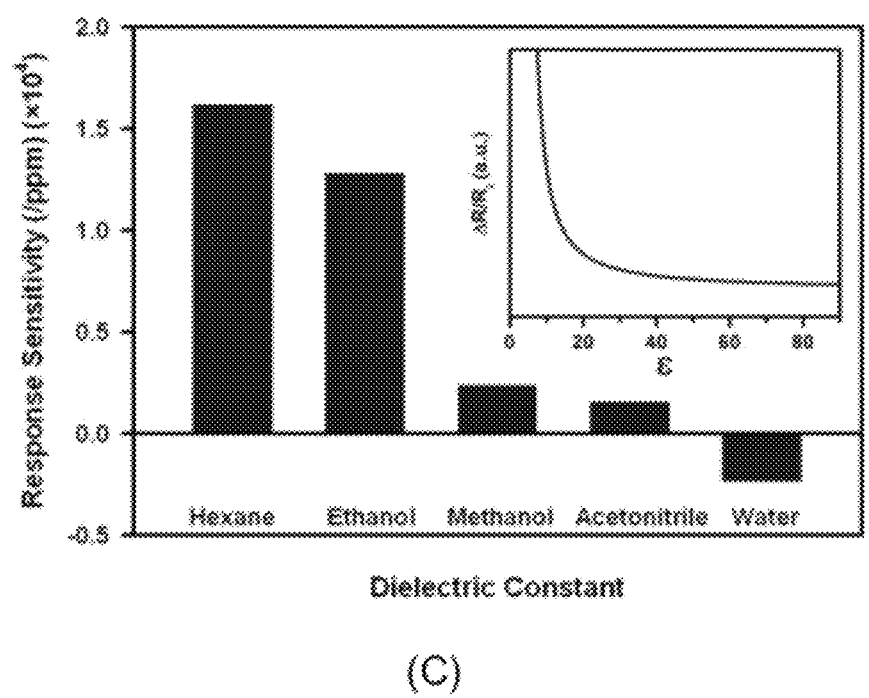
FIG. 20C depicts a plot comparing the response sensitivities upon exposures to different vapors including hexane ($\in$=1.9), ethanol ($\in$=25.3), methanol ($\in$=33.0), acetonitrile ($\in$=36.6), and water ($\in$=80.1), wherein the vapor concentration is given in the unit of ppm moles per liter (ppm (M)), which can be converted to ppm (V) by multiplying a factor of 24.5.

The electrical conductivity of the flexible device under no device strain in response to exposures to vapors with different dielectric constants was first examined. FIGS. 20A-C shows a representative set of the sensor response ($\Delta R/R$ where R represents $R_1$) and sensitivity profiles for NDT-$Au_{2nm}$ (FIG. 20A) and MUA (11-mercaptoundecanoic acid) linked Au nanoparticle (MUA-$Au_{2nm}$) (FIG. 20B) films in response to hexane and water vapors. Glass substrate was used in this case to ensure absolutely no device strain. The response profile features an increase in absolute value of $\Delta R/R$ upon exposure to vapor which returns to baseline upon purge with nitrogen. The response is rapid and reversible. In most cases, the responses increased linearly with vapor concentration when the concentration is not too high. The slope serves as a measure of the response sensitivity. Deviation from the linear relationship occurs when the vapor concentration is above a certain value, the exact value of which depends on the vapor. Such a deviation is due to the existence of a saturation effect and or the complication of both bulk and surface adsorption phenomena. For the convenience of an overall assessment of the data, we used the linear approximation for assessing the response data. In general, the response sensitivities of MUA-$Au_{2nm}$ are higher than those of NDT-$Au_{2nm}$ films to vapors on the same channel because of the correlation of the electrical signals depending on the three nanostructural parameters, r, d, and ∈. An important finding from FIGS. 20A-B is that the devices exhibited an opposite response characteristic between the two different films for water vapor. In contrast to the small positive response characteristic observed for NDT-$Au_{2nm}$ film, the data for the MUA-$Au_{2nm}$ film showed a negative trend in response.

The understanding of how dielectric constants of the analytes correlate with sensor responses is important because the electrical conductivity is dependent on the dielectric properties of the thin film in a significant way. The basic concept is that the dielectric constant of the nanostructured sensing thin film may change as a result of the sorption of the vapor with different dielectric constants. Since the sorption of vapors in the nanostructured film is expected to increase the dielectric constant of the thin film materials, the response of the thin films to vapors with low dielectric constant could be very different from those for vapors with high dielectric constants. We examined the response characteristics of the nanostructured sensing thin films in response to a number of volatile organic compounds with different dielectric constants, including hexane, ethanol, methanol, acetonitrile, water, etc. In contrast to vapors such as hexane, which has a very low dielectric constant (∈~2), vapors such as ethanol, methanol, acetonitrile, and water exhibit ∈ values ranging from 20 to 80. The response profiles of the MUA-$Au_{2nm}$ thin film revealed a remarkable positive-negative switching characteristic between positive and negative response profiles. By comparing the signs and the magnitudes of the response sensitivities of each device in response to the vapors with different dielectric constants (FIG. 20C), one of the most important observations is the dependence of the response sensitivities on the dielectric constants of the vapor.

In general, the change in resistance decreases with the increase in $\in$ of the vapors, which is qualitatively consistent with the theoretical trend. When $\in$ is increased to above 30~40, the switching from the usual positive response to the negative response characteristic becomes evident. In addition, the magnitude of the response also seem to show such a remarkable trend: it increases with the decrease of the dielectric constant for vapors with the lower dielectric constants; it increases with $\in$ for vapors with higher dielectric constants. This finding shows that the change of the vapor adsorption induced changes in dielectric properties in the nanostructured thin film plays a key role in the nanoparticle-structured sensor response characteristics.

The response characteristics upon device bending were examined under different radii of curvatures and different vapor-exposure environments, including nitrogen, hexane, ethanol, acetonitrile, and water vapors. The selection of these vapors was based on the differences in a combination of the molecular polarity, hydrophobicity/hydrophilicity, and dielectric constant. The results are discussed below in terms of response characteristics under small device strain, large device strain, and different device bending orientations with respect to the microelectrode orientation.

First, the device response characteristics are compared between the resistance response data obtained under nitrogen (dry environment) and those obtained upon device exposure to different vapor molecules under relatively small device strain, i.e., $R_b \geq 10$ mm (or strain $\in_{strain} \leq 6.3 \times 10^{-3}$). FIG. 21A shows a representative set of $\Delta R/R$ vs. bending ($R_b = 10$ mm) under nitrogen atmosphere for a device coated with NDT-$Au_{2nm}$ film. The value of $\Delta R/R$ is negative for the concave bending and positive for the convex bending. The average value of $\Delta R/R$ was found to be $-0.57$ for the concave bending and $0.52$ for the convex bending. While there are small variations, a consistent response pattern is evident in which the concave bending decreases the resistance whereas the convex bending increases the resistance was observed.

FIG. 21B shows the $\Delta R/R$ change of the same device under water vapor (RH=86%). In sharp contrast to the results under the relatively dry condition, the resistance was found to decrease for both the concave and convex bending under the relatively humid testing environment. The average value of $\Delta R/R$ was $-0.37$ for the concave bending and $-0.30$ for the convex bending. The trends of the resistance change for the bending are the same for all the measurements repeated in several days.

Figure 21E:
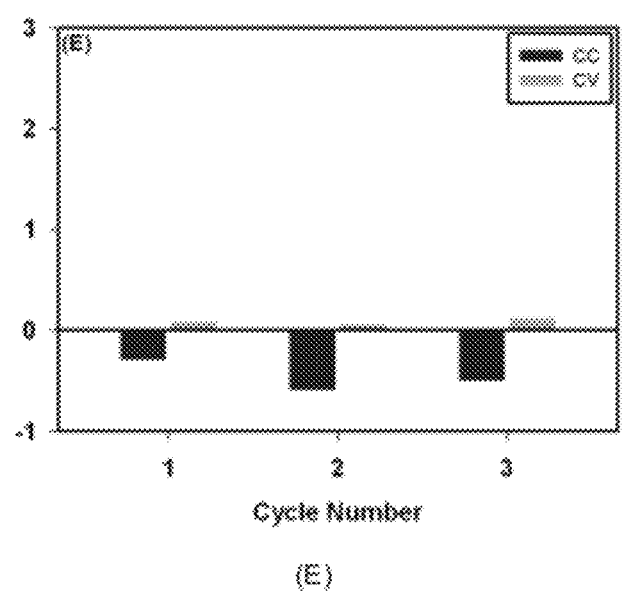
FIG. 21E depicts a plot of the differential resistance change, $\Delta R/R$, of a device coated with NDT-Au$_{2nm}$ film in response to repetitive flat vs. bending cycles for a device ($R_b$=10 mm) with the microelectrode pattern in the "vertical" orientation under acetonitrile (~2800 ppm)

The response patterns were further examined under other vapors, including hexane, ethanol, and acetonitrile with dielectric constants falling in between nitrogen and water vapors (FIG. 21C-E). For repetitive bending cycles of the device under hexane, the resistance was found to decrease for the concave bending and increase for the convex bending (FIG. 21C). The value of $\Delta R/R$ was found to be negative for the concave bending, suggesting the decreasing resistance, and positive for the convex bending, suggesting the increasing resistance. The average value of $\Delta R/R$ was $-0.55$ for concave bending and $2.1$ for convex bending.

For device bending under ethanol, similarly, the resistance was found to decrease for concave bending and increase for convex bending (FIG. 21D). The average value of $\Delta R/R$ was $-0.16$ for concave bending and $2.0$ for convex bending. For device bending under acetonitrile (FIG. 21E), the value of $\Delta R/R$ was found to be negative for the concave bending, and positive for the convex bending, the latter of which is much smaller than those under hexane and ethanol, exhibiting an average $\Delta R/R$ value of $-0.46$ for concave bending and $0.071$ for convex bending.

Figure 22:
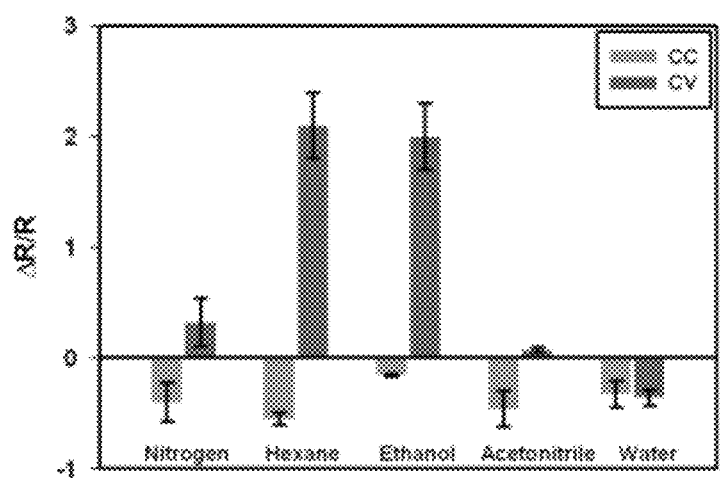
FIG. 22 depicts a plot of average $\Delta R/R$ values in response to convex and concave bending of a device coated with NDT-Au$_{2nm}$ film ($R_b$=10 mm) under different gas/vapor molecules.

In FIG. 22, the average values of $\Delta R/R$ obtained for different bending directions under different gas/vapor molecules are compared. In general, the concave bending decreases the resistance, whereas the convex bending increases. However, the magnitudes are different depending on the gas/vapor environment. The data showed the highest change for hexane and ethanol vapors. There appears a trend of decrease with increasing dielectric constant of the vapors for convex bending, exhibiting a negative $\Delta R/R$ response for water vapor. For concave bending the $\Delta R/R$ responses appear to show little dependent on the vapor environment.

As shown in the theoretical modeling, $\Delta R/R$ depends on a combination of $\in$ and $R_b$. Under all conditions except for water vapor, the concave warping decreases the resistance whereas convex bending increases the resistance, which is clearly consistent with the theoretical modeling. Under the humid condition, both concave bending and convex bending decrease the resistance. The trend of $\Delta R/R$ decrease with increasing dielectric constant of the vapors for convex bending, including the negative $\Delta R/R$ response for water vapor, does not seem to be explainable by the strain-dependent theoretical consideration (see, e.g., Equation 13). Rather, the $\in$-dependent theoretical consideration (see, e.g., Equation 14) seems to provide a good explanation of the trend. For hexane and ethanol vapors, the magnitude of the $\Delta R/R$ responses seems to be much larger (by a factor of ~10) than the theoretical changes using either strain- or $\in$-dependent theoretical responses ($\Delta R/R$=0.1~0.2). In contrast to convex bending in which more air can be accommodated in the enlarged interparticle voids leading to an increased resistance, there is less air ($\in \approx 1$) in between the particles for the case of concave bending. The average dielectric median constant is expected to increase. Therefore, concave bending leads to an increased conductivity.

Under water vapor, the concave bending leads to the expulsion of air between the interparticle voids since the interparticle spacing decreases. The concave bending under the high relative humidity increases the conductivity, similar the result under the dry condition. The convex bending enlarges the interparticle voids, leading to an increase of water molecules flowing into the interparticle voids. The dielectric constant of water vapor is much larger than air and the organic medium in the film, resulting in an increase of the average dielectric medium constant. This large increase is clearly associated with the observation of the negative $\Delta R/R$ values for water vapor. The tests with the other vapors substantiate the assessment. Hexane and ethanol have great solubility in the NDT-Au film, which qualitatively explain the large resistance increase. Acetonitrile is a polar molecule and does not have high solubility in the film, which qualitatively explains the small resistance increase. In comparison with the data under no device strain where similar dependence on dielectric constant was observed (see FIG. 20C), the finding suggests that the bending responses of electric conductivity under the relatively large radius of curvature is likely dominated by dielectric constant, while the device strain plays an additional role in fine tuning the electrical properties.

Secondly, the bending response was further examined under relatively large device strains, or smaller radii of curvature, i.e., $R_b < 10$ mm (or strain $\in_{strain} > 6.3 \times 10^{-3}$). For example, under different gases/vapors for $R_b = 3$ mm, the resistance was found to decrease upon concave bending whereas it increased upon convex bending (see Figure S1), consistent with the data obtained under $R_b = 10$ mm except for the water vapor. While there were variations from measurement to measurement due to the lack of precise control of the radius of curvature, the above response characteristics were clearly reproducible. Under dry condition, the average value of ΔR/R was found to be −0.19 for the concave bending and 0.23 for the convex bending. For hexane vapor, the average value of ΔR/R was −0.77 for the concave bending and 0.49 for the convex bending. For ethanol vapor, the average value of ΔR/R was −0.53 for the concave bending and 0.51 for the convex bending. For acetonitrile vapor, the average value of ΔR/R was −0.54 for the concave bending and 0.43 for the convex bending. For water vapor, the resistance was found to decreases for the concave bending and increase for the convex bending, in contrast to the resistance to the decrease for the convex bending under $R_b$=10 mm. The average value of ΔR/R was −0.30 for concave bending and 0.20 for convex bending, which quite close to those found under nitrogen condition.

Figure 23:
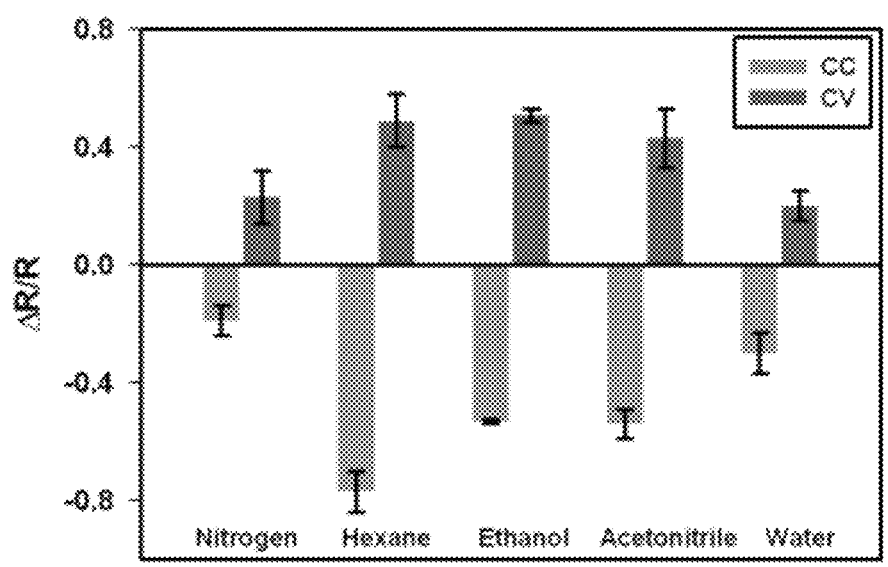
FIG. 23 depicts a plot of average $\Delta R/R$ values in response to convex and concave bending of a device coated with NDT-Au$_{2nm}$ film ($R_b$=3 mm) under different gas/vapor molecules.

The above data of resistance changes are compared in FIG. 23. In comparison with those obtained at $R_b$=10 mm, both concave and convex bending data at $R_b$=3 mm are again qualitatively consistent with the results of the theoretical modeling.

The trend of the ΔR/R decrease with increasing dielectric constant of the vapors for both convex and concave bending seem to be explainable the ∈-dependent theoretical consideration (see, e.g., Equation 13). However, the magnitude of the ΔR/R changes seems to be smaller than the ∈-dependent theoretical prediction. The magnitude of the ΔR/R changes is smaller than those under $R_b$=10 mm, which seems quite close to the strain-dependent theoretical consideration (see, e.g., Equation 13). This finding suggests that the bending responses under small radius of curvature is likely dominated by device strain, while the dielectric constant plays an additional role in fine tuning the electrical properties.

Lastly, we further compared responses of devices with two different microelectrode orientations, i.e., "vertical" and "horizontal" as illustrated in FIG. 18B for bending under relatively small radius of curvature ($R_b$=5 mm) for ethanol and acetonitrile vapors that have both polarity and dielectric constant falling in between hexane and water. The responses are compared between "horizontal" (A) and "vertical" (B), along with the responses under nitrogen. Under nitrogen (a), device A exhibits an average ΔR/R of −0.19 for the concave bending and 0.09 for the convex bending, whereas device B shows average ΔR/R of −0.23 for the concave bending and 0.06 for the convex bending. The differences between these two microelectrode pattern orientations are apparently very small under nitrogen.

In comparison with the responses under nitrogen, significant differences have been observed between these two microelectrode pattern orientations under ethanol and acetonitrile. For ethanol (c), device A exhibits an average ΔR/R of −0.07 for the concave bending and 0.056 for the convex bending, whereas device B shows an average ΔR/R of −0.29 for the concave bending and 1.2 for the convex bending. For acetonitrile (a), device A exhibits an average ΔR/R of −0.08 for the concave bending and 0.088 for the convex bending, whereas device B shows average ΔR/R of −0.56 for the concave bending and 0.28 for the convex bending. Note that device B tested under $R_b$=5 mm has the same microelectrode orientation as the devices tested under $R_b$=10 mm and 3 mm. The responses of the device B are largely consistent with the expected trend, with some variations due to subtle differences of the microelectrode parameters from device to device.

The above resistance changes are compared in FIGS. 24A-B. The differences between these two microelectrode pattern orientations are apparently very small under nitrogen, which appear to be consistent with the theoretical predictions for both strain induced and dielectric constant induced changes in resistance. However, there appear to be significant differences between the same two devices under ethanol and acetonitrile. The magnitude of the responses is smaller for the "horizontal" orientation than those for the "vertical" orientation (by a factor of 3~20 depending on the vapor molecule nature and the bending direction).

Theoretically, if the nanoparticle assembly has no specific ordering with respect to the microelectrode orientation, which appears to be the likely morphology, one would not expect any difference between the two orientations because of their identical strain. This is indeed true for the results obtained under nitrogen. However, under ethanol and acetonitrile, the observation of the difference suggests other possible factors. One possibility is that there is some degree of ordering for the nanoparticles in the thin film, and thus the strain-induced change of interparticle distances would be different between the two microelectrode orientations. Scheme 1 depicts an idealized model for the nanoparticles in the thin film assembly (e.g., (100) packing of the assembled nanoparticles). This model illustrates how the interparticle distances for the device with vertical microelectrode orientation under the same device bending direction would be different from that for the device with a horizontal orientation. In this case, the interparticle distance for the device with horizontal microelectrode orientation would increase more than that for the device with vertical microelectrode orientation under the same strain, which would increase the conductivity more significantly for the former case. This is however the opposite of the experimental observation under the two vapors for the bending of the two different microelectrode orientations.

Another possibility is that the change of the dielectric properties in the film could operate in such a way that the ordered interparticle spatial characteristic as shown in FIG. 25C would favor the enhancement in dielectric effect of the solvent molecules on the surface conductivity in comparison to that as shown in FIG. 25B. We do not have direct evidence at this point, but one hypothesis is that the more effective increase of dielectric constant in the film in FIG. 25C leads to resemblance of the surface to a layer of the adsorbed molecules. This type of resemblance would lead to a higher surface conductivity resembling ionic conductor, not electronic conductor, which could play a role in producing a more effective increase of the resistance in the case of FIG. 25C because of a better continuity of the molecules between the two microelectrodes. In this case, the higher the dielectric constant, the less conductance the film has. Within the two-microelectrode confinement, the film with a higher dielectric constant will conduct less because of a greater buildup of opposite charges on the two microelectrodes, which in fact results in a greater capacitance. This could be qualitatively explained by considering the capacitive characteristic of the surface with a layer of polar solvents, C=Q/V, where C=∈(A/d) (∈—dielectric constant of the fluid molecules; d—gap between electrodes, A—area of the electrodes, Q—change on the electrodes, and V—voltage across the electrodes). The voltage build up would be V=(Q/∈)(d/A), which is opposite of the applied voltage for the resistance measurement. This more effective voltage build up leads to an enhanced resistance of the film for the case of the vertical orientation than the horizontal orientation under the convex bending. Under concave bending, the reduced interparticle void space should then diminish the difference observed under the convex bending. This trend seems to be observed in the data for ethanol, but in the data for acetonitrile. To fully explain these differences, an in-depth impedance study of the electrical and capacitive properties of the thin films under the different bending and different vapors will be needed. In this study, the nanoparticle thin film assembly between the two microelectrodes is modeled by an equivalent circuit represented by a parallel combination of resistances and capacitances. The resistive and capacitive components can be distinguished by analysis of complex plane impedance spectra, which is part of our on-going work.

In conclusion, the electrical characteristics of the nanoparticle thin film assembly on flexible chemiresistor devices has been found to depend on a combination of the device strain and the exposure molecular environment. This dependence has been established by both theoretical modeling and experimental data. Under no device strain, the electrical conductivity is highly sensitive to the molecular nature in the exposure gas/vapor environment, revealing a clear increase in electrical conductivity with dielectric constant of the vapor molecules. Under small device strains, the electrical conductivity is shown to response sensitively to the strain directions (tensile vs. compressive strain), but also to the dielectric constant of the vapor molecules in a way similar to the characteristic observed under no device strain. Under relatively large device strains, the electrical conductivity is shown to respond to the change in dielectric constant of the vapor molecules, but more significantly to the device tensile and compressive strains than those under small device strains. This combination of device strain and dielectric characteristic is further shown to be dependent on the orientation of the microelectrode patterns with respect to the device strain direction. These findings have demonstrated how wrapping or bending influences the interparticle packing, ordering, and spatial structures of nanoparticle assemblies on flexible devices in the presence of gas/vapor molecules. These findings, upon gaining a further mechanistic insight into the structural and morphological changes of the thin films, will have important implications for the design of nanostructured flexible devices for sensing applications which require conformal wrapping or bending adaptability in various complex or special sensing environments.

Chemicals and Nanoparticles

Hydrogen tetrachloroaurate trihydrate (99%), tetraoctylammonium bromide (99%), decanethiol (DT, 96%), sodium borohydride (99%), 1,9-nonadithiol (NDT, 95%), and 11-mercaptoundecanoic acid (MUA, 95%) were obtained from Aldrich. Solvents included hexane (99.9%), toluene (99.9%), methanol (99.9%), and acetonitrile (99.8%), and ethanol (99.9%) from Aldrich. Water was purified with a Millipore Milli-Q water system.

Gold nanoparticles of 2-nm diameter ($Au_{2nm}$) encapsulated with decanethiolate monolayer shells were synthesized by two-phase reduction of $HAuCl_4$ according to Brust's two-phase protocol and a synthetic modification. The as-synthesized gold nanoparticles ($DT-Au_{2nm}$) had an average size of 2.0±0.7 nm. Gold nanoparticles with larger sizes were synthesized by a thermally-activated processing route developed in our laboratory. Briefly, the solution containing the as-synthesized $DT-Au_{2nm}$ nanoparticles from the synthesis was heated at 150° C. to produce larger-sized Au nanoparticles. Gold nanoparticles of 7.0±0.5 nm diameters ($Au_{7nm}$) produced by this method were used in this work. Details for the morphology and size distribution can be found in previous reports.

Preparation of Molecularly-Mediated Thin Film Assemblies of Nanoparticles

The DT-capped Au nanoparticles were assembled on the flexible chemiresistor devices using molecularly-mediated interparticle linking. For example, NDT-linked thin films ($NDT-Au_{2nm}$) were prepared via an "exchanging-crosslinking-precipitation" route using a $10^3$-$10^4$ ratio of NDT to Au nanoparticles. Briefly, a flexible device was immersed into the solution of $NDT-Au_{2nm}$ nanoparticles and NDT at room temperature for a controlled period of time, during which the solvent evaporation was prevented in the film formation. The resulting film-coated device was rinsed many times to remove any un-assembled components, and dried using nitrogen gas.

Device Fabrication

Interdigitated copper microelectrodes were patterned on polyethylene terephthalate (PET) (DuPont Tejin Films Melinex ST507) film with 125 μm thickness. The PET sheets were cleaned using isopropyl alcohol and oxygen plasma before sputtering of 5 nm Cr and 300 nm Cu films. The Cu microelectrode parameters are 400 μm for finger length, and 10 μm for finger spacing, and 10 μm for finger width. The total number of microelectrodes is 300 for each of the device. The microelectrode devices feature 150 pairs of microelectrodes with well-defined length, width and spacing. Some details for the microfabrication were reported previously.

Measurements

A 2000 mL of glass container (test chamber) was cleaned by distilled water and dried by $N_2$ gas. A humidity meter (USB-502-LCD) was taped on the wall of a glass container. A 5'×4' parafilm was cut and stretched to cover the container. The test chamber was purged with $N_2$ through the parafilm to lower the humidity. The device was connected to the computer-interfaced multi-channel meter (Keithley, Model 2700) to measure the resistance. The resistances were measured in the warping orders of flat, concave, flat, and convex. The wrapping was controlled manually using a cylinder with well-defined diameter. In the case of manual operation, we measured the radius of curvature using a ruler, which had a possible variation of about 15%. The measuring steps above were repeated for several times. After the experiment under relatively dry testing condition was done, 200 mL of distill water was added to the beaker, and a stirring bar was put in the beaker. When the humidity reached the maximum for 20 minutes, the measurements in response to the warping were tested. The same steps were repeated for device A and device B.

A Multimode Nano-Scope IIIa (Digital Instruments, Santa Barbara), equipped with an E scanner (maximum scan size: 16 μm), was utilized for AFM imaging. The capability of tapping mode (TM) AFM allows for imaging with minimum disruption to the nano structures. Standard silicon tapping cantilevers (nanosensors) were used with a force constant of 40 N/m (TESP). The probe has a nominal tip radius with a curvature of ~10 nm. All images were acquired in TM. The instrument was calibrated by imaging standard calibration gratings.

In view of the foregoing discussion, and in light of Example 1, Example 2, and Example 3, a small sample of systems, methods, and apparatus that that the present disclosure contemplates are described herein as follows below:

There is described (A1) a flexible chemiresistor (CR) module for sensing a molecule of interest comprising a flexible substrate; and a thin film nanoparticle assembly assembled on the flexible substrate, said thin film nanoparticle assembly comprising: metal or metal alloy core, ligand-capped nanoparticles, and molecular linkers connecting the nanoparticles. There is described (A2) the module of A1 wherein the flexible substrate is polyethylene terephthalate (PET), polyethylene naphthalate (PEN) or polyimide (PI). There is described (A3) the module of A1 wherein core material of the metal or metal alloy core is selected from the group consisting of gold, silver, platinum, iron oxide, gold-silver alloy, gold-platinum alloy, gold-copper alloy, or mixtures thereof. There is described (A4) the module of A1 wherein the thin film nanoparticle assembly has a particle radius (r), of 1 to 50 nm. There is described (A5) the module of A1 wherein the thin film nanoparticle assembly has an interparticle spacing (δ) of 0.5 to 5 nm. There is described (A6) the module of A1 wherein the thin film nanoparticle assembly has an interparticle dielectric constant (∈) of 1 to 80. There is described (A7) the module of A1, wherein the molecule of interest is a volatile organic compound (VOC) selected from the group consisting of acetone, toluene, benzene hexane, heptane, octane, iso-octane, cyclohexane, chloroform, tetrahydrofuran, ethyl acetate, methanol, ethanol, isopropanol, butanol, nitrobenzene and xylenes. There is described (A8) the module of A7, wherein the VOC is acetone. There is described (A9) the module of A1, wherein the molecular linkers are selected from the group consisting of α,ω-alkyldithiols, α,ω-dicarboxylic acids, mercaptocarboxylic acids, and combinations thereof. There is described (A10) the module of A9, wherein the molecular linkers are α,ω-alkyldithiols. There is described (A11) the module of A10, wherein the α,ω-alkyldithiol is HS—$(CH_2)_n$—SH, with n being 3-10. There is described (A12) the module of A9, wherein the molecular linkers are α,ω-dicarboxylic acids. There is described (A13) the module of A12, wherein the α,ω-dicarboxylic acid is $HO_2C$—$(CH_2)_n$—$CO_2H$, with n being 2 to 16. There is described (A14) the module of A9, wherein the molecular linkers are mercaptocarboxylic acids. There is described (A15) the module of A14, wherein the mercaptocarboxylic acids is HS—$(CH_2)_n$—$CO_2H$, with n being 2 to 18. There is described (A16) the module of A1, wherein the metal or metal alloy core, ligand-capped nanoparticles are capped with a nanoparticle capping ligand selected from the group consisting of alkanethiols, alkyl amines, alkyl alcohols, alkanoic acids, or mixtures thereof. There is described (A17) the module of A16, wherein the nanoparticle capping ligand is decanethiol. There is described (A18) the module of A1 having a high tolerance toward repeated bending or wrapping.

There is described (B1) a hand-held device comprising the module of A1 integrated in the hand-held device. There is described (B2) the hand-held device of B1 wherein the molecule of interest is acetone. There is described (B3) the hand-held device of B2 for detecting acetone in the breath stream of a mammalian subject.

There is described (C1) a flexible chemiresistor (CR) sensor for sensing a molecule of interest comprising: a sensor platform, wherein the sensor platform comprises the flexible chemiresistor (CR) module of A1. There is described (C2) the sensor of C1 comprising a plurality of different sensor platforms. There is described (C3) the sensor of C2, wherein the different sensor platforms differ with regard to nanoparticle capping ligands, nanoparticle cores, molecular linkers, and/or flexible substrate thickness. There is described (C4) the sensor of C1 wherein the nanoparticle cores differ by size or material. There is described (C5) the sensor of C1 wherein the nanoparticle capping ligands differ by size or material. There is described (C6) the sensor of C1 wherein the molecular linkers differ by length or chemical content. There is described (C7) the sensor of C1 comprising a plurality of transducers mounted on the sensor platform and operably linked to the sensor platform. There is described (C8) the sensor of C7 comprising: an artificial neural network; and a voltage source operably linked to the artificial neural network and the plurality of transducers, wherein the artificial neural network is designed to recognize contact of the molecule of interest with the sensor platform. There is described (C9) the sensor of C7 wherein the transducers are quartz-crystal microbalances. There is described (C10) the sensor of C7 wherein the transducers are interdigitated microelectrodes. There is described (C11) the sensor of C7 further comprising a microcontroller operably linked to the transducers. There is described (C12) the sensor of C7 further comprising a circuit board operably linked to the transducers. There is described (C13) the sensor of C7 further comprising software for data processing or pattern recognition. There is described (C14) the sensor of C7, wherein the neural network is trained to distinguish contact of the molecule of interest with the sensor platform from contact of other agents with the sensor platform. There is described (C15) the sensor of C13, wherein the neural network is trained to quantitate concentration of the molecule of interest contacting the sensor platform. There is described (C16) the sensor of C1, wherein the flexible substrate is polyethylene terephthalate (PET), polyethylene naphthalate (PEN) or polyimide (PI). There is described (C17) the sensor of C1, wherein core material of the metal or metal alloy core is selected from the group consisting of gold, silver, platinum, iron oxide, gold-silver alloy, gold-platinum alloy, gold-copper alloy, or mixtures thereof. There is described (C18) the sensor of C1, wherein the thin film nanoparticle assembly has a particle radius (r), of 1 to 50 nm. There is described (C19) the sensor of C1, wherein the thin film nanoparticle assembly has an interparticle spacing (δ) of 0.5 to 5 nm. There is described (C20) the sensor of C1, wherein the thin film nanoparticle assembly has an interparticle dielectric constant (∈) of 1 to 80. There is described (C21) the sensor of C1, wherein the molecule of interest is a volatile organic compound (VOC) selected from the group consisting of acetone, toluene, benzene hexane, heptane, octane, iso-octane, cyclohexane, chloroform, tetrahydrofuran, ethyl acetate, methanol, ethanol, isopropanol, butanol, nitrobenzene and xylenes. There is described (C22) the sensor of C21, wherein the VOC is acetone. There is described (C23) the sensor of C1, wherein the molecular linkers are selected from the group consisting of α,ω-alkyldithiols, α,ω-dicarboxylic acids, mercaptocarboxylic acids, and combinations thereof. There is described (C24) the sensor of C23, wherein the molecular linkers are α,ω-alkyldithiols. There is described (C25) the sensor of C24 wherein the α,ω-alkyldithiol is HS—$(CH_2)_n$—SH, with n being 3-10 There is described (C26) the sensor of C23, wherein the molecular linkers are α,ω-dicarboxylic acids. There is described (C27) the sensor of C26, wherein the α,ω-dicarboxylic acid is $HO_2C$—$(CH_2)_n$—$CO_2H$, with n being 2 to 16. There is described (C28) the sensor of C23 wherein the molecular linkers are mercaptocarboxylic acids. There is described (C29) the sensor of sensor of C28, wherein the mercaptocarboxylic acids is HS—$(CH_2)_n$—$CO_2H$, with n being 2 to 18 There is described (C30) the sensor of sensor of C1, wherein the metal or metal alloy core, ligand-capped nanoparticles are capped with a nanoparticle capping ligand selected from the group consisting of alkanethiols, alkyl amines, alkyl alcohols, alkanoic acids, or mixtures thereof. There is described (C31) the sensor of C30, wherein the nanoparticle capping ligand is decanethiol. There is described (C32) the sensor of C1 wherein the flexible CR module has a high tolerance toward repeated bending or wrapping.

There is described (D1) a hand-held device comprising the flexible CR sensor of C1 integrated in the hand-held device. There is described (D2) the hand-held device of D1 wherein the molecule of interest is acetone. There is described (D3) the hand-held device of D2 for detecting acetone in the exhaled breath of a mammalian subject.

There is described (E1) a method for detecting a molecule of interest in a fluid comprising the steps of: providing a fluid; and contacting the fluid with the flexible CR module of 1 or the flexible CR sensor of 21 under conditions effective to detect the molecule of interest in the fluid. There is described (E2) the method of E1, wherein the flexible substrate is polyethylene terephthalate (PET), polyethylene naphthalate (PEN) or polyimide (PI). There is described (E3) the method of E1, wherein core material of the metal or metal alloy core is selected from the group consisting of gold, silver, platinum, iron oxide, gold-silver alloy, gold-platinum alloy, gold-copper alloy, or mixtures thereof. There is described (E4) the method of E1, wherein the thin film nanoparticle assembly has a particle radius (r), of 1 to 50 nm. There is described (E5) the method of E1, wherein the thin film nanoparticle assembly has an interparticle spacing ($\delta$) of 0.5 to 5 nm. There is described (E6) the method of E1, wherein the thin film nanoparticle assembly has an interparticle dielectric constant ($\in$) of 1 to 80. There is described (E7) the method of E1, wherein the molecule of interest is a volatile organic compound (VOC) selected from the group consisting of acetone, toluene, benzene hexane, heptane, octane, iso-octane, cyclohexane, chloroform, tetrahydrofuran, ethyl acetate, methanol, ethanol, isopropanol, butanol, nitrobenzene and xylenes. There is described (E8) the method of E7, wherein the VOC is acetone. There is described (E9) the method of E1, wherein the molecular linkers are selected from the group consisting of $\alpha,\omega$-alkyldithiols, $\alpha,\omega$-dicarboxylic acids, mercaptocarboxylic acids, and combinations thereof. There is described (E10) the method of E9, wherein the molecular linkers are $\alpha,\omega$-alkyldithiols. There is described (E11) the method of E10, wherein the $\alpha,\omega$-alkyldithiol is HS—$(CH_2)_n$—SH, with n being 3-10. There is described (E12) the method of E9, wherein the molecular linkers are $\alpha,\omega$-dicarboxylic acids. There is described (E13) the method of E12, wherein the $\alpha,\omega$-dicarboxylic acid is $HO_2C$—$(CH_2)_n$—$CO_2H$, with n being 2 to 16. There is described (E14) the method of E9, wherein the molecular linkers are mercaptocarboxylic acids. There is described (E15) the method of E14, wherein the mercaptocarboxylic acids is HS—$(CH_2)_n$—$CO_2H$, with n being 2 to 18. There is described (E16) the method of E1, wherein the metal or metal alloy core, ligand-capped nanoparticles are capped with a nanoparticle capping ligand selected from the group consisting of alkanethiols, alkyl amines, alkyl alcohols, alkanoic acids, or mixtures thereof. There is described (E17) the method of E16, wherein the nanoparticle capping ligand is decanethiol. There is described (E18) the method of E1, wherein the fluid is a gas. There is described (E19) the method of E18, wherein the gas is a breath stream of a mammalian subject.

There is described (F1) a method for preparing a thin film nanoparticle assembly on a flexible substrate, said thin film nanoparticle assembly comprising metal or metal alloy core, ligand-capped nanoparticles and molecular linkers connecting the nanoparticles, comprising the steps of: providing a flexible substrate; and assembling the nanoparticles on the flexible substrate, wherein the assembling step comprises: the step of molecularly-mediated interparticle linking the nanoparticles, the step of stamping the nanoparticles, or the step of drop-casting the nanoparticles. There is described (F2) the method of F1 wherein the assembling step comprises the step of stamping the nanoparticles, said method further comprising the step of preparing a nanoparticle assembly ink for stamping prior to the step of stamping the nanoparticles. There is described (F3) the method of F2 wherein the stamping step comprises transferring the ink using a poly(dimethylsiloxane) (PDMS) stamp onto desired areas of the flexible substrate. There is described (F4) the method of F1 further comprising patterning microelectrodes on the flexible substrate. There is described (F5) the method of F1 wherein the flexible substrate is polyethylene terephthalate (PET), polyethylene naphthalate (PEN) or polyimide (PI). There is described (F6) the method of F1 wherein core material of the metal or metal alloy core is selected from the group consisting of gold, silver, platinum, iron oxide, gold-silver alloy, gold-platinum alloy, gold-copper alloy, or mixtures thereof. There is described (F7) the method of F1 wherein the thin film nanoparticle assembly has a particle radius (r), of 1 to 50 nm. There is described (F8) the method of F1 wherein the thin film nanoparticle assembly has an interparticle spacing ($\delta$) of 0.5 to 5 nm. There is described (F9) the method of F1 wherein the thin film nanoparticle assembly has an interparticle dielectric constant ($\in$) of 1 to 80. There is described (F10) the method of F1 wherein the molecular linkers are selected from the group consisting of $\alpha,\omega$-alkyldithiols, $\alpha,\omega$-dicarboxylic acids, mercaptocarboxylic acids, and combinations thereof. There is described (F11) the method of F10 wherein the molecular linkers are $\alpha,\omega$-alkyldithiols. There is described (F12) the method of F11 wherein the $\alpha,\omega$-alkyldithiol is HS—$(CH_2)_n$—SH, with n being 3-10. There is described (F13) the method of F10 wherein the molecular linkers are $\alpha,\omega$-dicarboxylic acids. There is described (F14) the method of F13 wherein the $\alpha,\omega$-dicarboxylic acid is $HO_2C$—$(CH_2)_n$—$CO_2H$, with n being 2 to 16. There is described (F15) the method of F10 wherein the molecular linkers are mercaptocarboxylic acids. There is described (F16) the method of F15 wherein the mercaptocarboxylic acids is HS—$(CH_2)_n$—$CO_2H$, with n being 2 to 18. There is described (F17) the method of F1 wherein the metal or metal alloy core, ligand-capped nanoparticles are capped with a nanoparticle capping ligand selected from the group consisting of alkanethiols, alkyl amines, alkyl alcohols, alkanoic acids, or mixtures thereof. There is described (F18) the method of F17 wherein the nanoparticle capping ligand is decanethiol.

The citation of any publication is for its disclosure prior to the filing date and should not be construed as an admission that the present invention is not entitled to antedate such publication by virtue of prior invention. All references cited herein are incorporated herein by reference in their entirety and for all purposes to the same extent as if each individual publication, patent or patent application was specifically and individually indicated to be incorporated by reference in its entirety for all purposes.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A flexible chemiresistor module for sensing a molecule of interest, said flexible chemiresistor module comprising:
   a flexible substrate; and
   a thin film nanoparticle assembly disposed on the flexible substrate, said thin film nanoparticle assembly comprising:
      metal or metal alloy core, ligand-capped nanoparticles comprising a nanoparticle capping ligand,
      molecular linkers connecting adjacent ones of the metal or metal alloy core, ligand-capped nanoparticles, the molecular linkers comprising mercaptocarboxylic acid with a carboxyl end forming hydrogen bonds with the metal or metal alloy core, ligand-capped nanoparticles, and
      a plurality of microelectrodes coupled to one or more of the metal or metal alloy core, ligand-capped nanoparticles,
   wherein the flexible substrate and the thin film nanoparticle assembly are configured to bend from a first orientation to a second orientation, which is different than the first orientation,
   wherein the thin film assembly adheres to the flexible substrate via hydrophobic interaction between the flexible substrate and the nanoparticle capping ligand of the ligand-capped nanoparticles,
   wherein the first orientation is planar and the second orientation configures the substrate and the thin film nanoparticle assembly to conformally adapt to a cylinder of a defined diameter by convex bending and concave bending, and
   wherein the thin film nanoparticle assembly is configured to maintain chemical sensitivity in response to exposure to the molecule of interest to induce an electrical signal across the plurality of microelectrodes in the second orientation.

2. The flexible chemiresistor module of claim 1, wherein the flexible substrate comprises polyethylene terephthalate (PET), polyethylene naphthalate (PEN), or polyimide (PI).

3. The flexible chemiresistor module of claim 1, wherein the metal or metal alloy core comprises one or more of gold, silver, platinum, iron oxide, gold-silver alloy, gold-platinum alloy, gold-copper alloy, and mixtures thereof.

4. The flexible chemiresistor module of claim 1, wherein the thin film nanoparticle assembly comprises particles with a particle radius (r) of 1 to 50 nm.

5. The flexible chemiresistor module of claim 1, wherein the molecule of interest is a volatile organic compound (VOC) selected from the group consisting of acetone, toluene, benzene hexane, heptane, octane, iso-octane, cyclohexane, chloroform, tetrahydrofuran, ethyl acetate, methanol, ethanol, isopropanol, butanol, nitrobenzene and xylenes.

6. The flexible chemiresistor module of claim 1, wherein the nanoparticle capping ligand comprises one or more of alkanethiols, alkyl amines, alkyl alcohols, alkanoic acids, and mixtures thereof.

7. The flexible chemiresistor module of claim 6, wherein the nanoparticle capping ligand differ by size, material, or chemical structure on one or more of the metal or metal alloy core, ligand-capped nanoparticles.

8. The flexible chemiresistor module of claim 6, wherein the nanoparticle capping ligand comprises decanethiol.

9. The flexible chemiresistor module of claim 1, wherein the metal or metal alloy core, ligand-capped nanoparticles differ by size or material.

10. The flexible chemiresistor module of claim 1, wherein the molecular linkers differ by length, chemical content, or chemical structure.

11. The flexible chemiresistor module of claim 10, wherein the molecular linkers further comprise $\alpha,\omega$-alkyldithiols.

12. The flexible chemiresistor module of claim 11, wherein the electrical signal corresponds with an electrical property that can be configured by the degree and direction of bending as between the first orientation and the second orientation.

* * * * *